US011505795B2

(12) United States Patent
Shendure et al.

(10) Patent No.: US 11,505,795 B2
(45) Date of Patent: *Nov. 22, 2022

(54) ERROR DETECTION IN SEQUENCE TAG DIRECTED SEQUENCING READS

(71) Applicant: University of Washington, Seattle, WA (US)

(72) Inventors: Jay Shendure, Seattle, WA (US); Joseph Hiatt, Seattle, WA (US); Rupali Patwardhan, Seattle, WA (US); Emily Turner, Seattle, WA (US)

(73) Assignee: University of Washington, Seattle, WA (US)

( * ) Notice: Subject to any disclaimer, the term of this patent is extended or adjusted under 35 U.S.C. 154(b) by 296 days.

This patent is subject to a terminal disclaimer.

(21) Appl. No.: 16/804,415

(22) Filed: Feb. 28, 2020

(65) Prior Publication Data

US 2020/0332283 A1 Oct. 22, 2020

Related U.S. Application Data

(63) Continuation of application No. 15/594,476, filed on May 12, 2017, now Pat. No. 10,577,601, which is a continuation of application No. 15/148,928, filed on May 6, 2016, now Pat. No. 10,227,585, which is a continuation of application No. 14/479,122, filed on Sep. 5, 2014, now abandoned, which is a continuation of application No. 13/759,292, filed on Feb. 5, 2013, now Pat. No. 8,846,347, which is a continuation of application No. 12/559,124, filed on Sep. 14, 2009, now Pat. No. 8,383,345.

(60) Provisional application No. 61/096,720, filed on Sep. 12, 2008.

(51) Int. Cl.

| | |
|---|---|
| C12P 19/34 | (2006.01) |
| C12N 15/10 | (2006.01) |
| C12N 15/66 | (2006.01) |
| C12Q 1/6869 | (2018.01) |
| C40B 40/06 | (2006.01) |
| C40B 50/06 | (2006.01) |
| C12Q 1/6874 | (2018.01) |
| C12Q 1/6806 | (2018.01) |

(52) U.S. Cl.
CPC ..... *C12N 15/1065* (2013.01); *C12N 15/1093* (2013.01); *C12N 15/66* (2013.01); *C12Q 1/6806* (2013.01); *C12Q 1/6869* (2013.01); *C12Q 1/6874* (2013.01); *C40B 40/06* (2013.01); *C40B 50/06* (2013.01)

(58) Field of Classification Search
CPC .................................................. C12Q 1/6869
See application file for complete search history.

(56) References Cited

U.S. PATENT DOCUMENTS

| | | |
|---|---|---|
| 5,130,238 A | 7/1992 | Malek |
| 5,185,243 A | 2/1993 | Ullman |
| 5,223,414 A | 6/1993 | Zarling |
| 5,455,166 A | 10/1995 | Walker |
| 5,573,907 A | 11/1996 | Carrino |
| 5,599,675 A | 2/1997 | Brenner |
| 5,641,658 A | 6/1997 | Adams |
| 5,679,524 A | 10/1997 | Nikiforov |
| 5,750,341 A | 5/1998 | Macevicz |
| 5,858,671 A | 1/1999 | Jones |
| 5,965,443 A | 10/1999 | Reznikoff et al. |
| 6,210,891 B1 | 4/2001 | Nyren |
| 6,214,587 B1 | 4/2001 | Dattagupta |
| 6,258,568 B1 | 7/2001 | Nyren |
| 6,261,782 B1 | 7/2001 | Lizardi et al. |
| 6,274,320 B1 | 8/2001 | Rothberg |
| 6,355,431 B1 | 3/2002 | Chee |
| 6,383,754 B1 | 5/2002 | Kaufman et al. |
| 6,437,109 B1 | 8/2002 | Reznikoff et al. |
| 6,593,113 B1 | 7/2003 | Tenkanen et al. |
| 6,777,187 B2 | 8/2004 | Makarov |
| 6,828,098 B2 | 12/2004 | Langmore |
| 7,001,792 B2 | 2/2006 | Sauer |
| 7,057,026 B2 | 6/2006 | Barnes |
| 7,115,400 B1 | 10/2006 | Adessi |
| 7,138,267 B1 | 11/2006 | Jendrisak et al. |
| 7,211,414 B2 | 5/2007 | Hardin |
| 7,244,559 B2 | 7/2007 | Rothberg |
| 7,315,019 B2 | 1/2008 | Turner |
| 7,329,492 B2 | 2/2008 | Hardin |
| 7,399,590 B2 | 7/2008 | Piepenburg |
| 7,405,281 B2 | 7/2008 | Xu |
| 7,537,897 B2 | 5/2009 | Brenner et al. |

(Continued)

FOREIGN PATENT DOCUMENTS

| | | |
|---|---|---|
| EP | 0320308 B1 | 11/1993 |
| EP | 0336731 B1 | 5/1994 |

(Continued)

OTHER PUBLICATIONS

Mardis, E.R., "The Impact of Next-Generation Sequencing Technology on Genetics," Trends in Genetics 24(3):133-141, Mar. 2008.

(Continued)

*Primary Examiner* — Kenneth R Horlick

(74) *Attorney, Agent, or Firm* — Christensen O'Connor Johnson Kindness PLLC

(57) ABSTRACT

The invention provides methods for preparing DNA sequencing libraries by assembling short read sequencing data into longer contiguous sequences for genome assembly, full length cDNA sequencing, metagenomics, and the analysis of repetitive sequences of assembled genomes.

20 Claims, 19 Drawing Sheets

Specification includes a Sequence Listing.

(56) References Cited

U.S. PATENT DOCUMENTS

| | | |
|---|---|---|
| 7,582,420 B2 | 9/2009 | Oliphant |
| 7,595,883 B1 | 9/2009 | El Gamal |
| 7,611,869 B2 | 11/2009 | Fan |
| 7,622,281 B2 | 11/2009 | Ronaghi et al. |
| 7,670,810 B2 | 3/2010 | Gunderson |
| 7,741,463 B2 | 6/2010 | Gormley |
| 3,003,354 A1 | 8/2011 | Shen |
| 8,563,477 B2 | 10/2013 | Smith |
| 2001/0046669 A1 | 11/2001 | McCobmie |
| 2002/0055100 A1 | 5/2002 | Kawashima |
| 2004/0002090 A1 | 1/2004 | Mayer |
| 2004/0096853 A1 | 5/2004 | Mayer |
| 2004/0110191 A1 | 6/2004 | Winkler et al. |
| 2004/0259229 A1 | 12/2004 | Thevelein et al. |
| 2005/0191698 A1 | 9/2005 | Chee |
| 2006/0024681 A1 | 2/2006 | Smith et al. |
| 2006/0040297 A1 | 2/2006 | Leamon |
| 2006/0216309 A1 | 9/2006 | Holden |
| 2006/0292611 A1 | 12/2006 | Berka |
| 2007/0128610 A1 | 6/2007 | Buzby |
| 2007/0128624 A1 | 6/2007 | Gormley |
| 2008/0009420 A1 | 1/2008 | Schroth |
| 2008/0108082 A1 | 5/2008 | Rank |
| 2008/0234136 A1 | 9/2008 | Drmanac |
| 2008/0242560 A1 | 10/2008 | Gunderson |
| 2009/0026082 A1 | 1/2009 | Rothberg |
| 2009/0032401 A1 | 2/2009 | Ronaghi |
| 2009/0047680 A1 | 2/2009 | Lok |
| 2009/0127589 A1 | 5/2009 | Rothberg |
| 2009/0176234 A1 | 7/2009 | Drmanac |
| 2010/0022403 A1 | 1/2010 | Kurn et al. |
| 2010/0069263 A1 | 3/2010 | Shendure et al. |
| 2010/0111768 A1 | 5/2010 | Banerjee et al. |
| 2010/0120098 A1 | 5/2010 | Grunenwald et al. |
| 2010/0137143 A1 | 6/2010 | Rothberg et al. |
| 2010/0282617 A1 | 11/2010 | Rothberg |
| 2011/0014657 A1 | 1/2011 | Rigatti et al. |
| 2011/0059865 A1 | 3/2011 | Smith et al. |
| 2011/0311506 A1 | 12/2011 | Craig et al. |
| 2012/0053063 A1 | 3/2012 | Rigatti et al. |
| 2012/0129704 A1 | 5/2012 | Gunderson et al. |
| 2012/0208724 A1 | 5/2012 | Steemers |
| 2012/0208705 A1 | 8/2012 | Steemers |
| 2012/0270305 A1 | 10/2012 | Williamson et al. |
| 2013/0203605 A1 | 8/2013 | Shendure et al. |
| 2013/0338042 A1 | 12/2013 | Shen et al. |
| 2014/0079923 A1 | 3/2014 | George et al. |
| 2014/0093916 A1 | 4/2014 | Belyaev |

FOREIGN PATENT DOCUMENTS

| | | |
|---|---|---|
| EP | 0439182 B1 | 4/1996 |
| EP | 2 712 931 A1 | 4/2014 |
| WO | 8909835 A1 | 10/1989 |
| WO | 8910977 A1 | 11/1989 |
| WO | 8912696 A1 | 12/1989 |
| WO | 9001069 A1 | 2/1990 |
| WO | 9106678 A1 | 5/1991 |
| WO | 9523875 A1 | 9/1995 |
| WO | 98/44151 A1 | 10/1998 |
| WO | 2004018497 A2 | 3/2004 |
| WO | 2004/042078 A1 | 5/2004 |
| WO | 2005065814 A2 | 7/2005 |
| WO | 2005/100585 A2 | 10/2005 |
| WO | 2007/098279 A2 | 8/2007 |
| WO | 2007123744 A2 | 11/2007 |
| WO | 2010/002883 A2 | 1/2010 |
| WO | 2010/048605 A1 | 4/2010 |
| WO | 2012/025250 A1 | 3/2012 |
| WO | 2012/058096 A1 | 5/2012 |
| WO | 2012/061832 A1 | 5/2012 |
| WO | 2012/103545 A1 | 8/2012 |
| WO | 2012/106546 A2 | 8/2012 |
| WO | 2013/177220 A1 | 11/2013 |
| WO | 2013/184796 A1 | 12/2013 |
| WO | 2014/142850 A1 | 9/2014 |

OTHER PUBLICATIONS

Reinhardt, J.A., et al., "De Novo Assembly Using Low-Coverage Short Read Sequence Data From the Rice Pathogen Pseudomonas syringae pv. oryzae," Genome Research 19(2):294-305, Feb. 2009.

Sorber, K., et al., "The Long March: A Sample Preparation Technique That Enhances Contig Length and Coverage by High-Throughput Short-Read Sequencing," PLoS ONE 3(10):e3495, Oct. 2008, 9 pages.

Wold, B., and R.M. Myers, "Sequence Census Methods for Functional Genomics," Nature Methods 5(1):19-21, Jan. 2008.

Zerbino, D.R., and E. Birney, "Velvet: Algorithms for De Novo Short Read Assembly Using de Bruijn Graphs," Genome Research 18(5):821-829, Mar. 2008.

Mizuuchi, K., "Transpositional Recombination: Mechanistic Insights From Studies of Mu and Other Elements," Annual Reviewsof Biochemistry 61:1011-1051, 1992.

Sundquist, A., et al., "Whole-Genome Sequencing and Assembly with High-Throughput, Short-Read Technologies," PLoS ONE 2(5):e484, May 2007.

Third Office Action dated Nov. 6, 2015, issued in Chinese Application No. CN201280012945.4, filed Feb. 2, 2012, 21 pages.

Van Berkum, N.L., et al., "Method to Study the Three-Dimensional Architecture of Genomes," Journal of Visualized Experiments 39, May 2010, 7 pages.

Van Steensel, B., and J. Dekker, "Genomics Tools for Unraveling Chromosome Architecture," Nature Bitoechnology 28:1089-1095, Oct. 2010.

Wang, H., et al., "Calling Cards Enable Multiplexed Identification of Genomic Targets of DNA-Binding Proteins," Genome Research 21(5):748-755, May 2011.

Waterston, R.H., et al., "Initial Sequencing and Comparative Analysis of the Mouse Genome," Nature 420(6915):520-562, Dec. 2002.

Waterston, R.H., et al., "On the Sequencing of the Human Genome," Proceedings of the National Academy of Sciences of the USA (PNAS) 99(6):3712-3716, Mar. 2002.

Wong, E., et al., "ChIP'ing the Mammalian Genome: Technical Advances and Insights Into Functional Elements," Genome Medicine 1(9):89, Sep. 2009, 10 pages.

Xu, J., "Extracting Haplotypes From Diploid Organisms," Current Issues in Molecular Biology 8(2):113-122, Jul. 2006.

Zeevi, V., et al., "Increasing Cloning Possibilities Using Artificial Zinc Finger Nucleases," Proceedings of the National Academy of Sciences of the USA (PNAS) 105(35):12785-12790, Sep. 2008.

Zeng, Y., et al., "High-Performance Single Cell Genetic Analysis Using Microfluidic Emulsion Generator Arrays," Analytical Chemistry 82(8):3183-3190, Apr. 2010.

Zerbino, D.R., et al., "Velvet: Algorithms for de Novo Short Read Assembly Using de Bruijn Graphs," Genome Research 18(5):821-829, May 2008.

Zhou, M., et al., "Molecular Genetic Analysis of Transposase—End DNA Sequence Recognition: Cooperativity of Three Adjacent Base-Pairs in Specific Interaction With a Mutant Tn5 Transposase," Journal of Molecular Biology 276(5):913-925, Mar. 1998.

Zhou, S., et al., "A Single Molecule Scaffold for the Maize Genome," PLoS Genetics 5(11):e1000711, Nov. 2009, 14 pages.

Zhou, S., et al., "Validation of Rice Genome Sequence by Optical Mapping," BMC Genomics 8(1):278, Aug. 2007, 18 pages.

Zilberman, D., and S. Henikoff, "Genome-Wide Analysis of DNA Methylation Patterns," Development 134(22):3959-3965, Nov. 2007.

Adey, A., and J. Shendure, "Ultra-Low-Input, Tagmentation-Based Whole-Genome Bisulfite Sequencing," Genome Research 22(6):1139-1142, Jun. 2012.

Adey, A., et al., "Rapid, Low-Input, Low-Bias Construction of Shotgun Fragment Libraries by High-Density in vitro Transposition," Genome Biology 11(12):R119, Dec. 2010, 17 pages.

(56) References Cited

OTHER PUBLICATIONS

Ball, M.P., et al., "Targeted and Genome-Scale Strategies Reveal Gene-Body Methylation Signatures in Human Cells," Nature Biotechnology 27(4):361-368, Apr. 2009.
Bansal, V. and V. Bafna, "HAPCUT: An Efficient and Accurate Algorithm for the Haplotype Assembly Problem," Bioinformatics 24(16):i153-i159, Aug. 2008.
Batzoglou, S., et al., "ARACHNE: A Whole-Genome Shotgun Assembler," Genome Research 12(1):177-189, Jan. 2002.
Benetti, R., et al., "A Mammalian microRNA Cluster Controls DNA Methylation and Telomere Recombination Via Rbl2-Dependent Regulation of DNA Methyltransferases," Nature Structural & Molecular Biology 15(3):268-279, 2008.
Bimber, B.N., et al., "Whole-Genome Characterization of Human and Simian Immunodeficiency Virus Intrahost Diversity by Ultradeep Pyrosequencing," Journal of Virology 84(22):12087-12092, Nov. 2010.
Bloch, C.A., et al., "Purification of *Escherichia coli* Chromosomal Segements Without Cloning," Biochemical and Biophysical Research Communications 223(1):104-111, Jun. 1996.
Branton, D., et al., "The Potential and Challenges of Nanopore Sequencing," Nature Biotechnology 26(10):1146-1153, Oct. 2008.
Braslavsky, I., et al., "Sequence Information Can Be Obtained From Single DNA Molecules," Proceedings of the National Academy of Sciences of the USA (PNAS) 100(7):3960-3964, Apr. 2003.
Brownlie, J.C., et al., "The Caenorhabditis briggsae Genome Contains Active CbmaT1 and Tcb1 Transposons," Molecular Genetics and Genomics 273(1):92-101, Mar. 2005.
Caruccio, N., "Preparation of Next-Generation Sequencing Libraries Using Nextera™ Technology: Simultaneous DNA Fragmentation and Adaptor Tagging by in vitro Transposition," Chap. 17, in Y.M. Kwon et al. (eds.), "High-Throughput Next Generation Sequencing: Methods and Applications," Methods in Molecular Biology 733:241-255, 2011.
Chernoff, A., et al., "Molecular Analysis of the von Hippel-Lindau Disesase Gene," Methods in Molecular Medicine 53:193-216, 2001.
Chinese Office Action, dated Apr. 17, 2015, issued in Chinese Application No. CN201280012945.4, filed Feb. 2, 2012, 13 pages.
Chinese Office Action, dated May 28, 2014, issued in Chinese Application No. CN201280012945.4, filed Feb. 2, 2012, 10 pages.
Clark, S.J., et al., "High Sensitivity Mapping of Methylated Cytosines," Nucleic Acids Research 22(15):2990-2997, Aug. 1994.
Cokus, S.J., et al., "Shotgun Bisulphite Sequencing of the *Arabidopsis* Genome Reveals DNA Methylation Patterning," Nature 452(7184):215-219, Mar. 2008.
Communication Pursuant to Article 94(c) EPC, dated Oct. 28, 2014, in Application No. EP11802179.9, filed Nov. 7, 2011, 12 pages.
De Vries, J.E., et al., "PCR on Cell Lysates Obtained From Whole Blood Circumvents DNA Isloation," Clinical Chemistry 47(9):1701-1702, Sep. 2001.
Deng, J., et al., "Targeted Bisulfite Sequencing Reveals Changes in DNA Methylation Associated With Nuclear Reprogramming," Nature Biotechnology 27(4):353-360, Mar. 2009.
Down, T.A., et al., "A Bayesian Deconvolution Strategy for Immunoprecipitation-Based DNA Methylome Analysis," Nature Biotechnology 26(7):779-785, Jul. 2008.
Dressman, D., et al., "Transforming Single DNA Molecules Into Fluorescent Magnetic Particles for Detection and Enumeration of Genetic Variations," Proceedings of the National Academy of Sciences of the USA (PNAS) 100(15):8817-8822, Jul. 2003.
Drmanac, R., et al., "Human Genome Sequencing Using Unchained Base Reads on Self-Assembling DNA Nanoarrays," Science 327(5961):78-81, Jan. 2010.
Duan, Z., et al., "A Three-Dimensional Model of the Yeast Genome," Nature 465(7296):363-367, May 2010.
Eid, J., et al., "Real-Time DNA Sequencing From Single Polymerase Molecules," Science 323(5910):133-138, Jan. 2009.
EP Communication Pursuant to Article 94(3) EPC, dated Oct. 26, 2015, in Application No. EP12741945.5, filed Feb. 2, 2012, 4 pages.
Extended European Search Report, dated Sep. 22, 2014, in Application No. EP12741945.5, filed Feb. 2, 2012, 7 pages.
Fan, H.C., et al., "Whole-Genome Molecular Haplotyping of Single Cells," Nature Biotechnology 29(1):51-57, Jan. 2011.
Kidd, J.M., et al., "Mapping and Sequencing of Structural Variation From Eight Human Genomes," Nature 453(7191):56-64, May 2008.
Kirby, J.R., "in vivo Mutagenesis Using EZ-Tn5™," Methods in Enzymology 421:17-21, 2007.
Kitzman, J.O., et al., "Haplotype-Resolved Genome Sequencing of a Gujarati Indian Individual," Nature Biotechnology 29(1):59-63, Jan. 2011.
Kramer, P.R., "cDNA Library Construction From Single Cells," Current Protocols in Neuroscience 19(1), Aug. 2002, 19 pages.
Lai, Z., et al., "A Shotgun Optical Map of the Entire Plasmodium falciparum Genome," Nature Genetics 23(3):309-313, Nov. 1999.
Lander, E.S., et al., "Initial Sequencing and Analysis of the Human Genome," Nature 409(6822):860-921, Feb. 2001.
Evy, S., et al., "The Diploid Genome Sequence of an Individual Human," PLoS Biology 5(10):2113-2144, Oct. 2007.
Li, H., and R. Durbin, "Fast and Accurate Short Read Alignment With Burrows-Wheeler Transform," Bioinformatics 25(14):1754-1760, Jul. 2009.
Li, R., et al., "De novo Assembly of Human Genomes With Massively Parallel Short Read Sequencing," Genome Research 20(2):265-272, Feb. 2010.
Li, Y., et al., "Primase-Based Whole Genome Amplification," Nucleic Acids Research 36(13):e79, Aug. 2008.
Li, Y., et al., "The DNA Methylome of Human Peripheral Blood Mononuclear Cells," PLoS Biology 8(11):e1000533, Nov. 2010.
Lieberman-Aiden, E., et al., "Comprehensive Mapping of Long-Range Interactions Reveals Folding Principles of the Human Genome," Science 326(5950):289-293, Oct. 2009.
Lim, A., et al., "Shotgun Optical Maps of the Whole *Escherichia coli* 0157:H7 Genome," Genome Research 11(9):1584-1593, Sep. 2001.
Lin, J., et al., "Whole-Genome Shotgun Optical Mapping of Deinococcus radiodurans," Science 285(5433):1558-1562, Sep. 1999.
Lister, R., et al., "Human DNA Methylomes at Base Resolution Show Widespread Epigenomic Differences," Nature 462(7271):315-322, Nov. 2009.
Mardis, E.R., "Next-Generation DNA Sequencing Methods," Annual Review of Genomics and Human Genetics 9:387-402, Jan. 2008.
Margulies, M., et al., "Genome Sequencing in Microfabricated High-Density Picolitre Reactors," Nature 437(7057):376-380, Sep. 2005, and Supplemental Materials.
Marine, R., et al., "Evaluation of a Transposase Protocol for Rapid Generation of Shotgun High-Throughput Sequencing Libraries From Nanogram Quantities of DNA," Applied and Environmental Microbiology 77(22):8071-8079, Nov. 2011.
Mazutis, L., et al., "Droplet-Based Microfluidic Systems for High-Throughput Single DNA Molecule Isothermal Amplification and Analysis," Analytical Chemistry 81(12):4813-4821, May 2009.
McCloskey, M.L., et al., "Encoding PCR Products With Batch-Stamps and Barcodes," Biochemical Genetics 45(11-12):761-767, Dec. 2007.
Meissner, A., et al., "Reduced Representation Bisulfite Sequencing for Comparative High-Resolution DNA Methylation Analysis," Nucleic Acids Research 33(18):5868-5877, published online Oct. 13, 2005.
Miner, B.E., et al., "Molecular Barcodes Detect Redundancy and Contamination in Hairpin-Bisulfite PCR," Nucleic Acids Research 32(17):e135, published online Sep. 30, 2004, 4 pages.
Mitra, R.D., et al., "Fluorescent in situ Sequencing on Polymerase Colonies," Analytical Biochemistry 320(1):55-65, Sep. 2003.
Mortazavi, A., et al., "Mapping and Quantifying Mammalian Transcriptomes by RNA-seq," Nature Methods 5(7):621-628, Jul. 2008.
"Nextera™ DNA Sample Prep Kits," Epicentre, <http://www.epibio.com/nextera.asp> [retrieved Dec. 13, 2012], 1 page.
Ng, S.B., et al., "Targeted Capture and Massively Parallel Sequencing of 12 Human Exomes," Nature 461(7261):272-276, Sep. 2009.

(56) References Cited

OTHER PUBLICATIONS

Numan, I.J., et al., "Mutation Discovery by Targeted Genomic Enrichment of Multiplexed Barcoded Samples," Nature Methods 7(11):913-915, Nov. 2010.
Office Action dated Mar. 27, 2012, for U.S. Appl. No. 12/559,124, filed Sep. 14, 2009, 13 pages.
Oh, J., "A Robust Platform for High-Throughput Genomics in Microorganisms," Doctoral Dissertation, Stanford University, Mar. 2010, 23 pages; pp. i, ii and 10-30.
Oh, J., et al., "A Universal TagModule Collection for Parallel Genetic Analysis of Microorganisms," Nucleic Acids Research 38(14):e146, published online May 21, 2010.
Ooka, T., et al., "Inference of the Impact of Insertion Sequence (IS) Elements on Bacterial Genome Diversification Through Analysis of Small-Size Structural Polymorphisms in Escherichia coli O157 Genomes," Genome Research 19(10):1809-1816, Oct. 2009.
Paul, P., and J. Apgar, "Single-Molecule Dilution and Multiple Displacement Amplification for Molecular Haplotyping," BioTechniques 38(4):553-559, Apr. 2005.
PCT Search Report dated Jun. 23, 2015, issued in International Application No. PCT/US2014/070658, filed Dec. 6, 2014, 8 pages.
Peck, D., et al., "A Method for High-Throughput Gene Expression Signature Analysis," Genome Biology 7(7):R61, 2006, 6 pages.
Pobigaylo, N., et al., "Construction of a Large Signature-Tagged minOTn5 Transposon Library and Its Application to Mutagenesis of Sinorhizobium meliloti," Applied and Environmental Microbiology 72(6):4329-4337, Jun. 2006.
Ramanathan, A., et al., "An Integrative Approach for the Optical Sequencing of Single DNA Molecules," Analytical Biochemistry 330(2):227-241, Jul. 2004.
Raymond, C.K., et al., "Targeted, Haplotype-Resolved Resequencing of Long Segments of Human Genome," Genomics 86(6):759-766, Dec. 2005.
Riehn, R., et al., "Restriction Mapping in Nanofluidic Devices," Proceedings of the National Academy of Sciences of the USA (PNAS) 102(29):10012-10016, Jul. 2005.
Ritz, A., et al., "Structural Variation Analysis With Strobe Reads," Bioinformatics 26(10):1291-1298, May 2010.
Schwartz, D.C., et al., "Ordered Restriction Maps of Saccharomyces cerevisiae Chromosomes Constructed by Optical Mapping," Science 262(5130):110-114, Oct. 1993.
Schwartz, J.J., et al., "Capturing Native Long-Range Contiguity by in situ Library Construction and Optical Sequencing," Proceedings of the National Academy of Sciences of the USA (PNAS) 109(46):18749-18754, Nov. 2012.
Seong, G.H., et al., "Measurement of Enzyme Kinetics Using a Continuous-Flow Microfluidic System," Analytical Chemistry 75(13):3161-3167, Jul. 2003.
Shendure, J., and H. Ji, "Next-Generation DNA Sequencing," Nature Biotechnology 26(10):1135-1145, Oct. 2008.
Shendure, J., et al., "Advanced Sequencing Technologies: Methods and Goals," Nature Reviews Genetics 5(5):335-344, May 2004.
Shendure, J., et al., "Sequence Tag Directed Subassembly of Short Sequencing Reads Into Long Sequencing Reads," U.S. Appl. No. 61/096,720, filed Sep. 12, 2008, 58 pages.
Shevchenko, Y., et al., "Systematic Sequencing of cDNA Clones Using the Transposon Tn5," Nucleic Acids Research 30(11):2469-2477, Jun. 2002.
Simon, S.A., et al., "Short-Read Sequencing Technologies for Transcriptional Analyses," Annual Review of Plant Biology 60:305-333, 2009.
Sipos, B., et al., "An Improved Protocol for Sequencing of Repetitive Genomic Regions and Structural Variations Using Mutagenesis and Next Generation Sequencing," PLoS One 7(8):e43359, published online Aug. 17, 2012.
Syed, F., et al., "Next-Generation Sequencing Library Preparation: Simultaneous Fragmentation and Tagging Using in vitro Transposition," Nature Methods 1:i-ii, Nov. 2009.
Syed, F., et al., "Optimized Library Preparation Method for Next-Generation Sequencing," Nature Methods 6(10):i-ii, Oct. 2009.
Lundquist, P.M., et al., "Parallel Confocal Detection of Single Molecules in Real Time," Opt. Lett. 33(9):1026-1028, May 2008.
Mizuuchi, K., "In Vitro Transposition of Bacteriophase Mu: A Biochemical Approach to a Novel Replication Reaction," Cell, 35:785-94, Dec. 1983.
Ohtsubo, E., and Y. Sekine, "Bacterial Insertion Sequences," Curr. Top. Microbiol. Immunol., 204:1-26, 1996.
Oroskar, A.A., et al., "Detection of Immobilized Amplicons by ELISA-Like Techniques," Clinical Chemistry 42(9):1547-1555, 1996.
Plasterk, R.H.A., "The Tc1/Mariner Transposon Family," Curr. Top. Microbiol. Immunol., 204:125-43, 1996.
Ronaghi, M., et al., "A Sequencing Method Based on Real-Time Phyrophosphate," Science, 281(5375):363-365, Jul. 1998.
Ronaghi, M., et al., "Real-time DNA Sequencing Using Detection of Pyrophosphate Release," Anal. Biochem., 242(1):84-89, Nov. 1996.
Ronaghi, M., "Pyrosequencing Sheds Light on DNA Sequencing," Genome Res., 11(1):3-11, Dec. 2001.
Savilahti, H., et al., "The Phage Mu Transpososome Core: DNA Requirements for Assembly and Function," EMBO J., 14(19):4893-4903, 1995.
Shendure, J., et al., "Accurate Multiplex Polony Sequencing of an Evolved Bacterial Genome," Science, 309:1728-1732, Sep. 2005.
Smith, S.B., et al., "Direct Mechanical Measurements of the Elasticity of Single DNA Molecules by Using Magnetic Beads," Science, 258(5085):112-1126, Nov. 1992.
Soni, G.V., and A. Meller, "Progress Toward Ultrafast DNA Sequencing Using Solid-State Nanopores," Clin. Chem., 53(11):1996-2001, 2007.
Taylor, D.M., et al., "Characterization of Chemisorbed Monolayers by Surface Potential Measurements," J. Phys. D: Appl. Phys., 24:1443-1450, 1991.
Vincent, M., et al., "Helicase-Dependent Isothermal DNA Amplification," EMBO Rep. 5(8):795-800, 2004.
Walker, G.T., et al., "A Chemiluminescent DNA Probe Test Based on Strand Displacement Amplification," Molecular Methods for Virus Detection, 329-349, 1995.
Walker, G.T., et al., "Strand Displacement Amplification—An Isothermal, In Vitro DNA Amplification Technique," Nucleic Acids Research, 20(7):1691-1696, 1992.
Wilson, A., et al., "New transposon Delivery Plasmids for Insertional Mutagenesis in Bacillus Anthracis," Journal of Microbiological Methods, 71(3):332-335, Dec. 2007.
Zhang, Z., and M.H. Saier Jr., "A Novel Mechanism of Transposon-Mediated Gene Activation," PLoS Genetics, 5(1):e1000689, Oct. 2009.
Dean, F.B., et al., "Comprehensive Human Genome Amplification Using Multiple Displacement Amplification," PNAS (Proceedings of the National Academy of Sciences of the United States of America) 99(8):5261-5266, Apr. 2002.
Ewing, B., and P. Green, "Base-Calling of Automated Sequencer Traces Using Phred. II. Error Probabilities," Genome Research 8(3):186-194, Mar. 1998.
Handelsman, J., "Metagenomics: Application of Genomics to Uncultured Microorganisms," Microbiology and Molecular Biology Reviews 68(4):669-685, Dec. 2004.
Lizardi, P.M., et al., "Mutation Detection and Single-Molecule Counting Using Isothermal Rolling-Circle Amplification," Nature Genetics 19(3):225-232, Jul. 1998.
Fullwood, M.J., et al., "An Oestrogen-Receptor-α-Bound Human Chromatin Interactome," Nature 462(7269):58-64, Nov. 2009.
Fullwood, M.J., et al., "Chromatin Interaction Analysis Using Paired-End Tag Sequencing," Current Protocols in Molecular Biology 89(1):1-25, Unit 21, Jan. 2010.
Gal, J., et al., "Directional Cloning of Native PCR Products With Preformed Sticky Ends (Autosticky PCR)," Molecular and General Genetics 260(6):569-573, Jan. 1999.
Geiss, G.K., et al., "Direct Multiplexed Measurement of Gene Expression With Colorcoded Probe Pairs," Nature Biotechnology 26(3):317-325, Mar. 2008.
Gnerre, S., et al., "High-Quality Draft Assemblies of Mammalian Genomes From Massively Parallel Sequence Data," Proceedings of

(56) References Cited

OTHER PUBLICATIONS the National Academy of Sciences of the USA (PNAS) [Epub ahead of print] PubMed PMID:21187386, Dec. 2010, pp. 1-6.
Goodman, A.L., et al., "Identifying Genetic Determinants Needed to Establish a Human Gut Symbiont in Its Habit," Cell Host & Microbe 6(3):279-289, Sep. 2009.
Grunenwald, H., et al., "Nextera PCR-Free DNA Library Preparation for Next-Generation Sequencing," Poster Presentation, AG8T, 2011.
Grunenwald, H., et al., "Rapid, High-Throughput Library Preparation for Next-Generation Sequencing," Nature Methods 7(8):iii-iv, Aug. 2010.
"GS FLX Titanium LV emPCR Kit (Lib-L)" and "GSFLX Titanium SV emPCR Kit (Lib-L)," Roche Diagnostics GmbH, Mannheim, Germany, Aug. 2008, 2 pages.
Gu, H., et al., "Preparation of Reduced Representation Bisulfite Sequencing Libraries for Genome-Scale DNA Methylation Profiling," Nature Protocols 6(4):468-481, Apr. 2011.
Harris, R.A., et al., "Comparison of Sequencing-Based Methods to Profile DNA Methylation and Identification of Monoallelic Epigenetic Modifications," Nature Biotechnology 28(10):1097-1105, Oct. 2010.
Heredia, N.J., et al., "In Vitro Double Transposition for DNA Identification," Analytical Biochemistry 399(1):78-83, Apr. 2010.
Hiatt, J.B., et al., "Tag-Directed Assembly of Locally Derived Short Sequence Reads," Nature Methods 7(2):119-122, Feb. 2010.
International Preliminary Report on Patentability dated Jul. 14, 2015, issued in International Application No. PCT/IB2014/000610, filed Jan. 8, 2014, 7 pages.
International Search Report and Written Opinion dated Apr. 10, 2012, issued in International Application No. PCT/US2011/059642, filed Nov. 7, 2011, 12 pages.
International Search Report and Written Opinion dated Aug. 24, 2012, issued in International Application No. PCT/US2012/23679, filed Feb. 2, 2012, 13 pages.
Invitation to Pay Additional Fees dated Mar. 31, 2015, issued in International Application No. PCT/US2014/070658, filed Dec. 6, 2014, 11 pages.
Jackson, A.A., and G.K. Fu, "Plasmid Tagging for Efficient Large-Scale Sequence Completion of Entire Clone Inserts," BioTechniques 34(3):604-608, Mar. 2003.
Johnson, D.S., et al., "Genome-Wide Mapping of in Vivo Protein-DNA Interactions," Science 316(5830):1497-1502, Jun. 2007.
Japanese Office Action dated Jan. 12, 2016, issued in Japanese Application No. JP2013-552641, filed Feb. 2, 2012, 7 pages.
Keith, J.M., et al., "Algorithms for Sequence Analysis via Mutagenesis," Bioinformatics 20(15)12401-2410; published online May 14, 2004.
Keith, J.M., et al., "Unlocking Hidden Genomic Sequence," Nucleic Acids Research 32(3):e35; published online Feb. 18, 2004.
International Search Report dated Jun. 23, 2015, issued in International Application No. PCT/US2014/070658, filed Dec. 6, 2014, 9 pages.
Bains, W., and G. Smith, "A Novel Method for Nucleic Acid Sequence Determination," J. Theor. Biol., 135(3):303-307, 1998.
Bentley, D., et al., "Accurate Whole Human Genome Sequencing Using Reversible Terminator Chemistry," Nature, 456(7218):53-59, Nov. 2008.
Boeke, J., and V. Corces, "Transcription and Reverse Transcription of Retrotransposons," Annu. Rev. Microbiol. 43:403-435, 1989.
Brown, P., et al., "Retroviral Integration: Structure of the Initial Covalent Product and Its Precursor, and a Role for the Viral IN Protein," Proc. Natl. Acad. Sci. USA, 86:2525-2529, Apr. 1989.

Cockroft, S., et al., "A Single-Molecule Nanopore Device Detects DNA Polymerase Activity With Single-Nucleotide Resolution," J. Am. Chem. Soc, 130(3): 818-820, 2008.
Colegio, O., et al., "In Vitro Transposition System for Efficient Generation of Random Mutants of Campylobacter Jejuni," Journal of Bacteriology, 183(7):2384-2388, Apr. 2001.
Craig, N.L., "Transposon Tn7," Review in: Curr. Top. Microbiol. Immunol., 204:27-48, 1996.
Craig, N.L., "V(D)J Recombination and Transposition: Closer Than Expected," Science, 271(52555):1512, Mar. 1996.
Deamer, D., and D. Branton, "Characterization of Nucleic Acids by Nanopore Analysis," Acc. Chem. Res., 35(10):817-825, 2002.
Deamer, D., and M. Aekson, "Nanopores and Nucleic Acids: Prospects for Ultrarapid Sequencing," Trends Biotechnol, 18(4):147-151, Apr. 2000.
Drmanac, S., et al., "Accurate Sequencing by Hybridization for DNA Diagnostics and Individual Genomics," Nature Biotechnology, 16(1):54-58, Jan. 1998.
Duitama, J., et al., "ReFHap: A Reliable and Fast Algorithm for Single Invididual Haplotyping," Proceedings of the First ACM International Conference on Bioinformatics and Computational Biology, 160-169, 2010.
Fodor, S.P.A., et al., "Light-Directed, Spatially Addressable Parallel Chemical Synthesis," Science, 251(4995):767-773, Feb. 1991.
Gloor, G., "Gene Targeting in *Drosophila*," Methods in Molecular Biology, 260:97-114, 2004.
Goryshin, I.Y., and Reznikoff, W. S., "Tn5 In Vitro Transposition," J. Biol. Chem., 273 (13):7367-7374, 1988.
Haapa, S., et al., "An Efficient and Accurate Integration of Mini-Mu Transposons In Vitro: A General Methodology for Functional Genetic Analysis and Molecular Biology Applications," Nucleic Acids Research, 27(13):2777-2784, 1999.
Healy, K., "Nanopore-Based Single-Molecule DNA Analysis," Nanomed. 2(4):456-481, 2007.
Ichikawa, H., and E. Ohtsubo, "In Vitro Transposition of Transposon Tn3," J. Biol. Chem., 265(31):18829-18832, Nov. 1990.
Joos, B., et al., "Covalent Attachment of Hybridizable Oligonucleotides to Glass Supports," Analytical Biochemistry, 247: 96-101, 1997.
Khandjian, E.W., "UV Crosslinking of RNA to Nylon Membrane Enhances Hybridization Signals," Molec. Biol. Rep., 11:107-115, 1986.
Kirby, C., et al., "Cryptic Plasmids of *Mycobacterium avium*L Tn552 to the Rescue," Molecular Microbiology, 43(1):173-186, 2002.
Kleckner, N., et al., "Tn10 and IS10 Transposition and Chromosome Rearrangements: Mechanism and Regulation In Vivo and In Vitro," Curr. Top. Microbiol. Immunol., 204:49-82, 1996.
Korlach, J., et al., "Selective Aluminum Passivation for Targeted Immobilization of Single DNA Polymerase Molecules in Zero-Mode Waveguide Nanostructures," PNAS, 105(4):1176-1181, Jan. 2008.
Lage, J.M., et al., "Whole Genome Analysis of Genetic Alterations in Small DNA Samples Using Hyperbranched Strand Displacement Amplification and Array-CGH," Genome Research, 13(2):294-307, Feb. 2003.
Lampe, D., et al., "A Purified Mariner Transposase is Sufficient to Mediate Transposition In Vitro", EMBO J., 15(19):5470-5479, 1996.
Levene, M.J., et al., "Zero-Mode Waveguides for Single-Molecule Analysis at High Concentrations," Science 299:682-686, Jan. 2003.
Li, J., et al., "DNA Molecules and Configurations in a Solid-State Nanopore Microscope," Nature Materials, 2(9):611-615, Sep. 2003.

SEQUENCE LISTING

```
<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
tcgcaataca gagtttaccg catt                                            24

<210> SEQ ID NO 2
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Wherein N is a five prime phosphate
      modification of A

<400> SEQUENCE: 2
ntgcggtaaa ctctgtattg cga                                             23

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ctcttccgca tctcacaacc tact                                            24

<210> SEQ ID NO 4
<211> LENGTH: 23
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Wherein N is a five prime phosphate
      modification of G

<400> SEQUENCE: 4
ntaggttgtg agatgcggaa gag                                            23

<210> SEQ ID NO 5
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Wherein N is a five prime phosphate
      modification of T

<400> SEQUENCE: 5
ncgcaataca gagtttaccg catt                                           24

<210> SEQ ID NO 6
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Wherein N is a five prime phosphate
      modification of C

<400> SEQUENCE: 6
ntcttccgca tctcacaacc tact                                           24

<210> SEQ ID NO 7
<211> LENGTH: 62
<212> TYPE: DNA
<213> ORGANISM: Artificial Sequence
<220> FEATURE:
<223> OTHER INFORMATION: Synthetic

<400> SEQUENCE: 7
aatgatacgg cgaccaccga gatctacacc aatggagctc gcaatacaga gtttaccgca    60
tt                                                                   62

<210> SEQ ID NO 8
<211> LENGTH: 57
<212> TYPE: DNA
<213> ORGANISM: Artificial Sequence
<220> FEATURE:
<223> OTHER INFORMATION: Synthetic

<400> SEQUENCE: 8
caagcagaag acggcatacg agatatcgag agcctcttcc gcatctcaca acctact       57

<210> SEQ ID NO 9
<211> LENGTH: 33
<212> TYPE: DNA
<213> ORGANISM: Artificial Sequence
<220> FEATURE:
<223> OTHER INFORMATION: Synthetic
```

```
<400> SEQUENCE: 9
caatggagct cgcaatacag agtttaccgc att                           33

<210> SEQ ID NO 10
<211> LENGTH: 33
<212> TYPE: DNA
<213> ORGANISM: Artificial Sequence
<220> FEATURE:
<223> OTHER INFORMATION: Synthetic

<400> SEQUENCE: 10
atcgagagcc tcttccgcat ctcacaacct act                           33

<210> SEQ ID NO 11
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Wherein N is a phophorothiate bond of T

<400> SEQUENCE: 11
ctcggcattc ctgctgaacc gctcttccga tcn                           33

<210> SEQ ID NO 12
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Wherein N is a five prime phosphate
      modification of G

<400> SEQUENCE: 12
natcggaaga gcggttcagc aggaatgccg ag                            32

<210> SEQ ID NO 13
<211> LENGTH: 61
<212> TYPE: DNA
<213> ORGANISM: Artificial Sequence
<220> FEATURE:
<223> OTHER INFORMATION: Synthetic

<400> SEQUENCE: 13
caagcagaag acggcatacg agatcggtct cggcattcct gctgaaccgc tcttccgatc    60
t                                                                   61

<210> SEQ ID NO 14
<211> LENGTH: 62
<212> TYPE: DNA
<213> ORGANISM: Artificial Sequence
<220> FEATURE:
<223> OTHER INFORMATION: Synthetic

<400> SEQUENCE: 14
aatgatacgg cgaccaccga gatctacaca tcgagagcct cttccgcatc tcacaaccta    60
ct                                                                  62
```

```
<210> SEQ ID NO 15
<211> LENGTH: 37
<212> TYPE: DNA
<213> ORGANISM: Artificial Sequence
<220> FEATURE:
<223> OTHER INFORMATION: Synthetic

<400> SEQUENCE: 15
cggtctcggc attcctgctg aaccgctctt ccgatct                              37
```

ERROR DETECTION IN SEQUENCE TAG DIRECTED SEQUENCING READS

CROSS-REFERENCES TO RELATED APPLICATIONS

This application is a continuation of U.S. application Ser. No. 15/594,476, filed May 12, 2017, now U.S. Pat. No. 10,577,601, which is a continuation of U.S. application Ser. No. 15/148,928, filed May 6, 2016, now U.S. Pat. No. 10,227,585, which is a continuation of U.S. application Ser. No. 14/479,122, filed Sep. 5, 2014, which is a continuation of U.S. application Ser. No. 13/759,292, filed Feb. 5, 2013, now U.S. Pat. No. 8,846,347, which is a continuation of U.S. application Ser. No. 12/559,124, filed Sep. 14, 2009, now U.S. Pat. No. 8,383,345, which claims the benefit of U.S. Provisional Application No. 61/096,720, filed Sep. 12, 2008, each of which is expressly incorporated by reference herein in its entirety.

STATEMENT REGARDING SEQUENCE LISTING

The sequence listing associated with this application is provided in text format in lieu of a paper copy and is hereby incorporated by reference into the specification. The name of the text file containing the sequence listing is UWOTL171175_Sequence_final_2017-05-11_ST25.txt. The text file is 5 KB; was created on May 11, 2017; and is being submitted via EFS-Web with the filing of the specification.

BACKGROUND

Massively parallel DNA sequencing platforms have recently become broadly available (see, for example, Mardis, E. R., "The Impact of Next-Generation Sequencing Technology on Genetics," *Trends Genet.* 24:133-141 (2008), and Wold, B., et al., "Sequence Census Methods for Functional Genomics," *Nat. Methods* 5:19-21 (2008)). Several platforms operate at a fraction of the per-base costs of conventional electrophoretic sequencing, but produce sequence reads that are over an order of magnitude shorter and less accurate. These short reads have information content such that most are uniquely mappable to genomes with an existing reference assembly, enabling a variety of "sequence census" applications (see Wold, B. and Myers, R. M., "Sequence Census Methods for Functional Genomics," *Nat. Methods* 5:19-21 (2008)). However, the short lengths and high error rates impose significant limitations on the utility of short reads for applications such as de novo genome assembly, full length cDNA sequencing, metagenomics, and the interrogation of non-unique subsequences of assembled genomes. Towards addressing these limitations, this invention provides methods and compositions that enable the clustering of short reads derived from the same kilobase-scale fragments. Each cluster of short reads can then be locally assembled in silico into a single long read or a mate-pair of long reads, which are referred to as "subassemblies."

SUMMARY

This summary is provided to introduce a selection of concepts in a simplified form that are further described below in the Detailed Description. This summary is not intended to identify key features of the claimed subject matter nor is it intended to be used as an aid in determining the scope of the claimed subject matter.

In general, the invention relates to methods for preparing a library of DNA molecules, wherein the resulting library is useful for determining the nucleotide sequence of kilobase-scale DNA molecules. In particular, the methods of the invention are useful for assembling short reads of nucleotide sequence into longer reads of nucleotide sequence, allowing the sequence of kilobase-scale DNA fragments to be assembled.

In one aspect, the invention provides a method for preparing a DNA sequencing library, the method comprising the following steps:

(a) circularizing a target fragment library with a plurality of adaptor molecules to produce a population of circularized double-stranded DNA molecules, wherein the plurality of adaptor molecules comprises a first defined sequence P1, a degenerate sequence tag, and a second defined sequence P2, such that at least one circularized double-stranded DNA molecule comprises a non-degenerate sequence tag and a member of the target fragment library;

(b) amplifying the population of circularized double-stranded DNA molecules to produce a plurality of copies of each circularized double-stranded DNA molecule, wherein the copies of each circularized double-stranded DNA molecule comprise the same non-degenerate sequence tag;

(c) fragmenting the plurality of copies of each circularized double-stranded DNA molecule to produce a plurality of linear double-stranded DNA molecules, wherein the plurality of linear double-stranded DNA molecules may be the same or different, and at least one of the plurality of linear double-stranded DNA molecules contains the non-degenerate sequence tag present in the plurality of copies of each circularized double-stranded DNA molecule;

(d) adding a third defined sequence P3 to at least one of a first end and a second end of at least one of the plurality of linear double-stranded DNA molecules from step (c); and (e) amplifying a region of at least one of the plurality of linear double-stranded DNA molecules to produce a plurality of amplicons, wherein at least one amplicon comprises the non-degenerate sequence tag and sequence complementary to a portion of a single member of the target fragment library.

In a second aspect, the invention provides a method for preparing a DNA sequencing library comprising the following steps:

(a) circularizing a target fragment library with a plurality of adaptor molecules to produce a population of first circularized double-stranded DNA molecules, wherein the plurality of adaptor molecules comprises a first defined sequence P1 comprising a first restriction enzyme recognition site R1, a degenerate sequence tag, and a second defined sequence P2 comprising a second restriction enzyme recognition site R2, such that at least one of the first circularized double-stranded DNA molecule comprises a non-degenerate sequence tag and a member of the target fragment library;

(b) amplifying the population of first circularized double-stranded DNA molecules to produce a plurality of copies of each first circularized double-stranded DNA molecule, wherein the copies of each first circularized double-stranded DNA molecule comprise the same non-degenerate sequence tag;

(c) fragmenting the plurality of copies of each first circularized double-stranded DNA molecule to produce a plurality of first linear double-stranded DNA molecules, wherein the plurality of first linear double-stranded DNA molecules may be the same or different, and at least one of the plurality of first linear double-stranded DNA molecules contains the non-degenerate sequence tag present in the plurality of copies of each first circularized double-stranded DNA molecule;

(d) adding a third defined sequence P3 to at least one of a first end and a second end of at least one of the plurality of first linear double-stranded DNA molecules from step (c);

(e) digesting at least one of the first linear double-stranded DNA molecules from step (d) with restriction enzyme R1, thereby producing an R1 digested double-stranded DNA molecule;

(f) circularizing the R1 digested double-stranded DNA molecule with a first bridging oligonucleotide B1 to generate a second circularized double-stranded DNA molecule;

(g) amplifying the second circularized double-stranded DNA molecule of step (f) to produce a plurality of copies of the second circularized double-stranded DNA molecule;

(h) fragmenting the plurality of copies of the second circularized double-stranded DNA molecule to produce a plurality of second linear double-stranded DNA molecules, wherein at least one of the plurality of second linear double-stranded DNA molecules contains the non-degenerate sequence tag present in the plurality of copies of the second circularized double-stranded DNA molecule;

(i) adding a fourth defined sequence P4 to at least one of a first end and a second end of at least one of the plurality of second linear double-stranded DNA molecules; and (j) amplifying a region of at least one of the plurality of second linear double-stranded DNA molecules to produce a plurality of amplicons, wherein each amplicon comprises the non-degenerate sequence tag and sequence complementary to a portion of a single member of the target fragment library.

In a related aspect, the method comprises the following additional steps:

(i) digesting at least one of the first linear double-stranded DNA molecules having a third defined sequence P3 added to at least one of a first end and a second end with restriction enzyme R2, thereby producing an R2 digested double-stranded DNA molecule;

(ii) circularizing the R2 digested double-stranded DNA molecule with a second bridging oligonucleotide B2 to generate a third circularized double-stranded DNA molecule;

(iii) amplifying the third circularized double-stranded DNA molecule to produce a plurality of copies of the third circularized double-stranded DNA molecule;

(iv) fragmenting the plurality of copies of the third circularized double-stranded DNA molecule to produce a plurality of third linear double-stranded DNA molecules, wherein at least one of the plurality of third linear double-stranded DNA molecules contains the non-degenerate sequence tag present in the plurality of copies of the third circularized double-stranded DNA molecule;

(v) adding a fifth defined sequence P5 to at least one of a first end and a second end of at least one of the plurality of third linear double-stranded DNA molecules; and (vi) amplifying a region of at least one of the plurality of third linear double-stranded DNA molecules to produce a plurality of amplicons comprising the sequence tag, wherein each amplicon comprises the non-degenerate sequence tag and sequence complementary to a portion of a single member of the target fragment library.

In a third aspect, the invention provides a method for preparing a DNA sequencing library that involves cloning a kilobase-scale target fragment library into a vector having restriction enzyme recognition sites flanking the cloned insert, wherein the cognate restriction enzymes that bind to the recognition sites digest the insert DNA such that a portion of each end of the insert DNA remains attached to the vector after digestion. The end portions of the insert are then sequenced to provide a sequence tag that is useful for assembling microsequencing reads into longer contiguous sequences (contigs), referred to herein as subassemblies. According to this aspect of the invention, the end portion sequences are assembled with sequences from internal portions of the kilobase-scale insert. The method provides sequencing templates for generating sequencing reads that can be subassembled into longer contigs and comprises the following steps:

(a) providing a population of circular double-stranded DNA molecules; wherein each circular double-stranded DNA molecule comprises a sequence of interest having a first end joined to the first end of a vector sequence, an internal portion, and a second end joined to the second end of the vector sequence;

(b) fragmenting a portion of the population of circular double-stranded DNA molecules to produce a plurality of linear double-stranded DNA molecules;

(c) adding a common adaptor sequence to at least one end of at least one of the plurality of linear double-stranded DNA molecules; and (d) amplifying a region of at least one of the plurality of linear double-stranded DNA molecules to produce a plurality of amplicons, wherein at least one amplicon comprises sequence complementary to the sequence of interest.

According to this aspect of the invention, the plurality of amplicons are sequenced, producing a pair, or at least two, associated sequences per amplicon, wherein the associated sequences comprise a first sequence from an end portion of the insert sequence and a second sequence from an internal portion of the insert. The location of the internal sequence is determined by the fragmentation breakpoint from step (b) above. The plurality of associated sequences is assembled into subassemblies, wherein sequences that are complementary to an internal portion of the insert sequence are assembled if they are associated with the same sequence that is complementary to an end portion of the insert. This results in subassemblies from both ends of an insert sequence. In order to associate subassemblies from each end of an insert sequence with each other, this aspect of the method provides the following additional steps:

(i) digesting a portion of the population of circular double-stranded DNA molecules from step (a) above with at least one restriction enzyme; and (ii) recircularizing at least one of the digested double-stranded DNA molecules.

According to this aspect of the invention, the recircularized DNA molecules are sequenced using primers that anneal to the vector sequence, thereby producing sequencing reads corresponding to both ends of the insert sequence. Because the end sequences from both ends of the same insert are now known, the subassemblies from each end of an insert sequence of interest can be associated with each other, allowing the subassemblies to be assembled into larger contigs comprising the sequence of interest.

In a fourth aspect, the invention provides a method for preparing a DNA sequencing library entirely in vitro that does not require circularization of nucleic acid fragments or cloning of fragments into a vector. The method of this aspect of the invention comprises the following steps:

(a) incorporating at least one first nucleic acid adaptor molecule into at least one member of a target library comprising a plurality of nucleic acid molecules, wherein at least a portion of the first adaptor molecule comprises a first defined sequence;

(b) amplifying the plurality of nucleic acid molecules to produce an input library comprising a first plurality of amplified DNA molecules, wherein the amplified molecules comprise sequence identical to or complementary to at least a portion of the first adaptor molecule and sequence identical to or complementary to at least a portion of at least one member of the target library;

(c) fragmenting the input library to produce a plurality of linear DNA fragments having a first end and a second end;

(d) attaching at least one second nucleic acid adaptor molecule to one or both ends of at least one of the plurality of linear DNA fragments, wherein at least a portion of the second adaptor molecule comprises a second defined sequence;

(e) amplifying the plurality of linear DNA fragments to produce a sequencing library comprising a second plurality of amplified DNA molecules, wherein at least one of the plurality of amplified DNA molecules comprises sequence identical to or complementary to at least a portion of the first adaptor molecule, sequence identical to or complementary to at least a portion of the second adaptor molecule, and sequence identical to or complementary to at least a portion of a member of the target library.

In another aspect, the invention provides a kit for preparing a DNA sequencing library, the kit comprising a mixture of double-stranded, partially degenerate adaptor molecules, wherein each adaptor molecule comprises a first defined sequence P1, a sequence tag that is fully or partially degenerate within the mixture of adaptor molecules, and a second defined sequence P2, wherein the degenerate sequence tag comprises from 5 to 50 randomly selected nucleotides. In another aspect, the invention provides a kit comprising a vector modified with restriction enzyme recognition sites that are useful for digesting a cloned sequence of interest, such that a portion of each end of the cloned insert DNA remains attached to the vector after digestion. In yet another aspect, the invention provides a kit comprising at least one of a plurality of first nucleic acid adaptor molecules, and at least one of a plurality of second nucleic acid adaptor molecules.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
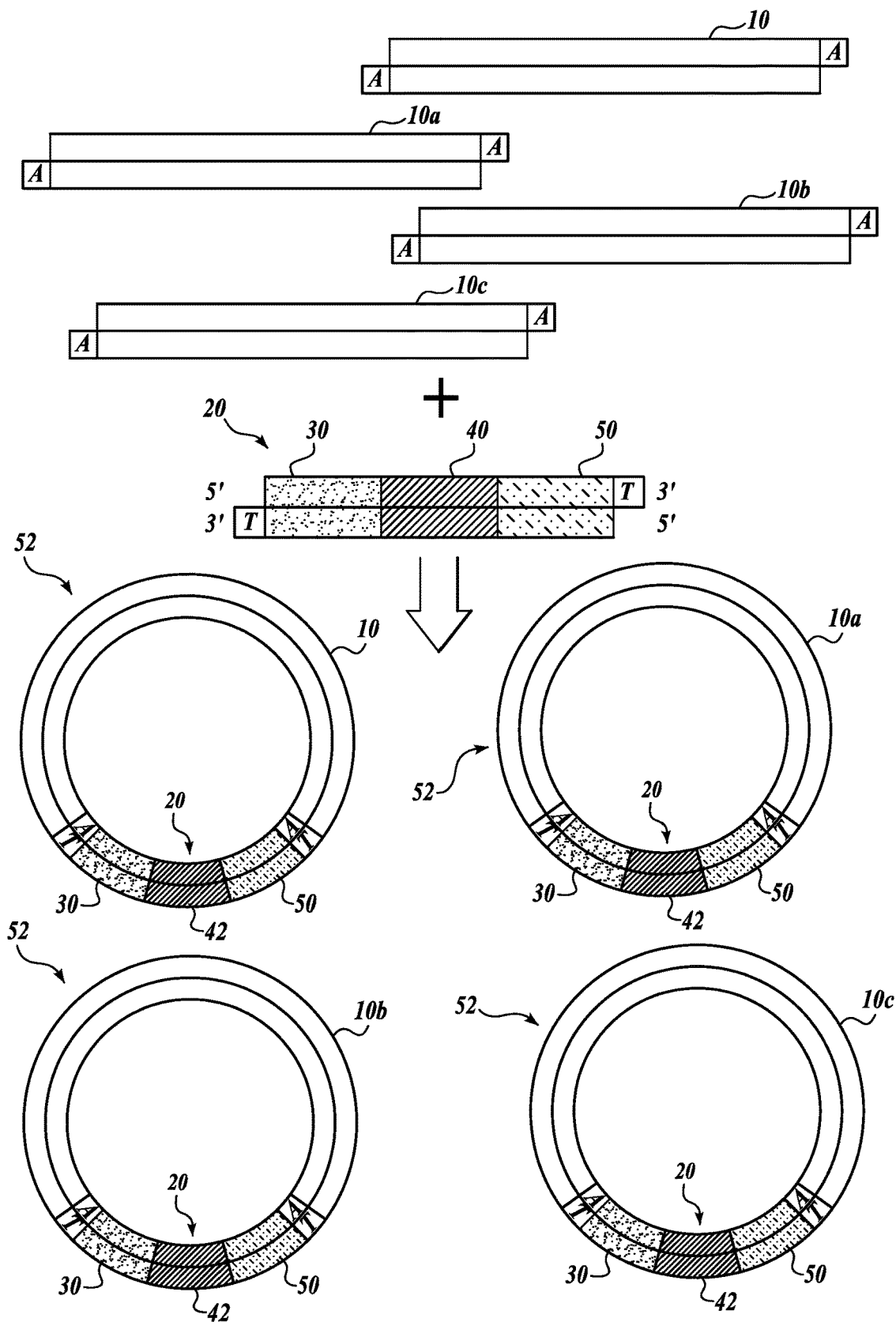
FIG. 1 shows a schematic illustration of a representative embodiment of the invention, illustrating the circularization of a plurality of target DNA fragments with a degenerate adaptor sequence tag, thereby producing a plurality of circular DNA molecules having non-degenerate sequence tags, as described in Example 1.

In one aspect, the present invention provides methods for preparing a DNA sequencing library. The methods of the invention are useful for the clustering of micro-sequencing reads derived from the same kilobase-scale DNA fragment. Each cluster of microreads is assembled into a single long read or an associated pair of long reads, which are termed subassemblies. In the context of massively parallel sequencing, the subassembly of microreads derived from the same kilobase-scale region can be assembled de novo, which has computational advantages over direct de novo assembly of microreads, for example, into a full genome sequence.

Unless defined otherwise, all technical and scientific terms used herein have the meaning commonly understood by one of ordinary skill in the art to which this invention belongs. Practitioners are particularly directed to Sambrook, J., and Russell, D. W., eds., *Molecular Cloning: A Laboratory Manual*, 3rd ed., Cold Spring Harbor Laboratory Press, Cold Spring Harbor, N.Y. (2001), and Ausubel, F. M., et al., *Current Protocols in Molecular Biology* (Supplement 47), John Wiley & Sons, New York (1999), which are incorporated herein by reference, for definitions and terms of the art.

In one embodiment, the method for preparing a DNA sequencing library includes the following steps:

(a) circularizing a target fragment library with a plurality of adaptor molecules to produce a population of circularized double-stranded DNA molecules, wherein the plurality of adaptor molecules comprises a first defined sequence P1, a degenerate sequence tag, and a second defined sequence P2, such that at least one circularized double-stranded DNA molecule comprises a non-degenerate sequence tag and a member of the target fragment library;

(b) amplifying the population of circularized double-stranded DNA molecules to produce a plurality of copies of each circularized double-stranded DNA molecule, wherein the copies of each circularized double-stranded DNA molecule comprise the same non-degenerate sequence tag;

c) fragmenting the plurality of copies of each circularized double-stranded DNA molecule to produce a plurality of linear double-stranded DNA molecules, wherein the plurality of linear double-stranded DNA molecules may be the same or different, and at least one of the plurality of linear double-stranded DNA molecules contains the non-degenerate sequence tag present in the plurality of copies of each circularized double-stranded DNA molecule;

(d) adding a third defined sequence P3 to at least one of a first end and a second end of at least one of the plurality of linear double-stranded DNA molecules from step (c); and (e) amplifying a region of at least one of the plurality of linear double-stranded DNA molecules to produce a plurality of amplicons, wherein at least one amplicon comprises the non-degenerate sequence tag and sequence complementary to a portion of a single member of the target fragment library.

In the method, a target fragment library of linear DNA molecules is circularized with a plurality of adaptor molecules. As used herein, the term "target fragment" refers to a DNA molecule comprising a sequence of interest. As used herein, the term "library" refers to a population of DNA molecules, wherein each member of the population may be the same or different. In one embodiment, the target fragment library is composed of genomic DNA that is randomly fragmented and size-selected to a defined kilobase-scale range, for example, 0.3 to 10 kilobases in length. However, the method can be performed using a DNA library derived from any source, for example, a cDNA library that is generated from RNA isolated from a biological sample. In some embodiments, the target fragment library is isolated from a eukaryotic organism, which includes all organisms with a nucleus in their cells, for example, animals, plants, fungi, and protists. In other embodiments, the target fragment library is isolated from a prokaryotic organism, such as a bacterium. In one embodiment, the target fragment library is derived from DNA or RNA isolated from a virus.

FIG. 1 illustrates a representative embodiment of the method. Referring to FIG. 1, a plurality of double-stranded DNA fragments 10, 10a, 10b, 10c is circularized with a plurality of adaptor molecules 20, thereby generating a population of circular molecules 52 that contain a DNA fragment 10 and an adaptor molecule 20. In some embodiments the method produces a population of circularized double-stranded DNA molecules 52, wherein each circular DNA molecule comprises a different sequence tag 42. In one embodiment illustrated in FIG. 1, the DNA fragments of the library are end-repaired and tailed with deoxyadenosine (A-tailed) at the 3' ends of the fragment, using methods well known in the art.

The adaptor molecule 20 comprises a first defined sequence 30 (also referred to herein as P1), a degenerate sequence tag 40, and a second defined sequence 50 (also referred to herein as P2). In some embodiments, the adaptor molecule 20 is 35 base-pairs (bp) to 150 bp in length. In one embodiment shown in FIG. 1, the defined sequences 30 and 50 flank the sequence tag 40. In some embodiments, the defined sequences P1 and P2 are the same sequence in every adaptor molecule and are referred to herein as common defined sequences. The defined sequences P1 and P2 can be any nucleotide sequence and, in some embodiments, are 15 bp to 50 bp in length. In some embodiments, the P1 and P2 sequences are selected based on the desired properties of oligonucleotide primers that will anneal to the sense or antisense strand of the P1 and P2 sequence. Primers that anneal to the P1 and P2 sequences are useful for amplifying subregions of the DNA fragment, for example, by the polymerase chain reaction (PCR), as described below. In one embodiment, defined sequence P1 comprises a restriction enzyme (RE) recognition site. In another embodiment, defined sequence P2 comprises an RE recognition site.

In one embodiment, the degenerate sequence tag 40 is a randomly selected nucleotide sequence 5 to 50 nucleotides in length. It will be appreciated that a sequence is degenerate in the context of a plurality of adaptor molecules, whereas each individual adaptor molecule potentially comprises a non-degenerate sequence tag 42. Therefore, if the number of circularized double-stranded DNA molecules is less than the number of possible degenerate sequences, each circularized double-stranded DNA molecule potentially contains a unique non-degenerate sequence tag 42.

Referring again to FIG. 1, in some embodiments, the adaptor molecule 20 is tailed with deoxythymidine (T-tailed) at the 3' ends using methods well known in the art. In this embodiment, the A-tailed DNA fragments are ligated to the T-tailed adaptor molecules, thereby generating circularized double-stranded DNA molecules. DNA fragments that are not circularized with an adaptor molecule may be degraded by digestion with exonuclease.

After the target fragment library is circularized with the plurality of adaptor molecules, the population of circularized double-stranded DNA molecules are amplified to produce one or more copies of each circularized double-stranded DNA molecule. In one embodiment, the circularized double-stranded DNA molecules are amplified using isothermal rolling circle amplification, as described in Lizardi, P. M., et al., "Mutation Detection and Single-Molecule Counting Using Isothermal Rolling-Circle Amplification," *Nat. Genet* 19(3):225-232, July 1998. In another embodiment, the circularized double-stranded DNA molecules are amplified by multiple displacement amplification, as described in Dean, F. B., et al., "Comprehensive Human Genome Amplification Using Multiple Displacement Amplification," *PNAS* 99(8): 5261-5266, April 2002.

Figure 2:
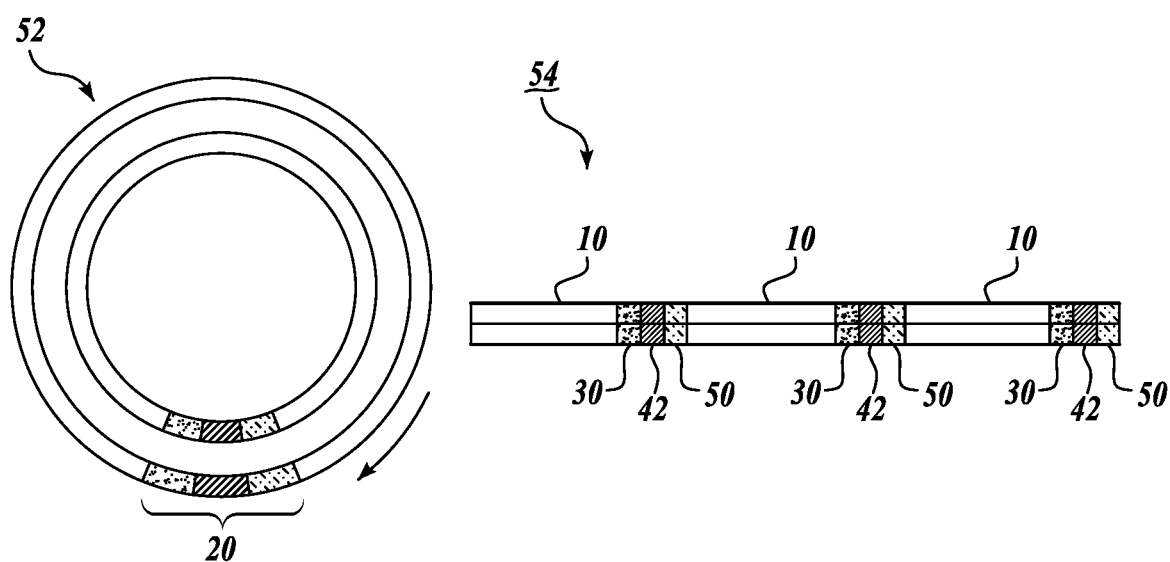
FIG. 2 schematically illustrates the isothermal amplification of a circularized DNA molecule shown in FIG. 1 to produce a plurality of copies comprising the target fragment and a non-degenerate sequence tag, in accordance with an embodiment of the invention.

FIG. 2 illustrates one representative embodiment of this step of the method. As shown in FIG. 2, the amplification step may produce concatemerized copies 54 of each circularized DNA molecule. The copies 54 of each circularized DNA molecule contain the same non-degenerate sequence tag 42. By "same non-degenerate sequence tag," it is understood that each circularized DNA molecule 52 contains a potentially unique non-degenerate sequence tag 42 and that amplification produces one or more copies of at least one circularized DNA molecule, wherein each copy contains the same non-degenerate sequence tag that was present in the parent circularized DNA molecule 52. As used herein, the term "each" includes one or more.

Figure 3:
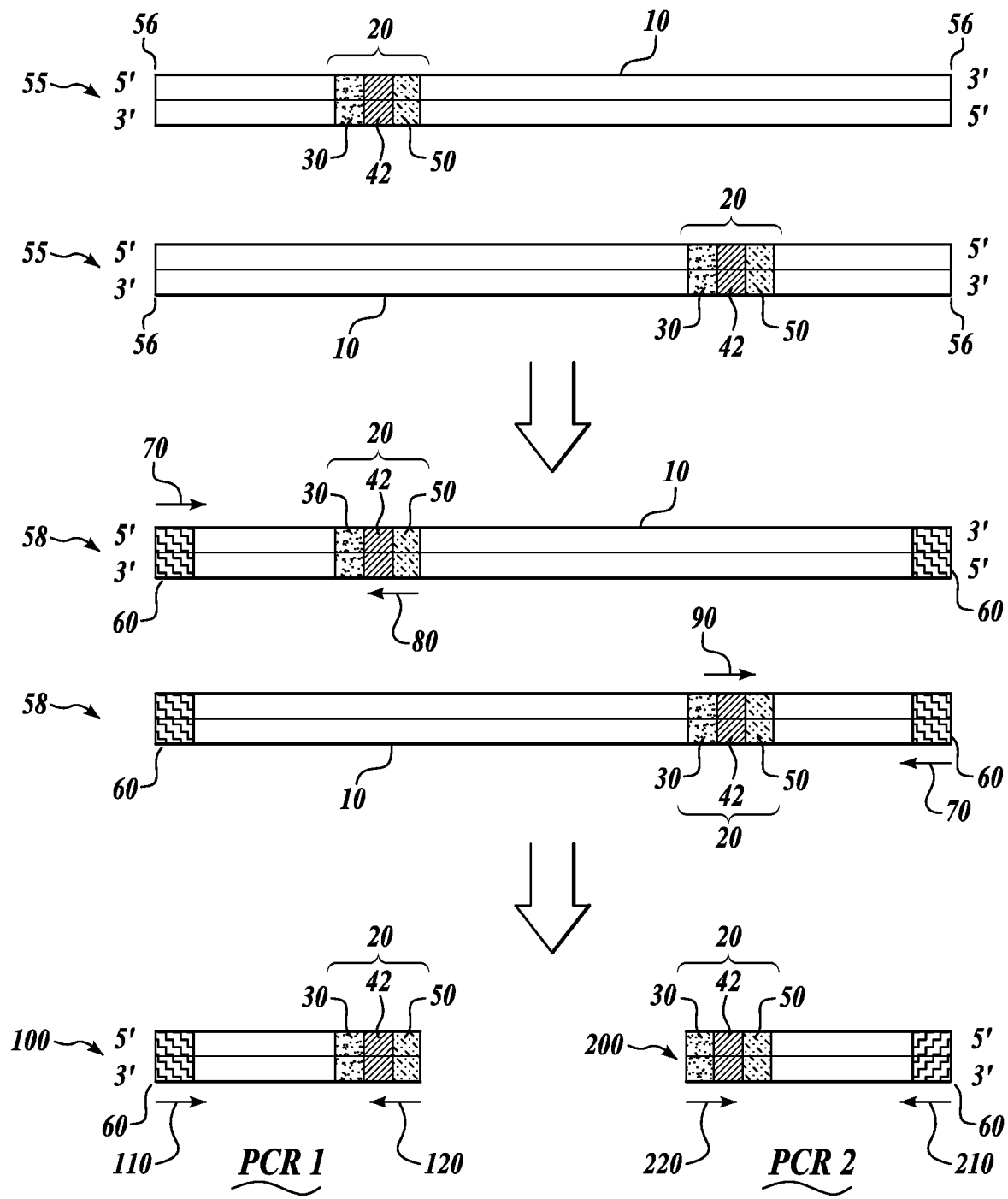
FIG. 3 schematically illustrates additional steps of one embodiment of the invention, wherein copies of a circularized DNA molecule comprising the target fragment and a non-degenerate sequence tag, as shown in FIG. 2, are fragmented to produce linear DNA fragments, a common adaptor sequence is added to one or both ends of each fragment, a region of each fragment is amplified by PCR, and the amplified products are sequenced.

Following amplification, the copies 54 of each circularized double-stranded DNA molecule are fragmented to produce a plurality of linear double-stranded DNA molecules. After fragmentation, at least one, and preferably many, of the linear double-stranded DNA molecules contain the same non-degenerate sequence tag 42 present in the parent circularized DNA molecule 52 that was amplified in the previous step. In one embodiment, fragmentation is accomplished by nebulization, as described in Sambrook and Russell (2001). In another embodiment, fragmentation is accomplished by sonication, as described in Sambrook and Russell (2001). A representative example of this step of the method is illustrated in FIG. 3. The fragmentation breakpoints 56 are essentially random, generating linear double-stranded DNA molecules 55 wherein the adaptor sequence 20 is located at various distances from the ends 56 of the linear double-stranded DNA molecules 55. Note that because of the essentially random fragmentation process, some fragments may not contain the adaptor sequence (not shown); these fragments will not be useful in the following steps of the method and will not be described further. In one embodiment, the DNA fragments are end-repaired and A-tailed. Referring again to FIG. 3, in some embodiments a third defined adaptor sequence 60, referred to herein as P3, is added to one or both ends of at least one of the plurality of linear double-stranded DNA molecules 55. In one embodiment shown in FIG. 3, a plurality of linear double-stranded DNA molecules 58 comprises the P3 sequence 60 at both ends of the molecule. The P3 sequence may be any nucleotide sequence. In one embodiment, the P3 sequence is 15 bp to 50 bp in length. In one embodiment, the P3 sequence is T-tailed to facilitate ligation to the A-tailed DNA fragments. In one embodiment, the P3 sequence is designed as a binding site for oligonucleotide primers that are useful for amplifying a region of the linear double-stranded DNA molecule, for example, by PCR. In some embodiments, the P3 sequence added to one end of at least one of the plurality of linear double-stranded DNA molecules is the same or different than the P3 sequence added to the other end of the linear double-stranded DNA molecules. It is appreciated that, in the practice of the method, a P3 sequence may not be added to one or both ends of every linear double-stranded DNA molecule in the plurality of linear double-stranded DNA molecules.

In the methods, one or more regions of the plurality of linear double-stranded DNA molecules may be amplified to facilitate sequencing the nucleotides in the target DNA fragment. In one embodiment, the region of interest is amplified by PCR. In another embodiment, multi-template PCR is performed to amplify a plurality of regions in parallel, thereby producing a plurality of PCR products. As used herein, another term for PCR product is "amplicon." In one embodiment, one or more amplicons in the plurality of amplicons has one end comprising sequence that corresponds to a fragmentation breakpoint internal to a target fragment and another end comprising sequence that corresponds to the non-degenerate tag sequence circularized with the target fragment. As used herein, a nucleotide sequence "corresponds" to another nucleotide sequence if it comprises a sequence that is identical to, or complementary to, all or part of the other sequence. As used herein, the term "complementary" includes nucleotide sequence that is at least 60%, at least 70%, at least 80%, at least 85%, at least 90%, at least 95%, or at least 99% identical to the sense or antisense strand of another nucleotide sequence. It will be understood that the term identical as used herein encompasses errors introduced during processing of a nucleotide sequence, such as by PCR amplification or sequencing reactions.

In one embodiment, the sample containing the plurality of linear double-stranded DNA molecules is split into two samples and a portion of each sample is used as a template for a PCR reaction with a common pair of primers. In one embodiment, a region of at least one of the plurality of linear double-stranded DNA molecules is amplified to produce a plurality of amplicons, wherein at least one amplicon comprises the non-degenerate sequence tag and sequence complementary to a portion of a single member of the target fragment library. In another embodiment, the plurality of amplicons comprising the non-degenerate sequence tag further comprises at least one amplicon comprising sequence complementary to a portion of defined sequence P1 and a portion of defined sequence P2.

A representative example of one embodiment of this step of the method is illustrated in FIG. 3. As shown in FIG. 3, a primer 70 that is complementary to a portion of P3 sequence 60 is paired with primer 80 that is complementary to a portion of P2 sequence 50 in PCR reaction 1, thereby producing PCR 1 amplicon 100. In another reaction, primer 70 that is complementary to a portion of P3 sequence 60 is paired with primer 90 that is complementary to a portion of P1 sequence 30 in PCR reaction 2, thereby producing PCR 2 amplicon 200. The orientation of the non-degenerate sequence tag 42 depends on which primer pair is used: The non-degenerate sequence tag 42 in amplicons produced using primer pair 70/80 (P3/P2) is in an opposite orientation to the non-degenerate sequence tag 42 in amplicons produced using primer pair 70/90 (P3/P1). It is understood that whereas FIG. 3 shows only two representative amplicons 100, 200 amplified from two linear double-stranded DNA molecules 58, in the practice of the method, one or more regions of a plurality of double-stranded DNA molecules are amplified, thereby producing a plurality of amplicons comprising sequence from different regions of the target fragment molecule 10. The location of the amplified regions is determined by the fragmentation breakpoints 56 in the copies of each circularized double-stranded DNA molecule, as described above.

As shown in FIG. 3, in one embodiment PCR 1 amplicon 100 includes target fragment sequence that is proximal to P1 sequence 30, whereas PCR 2 amplicon 200 includes target fragment sequence that is proximal to P2 sequence 50. As used herein, the term proximal refers to sequence that is located adjacent to, nearest to, or at the same end of a molecule as a reference sequence. In one embodiment, the plurality of amplicons comprising the non-degenerate sequence tag 42 further comprises at least one amplicon comprising sequence from at least one of the linear double-stranded DNA molecules, wherein the sequence from at least one of the linear double-stranded DNA molecules is located proximal to P1. In another embodiment, the plurality of amplicons comprising the non-degenerate sequence tag further comprises at least one amplicon comprising sequence from at least one of the linear double-stranded DNA molecules, wherein the sequence from at least one of the linear double-stranded DNA molecules is located proximal to P2.

The method further comprises sequencing the target fragment library. The method provides templates useful for micro-sequencing technologies, such as those described in Mardis, E. R., "The Impact of Next-Generation Sequencing Technology on Genetics," *Trends Genet.* 24:133-141 (2008), and Wold, B., et al., "Sequence Census Methods for Functional Genomics," *Nat. Methods* 5:19-21 (2008). In one embodiment, the linear double-stranded DNA molecules from step (d) above can be directly sequenced, for example, using massively parallel single molecule DNA micro-sequencing technologies without amplifying a subregion of the molecule. In some embodiments, the amplified regions of the target fragment sequence serve as the sequencing templates. The amplified regions are useful as templates for massively parallel DNA micro-sequencing technologies because some of these sequencing platforms have maximal template lengths on the order of 500 to 1,000 base pairs. In one embodiment illustrated in FIG. 3, sequencing reads 110 and 120 of PCR 1 amplicon 100 and sequencing reads 210 and 220 of PCR 2 amplicon 200 are primed using primers that are complementary to the sense or antisense strand of P3 sequence 60 and primers that are complementary to the sense or antisense strand of the adaptor sequence 20. As shown in FIG. 3, sequencing reads 110, 210 comprise sequence internal to the target fragment, wherein the start point of each sequence is determined by the essentially random fragmentation breakpoints 56 in the copies of each circularized double-stranded DNA molecule. Sequencing reads 120, 220 comprise the non-degenerate sequence tag 42. In one embodiment, the plurality of amplicons are sequenced using a first oligonucleotide primer that is complementary to the sense strand of the adaptor sequence and a second oligonucleotide primer that is complementary to the antisense strand of P3. In another embodiment, the plurality of amplicons are sequenced using a first oligonucleotide primer that is complementary to the antisense strand of the adaptor sequence and a second oligonucleotide primer that is complementary to the sense strand of P3.

In one embodiment, the plurality of amplicons is sequenced from both ends, thereby producing a pair of associated end sequences from one or more of the plurality of amplicons. As used herein, the term "associated" refers to two or more sequences comprising sequence from the same target fragment, such that one sequence comprises the fragmentation breakpoint or sequence proximal to the fragmentation breakpoint, and the second sequence comprises at least a portion of the non-degenerate sequence tag. In another embodiment, the method comprises sequencing the plurality of amplicons to produce a plurality of associated sequences. In one embodiment, the associated sequences comprise a first sequence comprising a fragmentation breakpoint in the linear double-stranded DNA molecule and a second sequence comprising the non-degenerate sequence tag. In another embodiment, the associated sequences comprise a first sequence comprising sequence proximal to a fragmentation breakpoint in the linear double-stranded DNA molecule and a second sequence comprising the non-degenerate sequence tag.

In one embodiment, a plurality of amplicons amplified from a plurality of linear double-stranded DNA molecules comprising the same non-degenerate sequence tag is sequenced in parallel, thereby producing a plurality of associated sequences comprising the same non-degenerate sequence tag. In another embodiment, a plurality of amplicons amplified from a plurality of linear double-stranded DNA molecules comprising different non-degenerate sequence tags are sequenced in parallel, thereby producing a plurality of associated sequences comprising different non-degenerate sequence tags. Subassembly of short reads with the same degenerate sequence tag into long reads.

Figure 4:
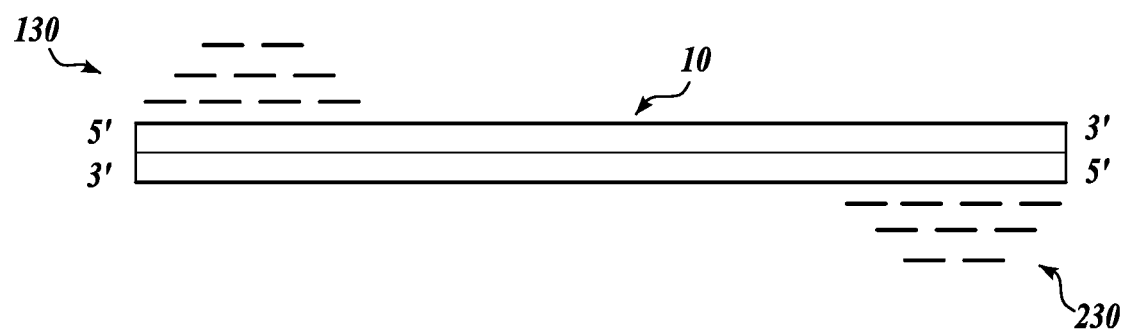
FIG. 4 schematically illustrates the clustering of sequence reads derived from sequencing the PCR amplified regions shown in FIG. 3, wherein sequences comprising the same non-degenerate sequence tag are clustered into longer subassemblies corresponding to each end of a target DNA fragment, in accordance with an embodiment of the invention.

In the method, sequencing reads comprising the same non-degenerate sequence tag are clustered with the corresponding associated sequencing reads to produce a longer sequencing read, also referred to herein as a subassembly. In one representative embodiment illustrated in FIG. 4, a plurality of sequencing reads 130 derived from a plurality of PCR 1 amplicons 100 and a plurality of sequencing reads 230 derived from a plurality of PCR 2 amplicons 200 is clustered together using computational algorithms Computational algorithms useful for assembling nucleotide sequences are well known in the art and include the phrap algorithm (developed at the University of Washington, Seattle, Wash.), as further described in Example 1. In one embodiment, associated sequences are clustered with other associated sequences that contain the same non-degenerate sequence tag to produce a subassembly. Clustered sequences with the same non-degenerate sequence tag are potentially derived from the same target fragment. A cluster of sequences in which the non-degenerate sequence tag is oriented in the same 5' to 3' direction corresponds to one end of each circularized target fragment. A cluster of sequences in which the same non-degenerate sequence tag is oriented in the opposite direction corresponds to the other end of the same circularized target fragment. The method allows clusters of associated sequences from each end of a kilobase-scale target fragment to be assembled into subassemblies of longer sequences. The potential length of subassembled longer sequences is limited by the maximal template length that is compatible with the sequencing platform of choice. In one embodiment, the method comprises assembling the plurality of associated sequences that include the same non-degenerate sequence tag to generate one or more longer sequences comprising fragmentation breakpoint sequences from the plurality of linear double-stranded DNA molecules. In some embodiments, gel-based size selection of PCR amplicons and independent sequencing of PCR amplicons from different size ranges is performed to provide additional information to help position short micro-reads for subassembly into longer reads. A representative embodiment of this aspect of the invention is described in Example 1.

In a second aspect of the invention, a method is provided for preparing a DNA sequencing library that brings more distal fragmentation breakpoints into close proximity to the non-degenerate sequence tag. The method is useful because some sequencing platforms perform optimally with template molecules that are relatively short, for example, less that about 500 base pairs in length. This aspect of the method brings more distal fragmentation breakpoints into close proximity to the adaptor molecule, allowing the subassembly of additional sequences from the target fragment that otherwise could not be sequenced due to the length of the template molecule. In one embodiment, the method comprises the following steps:

(a) circularizing a target fragment library with a plurality of adaptor molecules to produce a population of first circularized double-stranded DNA molecules, wherein the plurality of adaptor molecules comprises a first defined sequence P1 comprising a first restriction enzyme recognition site R1, a degenerate sequence tag, and a second defined sequence P2 comprising a second restriction enzyme recognition site R2, such that at least one of the first circularized double-stranded DNA molecule comprises a non-degenerate sequence tag and a member of the target fragment library;

(b) amplifying the population of first circularized double-stranded DNA molecules to produce a plurality of copies of each first circularized double-stranded DNA molecule, wherein the copies of each first circularized double-stranded DNA molecule comprise the same non-degenerate sequence tag;

(c) fragmenting the plurality of copies of each first circularized double-stranded DNA molecule to produce a plurality of first linear double-stranded DNA molecules, wherein the plurality of first linear double-stranded DNA molecules may be the same or different, and at least one of the plurality of first linear double-stranded DNA molecules contains the non-degenerate sequence tag present in the plurality of copies of each first circularized double-stranded DNA molecule;

(d) adding a third defined sequence P3 to at least one of a first end and a second end of at least one of the plurality of first linear double-stranded DNA molecules from step (c);

(e) digesting at least one of the first linear double-stranded DNA molecules from step (d) with restriction enzyme R1, thereby producing an R1 digested double-stranded DNA molecule;

(f) circularizing the R1 digested double-stranded DNA molecule with a first bridging oligonucleotide B1 to generate a second circularized double-stranded DNA molecule;

(g) amplifying the second circularized double-stranded DNA molecule of step (f) to produce a plurality of copies of the second circularized double-stranded DNA molecule;

(h) fragmenting the plurality of copies of the second circularized double-stranded DNA molecule to produce a plurality of second linear double-stranded DNA molecules, wherein at least one of the plurality of second linear double-stranded DNA molecules contains the non-degenerate sequence tag present in the plurality of copies of the second circularized double-stranded DNA molecule;

(i) adding a fourth defined sequence P4 to at least one of a first end and a second end of at least one of the plurality of second linear double-stranded DNA molecules; and (j) amplifying a region of at least one of the plurality of second linear double-stranded DNA molecules to produce a plurality of amplicons, wherein each amplicon comprises the non-degenerate sequence tag and sequence complementary to a portion of a single member of the target fragment library.

In this aspect of the invention, the method steps (a)-(d) are similar to steps (a)-(d) of the previous method, discussed above, with the added feature that defined sequences P1 and P2 contain recognition sites for restriction enzymes. The restriction enzyme recognition sites may be the same or different. In one embodiment, the cognate restriction enzymes that bind to the recognition sites are infrequent cutters, for example, homing endonucleases. Homing endonucleases are double-stranded DNases that have large, asymmetric recognition sites (12-40 base pairs). Homing endonucleases are well known in the art, and include the enzymes I-CeuI, I-SceI, PI-PspI and PI-SceI.

In one embodiment, the method provides for adding a common defined sequence P3 to at least one end of the plurality of linear double-stranded DNA molecules generated by fragmenting the plurality of copies of each circularized DNA molecule. In one embodiment, the linear DNA fragments are end-repaired and A-tailed, and ligated to a T-tailed P3 sequence.

In one embodiment, the sample containing the plurality of linear double-stranded DNA molecules with P3 at one or both ends is split into two samples. Each sample is digested with a restriction enzyme that cuts in sequence P1 and/or sequence P2. Therefore, one embodiment of this aspect of the invention comprises the following additional steps:

(i) digesting at least one of the first linear double-stranded DNA molecules from step (d) with restriction enzyme R2, thereby producing an R2 digested double-stranded DNA molecule;

(ii) circularizing the R2 digested double-stranded DNA molecule with a second bridging oligonucleotide B2 to generate a third circularized double-stranded DNA molecule;

(iii) amplifying the third circularized double-stranded DNA molecule to produce a plurality of copies of the third circularized double-stranded DNA molecule;

(iv) fragmenting the plurality of copies of the third circularized double-stranded DNA molecule to produce a plurality of third linear double-stranded DNA molecules, wherein at least one of the plurality of third linear double-stranded DNA molecules contains the non-degenerate sequence tag present in the plurality of copies of the third circularized double-stranded DNA molecule;

(v) adding a fifth defined sequence P5 to at least one of a first end and a second end of at least one of the plurality of third linear double-stranded DNA molecules; and (vi) amplifying a region of at least one of the plurality of third linear double-stranded DNA molecules to produce a plurality of amplicons comprising the sequence tag, wherein each amplicon comprises the non-degenerate sequence tag and sequence complementary to a portion of a single member of the target fragment library.

Figure 5:
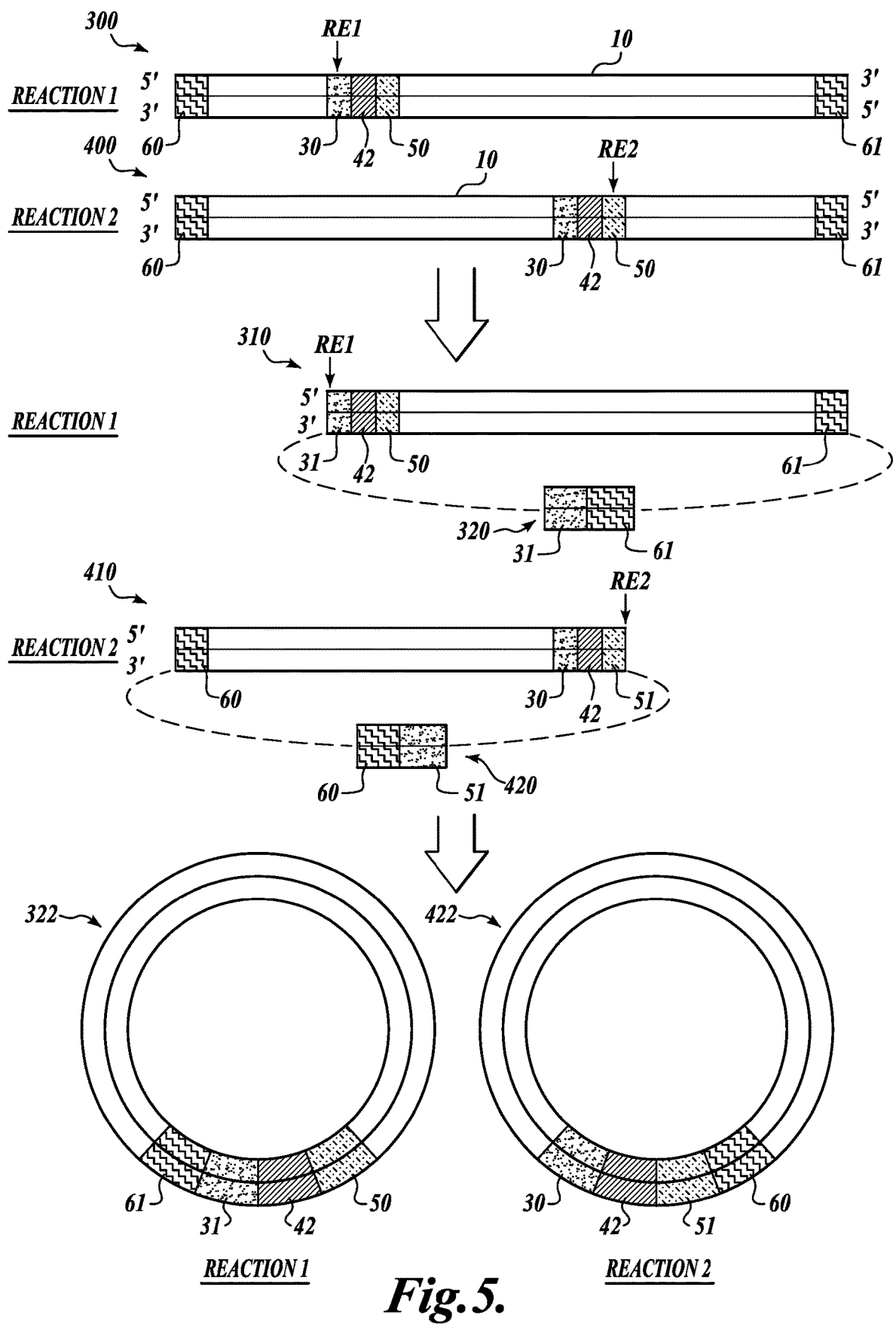
FIG. 5 schematically illustrates another aspect of the invention, wherein linear DNA molecules comprising a non-degenerate sequence tag and a common adaptor sequence at both ends, as shown in FIG. 3, are digested with restriction enzymes and circularized with bridging oligonucleotides, thereby producing circular DNA molecules having a distal sequence of interest brought into close proximity to the adaptor sequence.

FIG. 5 illustrates one representative embodiment of the method. In Reaction 1, a linear double-stranded fragment 300 having a defined P3 sequence 60, 61 at both ends is digested with a first restriction enzyme (RE1) that recognizes a binding site within common defined P1 sequence 30. In Reaction 2, a linear double-stranded fragment 400 having a defined P3 sequence 60, 61 at both ends is digested with a second restriction enzyme (RE2) that recognizes a binding site within common defined P2 sequence 50. As further shown in FIG. 5, in Reaction 1, the RE1 digested molecule 310 is ligated to a first bridging oligonucleotide 320, referred to herein as BR1, thereby producing a circular DNA molecule (indicated by the dashed line). Similarly, in Reaction 2, the RE2 digested molecule 410 is ligated to a second bridging oligonucleotide 420, referred to herein as BR2, thereby producing a circular DNA molecule (indicated by the dashed line). In one embodiment, the bridging oligonucleotide BR1 comprises sequences complementary to at least a portion of RE1 digested P1 sequence 31, and further comprises sequences complementary to at least a portion of P3 sequence 60, 61. In one embodiment, the bridging oligonucleotide BR2 comprises sequences complementary to at least a portion of RE2 digested P2 sequence 51 and further comprises sequences complementary to at least a portion of P3 sequence 60, 61. In one embodiment, sequences 60 and 61 are the same. In one embodiment, sequences 60 and 61 are different.

Referring again to FIG. 5, in one embodiment RE1 digestion results in removal of sequences upstream of the adaptor molecule 20 and the ligation reaction with bridging oligo BR1 results in the distal, downstream P3 sequence 61 being located adjacent to the adaptor sequence in the circularized molecule 322. In one embodiment, sequence 61 is located adjacent to the RE1 digested P1 sequence 31. In another embodiment, RE2 digestion results in removal of sequences downstream of the adaptor molecule 20 and the ligation reaction with bridging oligo BR2 results in the distal, upstream P3 sequence 60 becoming located adjacent to the adaptor sequence in the circularized molecule 422. In particular, sequence 60 is located adjacent to the RE2 digested P2 sequence 51.

In the method, the circularized molecules 322, 422 generated using the bridging oligos are amplified to produce a plurality of copies of each circularized double-stranded DNA molecule. In one embodiment, the circularized double-stranded DNA molecules are amplified using isothermal rolling circle amplification. In another embodiment, the circularized double-stranded DNA molecules are amplified using multiple displacement amplification.

Figure 6:
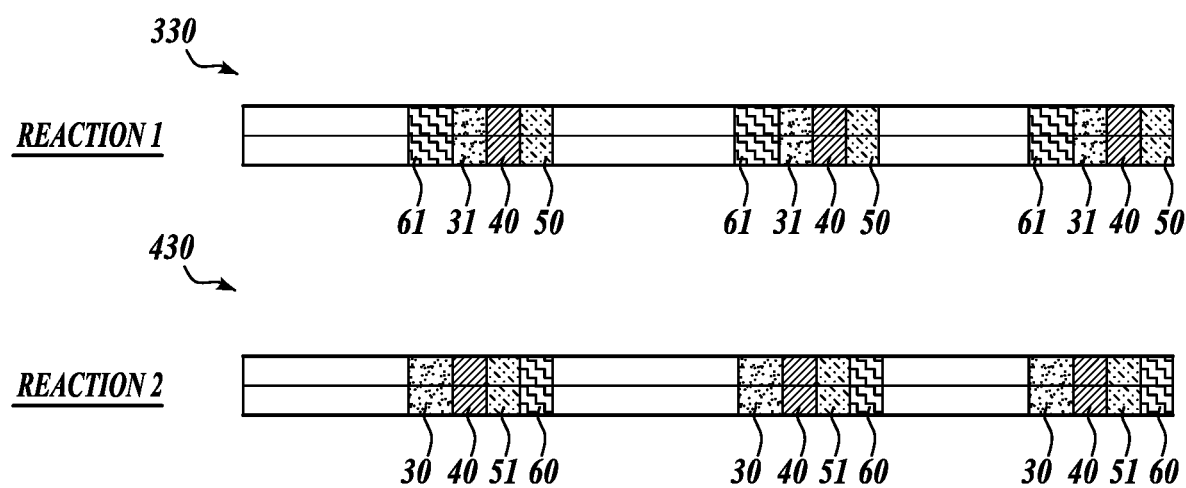
FIG. 6 schematically illustrates the amplified copies of circular DNA molecules circularized with bridging oligonucleotides shown in FIG. 5, in accordance with an embodiment of the invention.

Referring now to one representative embodiment shown in FIG. 6, Reaction 1 illustrates the plurality of concatemerized copies 330 of a double-stranded DNA molecule circularized by ligation to BR1, as described above. Reaction 2 illustrates the plurality of concatemerized copies 430 of a double-stranded DNA molecule circularized by ligation to BR2, as described above. In the plurality of copies 330, the P3 sequence 61 is located adjacent to and upstream of RE1 digested P1 sequence 31. In the plurality of copies 430, the P3 sequence 60 is located adjacent to and downstream of RE2 digested P2 sequence 51.

In one embodiment, the plurality of copies of each circularized double-stranded DNA molecule are fragmented to produce a plurality of linear double-stranded DNA molecules. In this embodiment, one or more of the linear double-stranded DNA molecules contains the same non-degenerate sequence tag present in the double-stranded DNA molecule circularized with the bridging oligonucleotides BR1 or BR2. In one embodiment, the plurality of copies of each circularized double-stranded DNA molecule are fragmented by nebulization. In another embodiment, the plurality of copies of each circularized double-stranded DNA molecule are fragmented by sonication.

In one embodiment, a common defined sequence P4 is added to one or both ends of the plurality of linear double-stranded DNA molecules. In another embodiment, a common defined sequence P5 is added to one or both ends of the plurality of linear double-stranded DNA molecules. In some embodiments, P4 and P5 are the same or different. The common defined sequences P4 and P5 may be any sequence of nucleotides. In some embodiments, the common defined sequences P4 and P5 are 15 bp to 50 bp in length. In one embodiment, the common defined sequences P4 and P5 are designed as binding sites for oligonucleotide primers that are useful for amplifying a region of the linear double-stranded DNA molecule, for example, by PCR.

Figure 7:
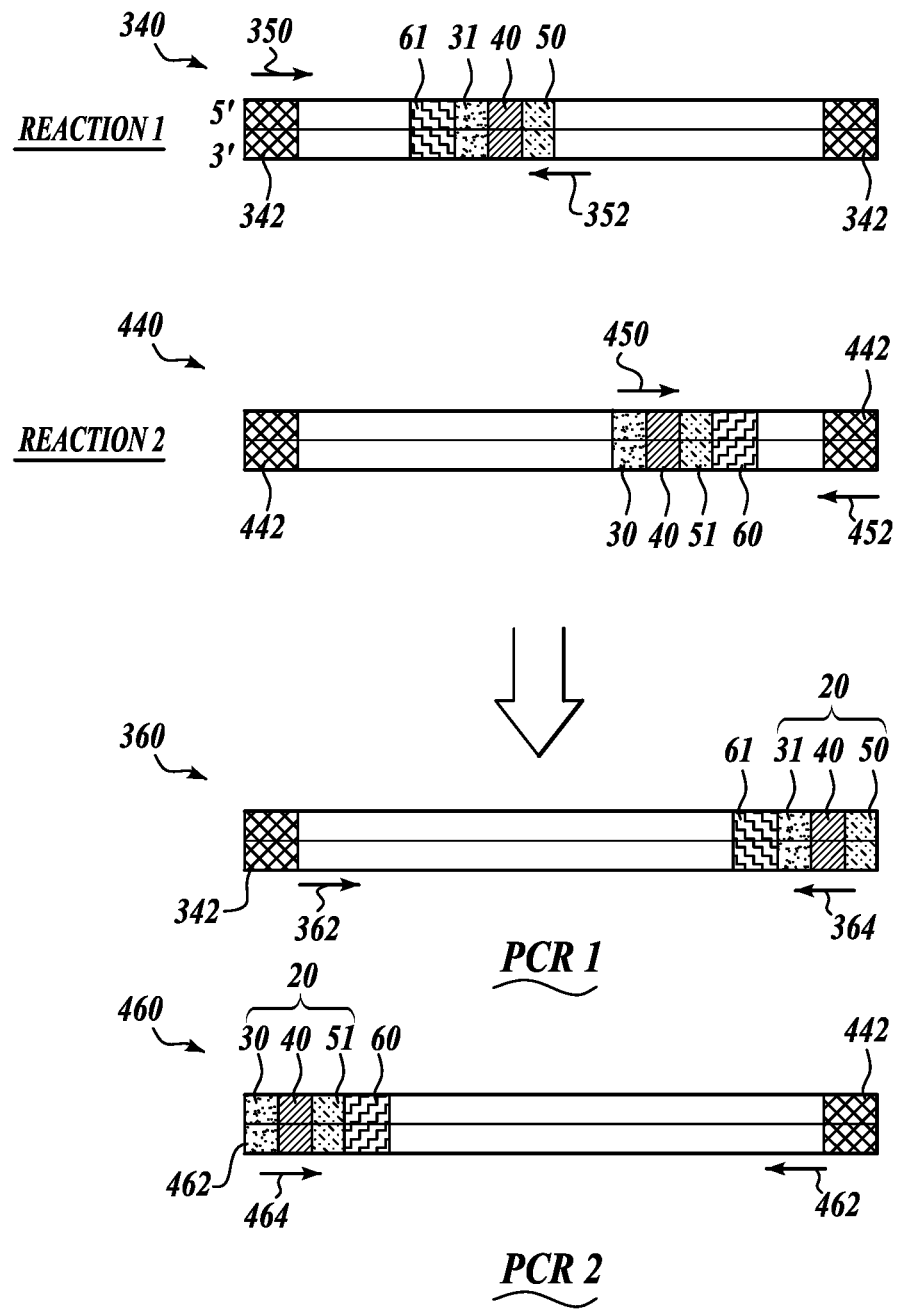
FIG. 7 schematically illustrates linear DNA molecules produced by fragmentation of the amplified copies of circular DNA molecules shown in FIG. 6, wherein the linear DNA molecules have a common defined sequence added to both ends and further illustrates the amplification and sequencing of a region of each linear DNA molecule, in accordance with an embodiment of the invention.

Referring now to one representative embodiment shown in FIG. 7, Reaction 1 illustrates a linear double-stranded DNA molecule 340 produced by fragmentation of the copies of each double-stranded DNA molecule circularized with bridging oligo BR1, as described above. Reaction 2 illustrates a linear double-stranded DNA molecule 440 produced by fragmentation of the copies of each double-stranded DNA molecule circularized with bridging oligo BR2, as described above. A common defined sequence 342 is added to one or both ends of the linear fragment 340, and a common defined sequence 442 is added to one or both ends of the linear fragment 440. In some embodiments, sequences 342 and 442 are the same or different.

In one embodiment, oligonucleotide primers 350 and 352 are used to amplify a region of linear double-stranded DNA molecule 340, and oligonucleotide primers 450 and 452 are used to amplify a region of linear double-stranded DNA molecule 440. Amplification Reaction 1 produces at least one amplicon 360, referred to herein as PCR 1, and amplification Reaction 2 produces at least one amplicon 460, referred to herein as PCR 2. Whereas only one representative amplicon is illustrated, it is understood that a PCR reaction typically produces hundreds to thousands of copies (amplicons) of each template sequence, thereby producing a plurality of amplicons comprising sequence from each amplified region of the target fragment. Thus, as used herein, the term "amplicon" includes the plurality of amplicons produced by a PCR reaction. In one embodiment, the amplicons are less than about 500 bp in length. In another embodiment, the amplicons are less than about 1,000 bp in length.

In one embodiment, amplicons 360 and 460 are sequenced to produce at least two associated sequencing reads from each amplicon, wherein the term "each amplicon" includes at least one of the plurality of amplicons produced by a PCR reaction. In the practice of the method, it is understood that, based on the availability of reagents and reaction kinetics, only a subset of the population of amplicons from an amplified region may be used as templates for a sequencing reaction. As shown in FIG. 7, in one embodiment, the amplicons 360 and 460 are end sequenced, thereby producing a pair of associated end sequences 362, 364 from amplicon 360 and a pair of associated end sequences 462, 464 from amplicon 460. Sequencing reads 362 and 462 are primed using primers complementary to the common defined sequence 342 and 442, respectively. Sequencing reads 364 and 464 are primed using primers complementary to a portion of adaptor sequence 20. Sequencing reads 362 and 462 comprise sequence internal to a target fragment and, in one embodiment, further comprise sequence corresponding to a fragmentation breakpoint in the plurality of copies 330, 430 of the double-stranded DNA molecules circularized with a bridging oligonucleotide. Sequencing reads 364 and 464 comprise sequence complementary to the non-degenerate sequence tag sequence. While only one amplicon for each reaction is illustrated, it is understood that in some embodiments a plurality of different amplicons are sequenced, wherein the plurality of different amplicons comprise sequence from the same target fragment and sequence from the same non-degenerate sequence tag. In one embodiment, a plurality of amplicons is sequenced to produce a plurality of associated sequences, wherein the associated sequences comprise a first sequence comprising a fragmentation breakpoint in one of the plurality of linear double-stranded DNA molecules, wherein the linear double-stranded DNA molecules are fragments of a double-stranded DNA molecule circularized with a bridging oligonucleotide and a second sequence comprising the non-degenerate sequence tag sequence.

Figure 8:
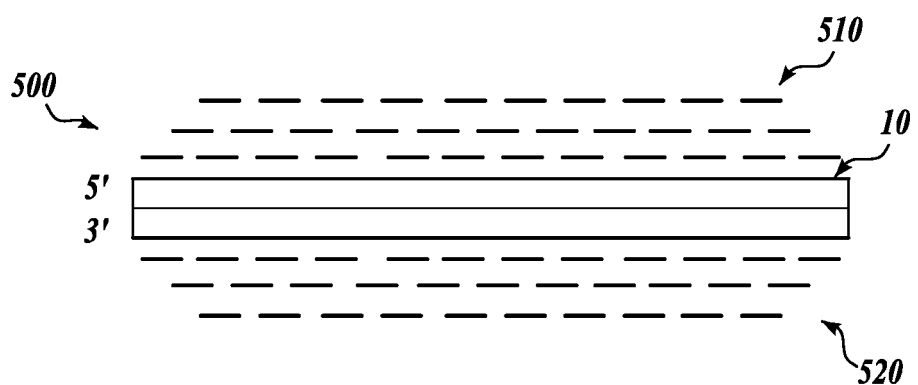
FIG. 8 schematically illustrates the clustering of sequence reads from the amplified regions shown in FIG. 7, wherein sequences comprising the same non-degenerate sequence tag are clustered into longer subassemblies corresponding to a target fragment sequence that was located distal to the adaptor sequence.

In the practice of the method, the plurality of associated sequences are clustered and assembled as described above. In one representative embodiment illustrated in FIG. 8, a subassembly 500 of short reads comprising the same non-degenerate sequence tag are assembled into longer reads of contiguous sequences derived from the same target fragment 10. One subassembly includes the plurality of associated sequences 510 from the target fragment circularized with the first bridging oligonucleotide BR1. One subassembly includes the plurality of associated sequences 520 from the target fragment circularized with the second bridging oligonucleotide BR2. The potential length of the subassembled contig is limited by the extent to which long DNA molecules can be reliably circularized with the bridging oligonucleotides. In some embodiments, gel-based size selection of PCR amplicons and independent sequencing of PCR amplicons from different size ranges is performed to provide additional information to help position short micro-reads for subassembly into longer reads.

In a third aspect, the invention provides methods for preparing a DNA sequencing library that does not rely on a non-degenerate sequence tag, but instead uses the ends of a target fragment as the sequence tags. In one embodiment of this aspect of the method, target DNA fragments are cloned into a vector that comprises two type IIs restriction enzyme (RE) sites flanking the cloning insert site. Type IIs restriction enzymes are well known in the art and generally cut at a distance from an asymmetric recognition site. In some embodiments, the two type IIs RE sites are oriented such that the corresponding restriction enzymes digest sequence tags derived from either end of the target fragment shotgun cloned into the vector.

In one embodiment, the invention provides a method for preparing a DNA sequencing library comprising the following steps:

(a) providing a population of circular double-stranded DNA molecules; wherein each circular double-stranded DNA molecule comprises a sequence of interest having a first end joined to the first end of a vector sequence, an internal portion, and a second end joined to the second end of the vector sequence;

(b) fragmenting a portion of the population of circular double-stranded DNA molecules to produce a plurality of linear double-stranded DNA molecules;

(c) adding a common adaptor sequence to at least one end of at least one of the plurality of linear double-stranded DNA molecules; and (d) amplifying a region of at least one of the plurality of linear double-stranded DNA molecules to produce a plurality of amplicons, wherein at least one amplicon comprises sequence complementary to the sequence of interest.

In one embodiment, the sequence of interest comprises genomic DNA. In another embodiment, the sequence of interest comprises cDNA.

Figure 9:
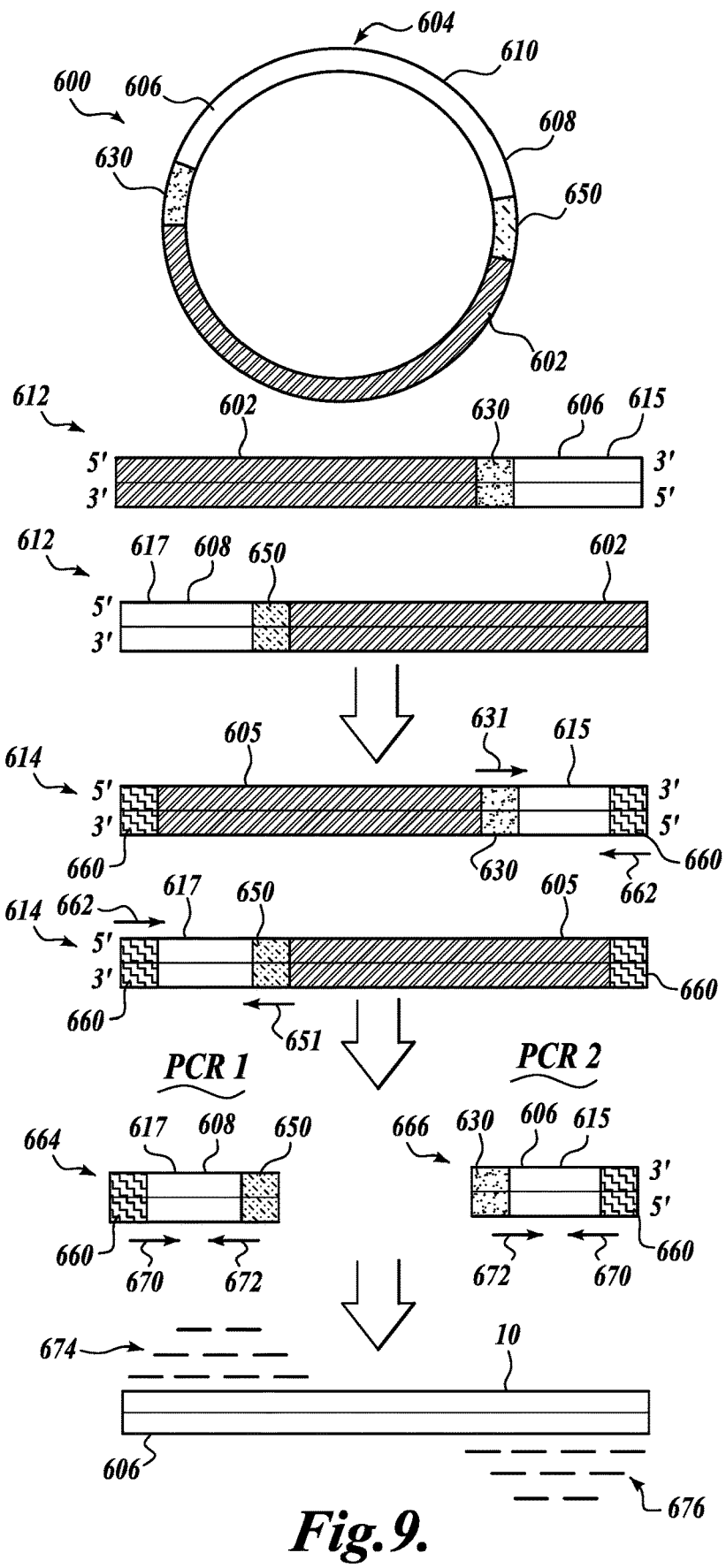
FIG. 9 schematically illustrates another aspect of the invention, wherein a target fragment library is constructed in a plasmid vector, the circular molecules are fragmented to produce linear fragments, a common adaptor is added to both ends of the linear DNA fragments, a region of each linear fragment is amplified by PCR, and sequences comprising sequence from the same end portions of a target sequence are clustered into subassemblies.

FIG. 9 illustrates one representative embodiment of the method. A circular double-stranded DNA molecule 600 comprises a vector sequence 602 and an insert sequence of interest 604, wherein the insert sequence 604 comprises a first end portion 606, a second end portion 608, and an internal portion 610. In one embodiment, the vector sequence 602 comprises a first common defined sequence 630, referred to herein as P1, adjacent to end portion 606 of the insert sequence 604, and a second common defined sequence 650, referred to herein as P2, adjacent to end portion 608 of the insert sequence 604. In one embodiment, common defined sequence 630 contains a type IIs RE recognition site. In another embodiment, common defined sequence 650 contains a type IIs RE recognition site. In one embodiment, the type IIs RE recognition sites in sequence 630 and 650 are the same. In another embodiment, the type IIs RE recognition sites in sequence 630 and 650 are different. Whereas only one circular DNA molecule is illustrated, it is understood that in some embodiments a plurality of target fragments comprising multiple sequences of interest are cloned into the vector, thereby generating a population of circular double-stranded DNA molecules.

In one embodiment, the circular DNA molecule 600 comprises a cloned insert sequence of interest 604 and a vector 602 comprising an antibiotic resistance gene. In one embodiment, a population of circular DNA molecules, also known as plasmids, are transformed into *E. coli* bacteria using standard methods known in the art and the transformed bacteria are cultured in liquid media containing antibiotic selection, thereby multiplying the population of circular DNA molecules. The population of circular DNA molecules constitutes a target fragment library. A library comprising multiple different inserts cloned into a vector is also known in the art as a shotgun library. The complexity of the library is determined by the transformation efficiency. After a suitable number of bacteria are obtained, the circular plasmid DNA is extracted from the bacteria using methods known in the art. The extracted plasmid DNA contains many copies of each library member.

Referring again to FIG. 9, in one embodiment a portion of the population of circular double-stranded DNA molecules is fragmented to produce a plurality of linear double-stranded DNA molecules 612. In one embodiment, the DNA molecules are fragmented by nebulization, as described above. In another embodiment, the DNA molecules are fragmented by sonication, as described above. In some embodiments, the linear DNA fragments are end-repaired and A-tailed using methods known in the art. Because the fragmentation step is essentially random, some of the breakpoints will occur in the insert DNA 604, producing fragmented insert DNA 615 proximal to defined sequence 630 and fragmented insert DNA 617 proximal to defined sequence 650. In one embodiment, a common defined adaptor sequence 660, referred to herein as P3, is added to one or both ends of the linear double-stranded DNA molecules 612 to produce fragments 614. In one embodiment, the common adaptor sequence P3 is T-tailed to facilitate ligation to the A-tailed linear double-stranded DNA fragments.

As further shown in FIG. 9, in some embodiments the sample is split and two separate PCR reactions (PCR 1, PCR 2) are performed, thereby amplifying a region of the plurality of linear double-stranded DNA molecules. In one embodiment, primer 631, which anneals to defined P1 sequence 630, and primer 662, which anneals to common defined adaptor P3 sequence 660, are used to PCR amplify amplicon 666. In another embodiment, primer 651, which anneals to defined P2 sequence 650, and primer 662, which anneals to common defined adaptor P3 sequence 660, are used to PCR amplify amplicon 664. Amplicon 664 comprises insert sequence 617 that is proximal to defined sequence 650, and amplicon 666 comprises insert sequence 615 that is proximal to defined sequence 630. Whereas only two representative amplicons are shown, it is understood that, in some embodiments, a plurality of amplicons is produced by the PCR reactions, wherein one or more amplicons comprise sequence corresponding to the sequence of interest 604.

In one embodiment, the fragments 614 may be sequenced using primers that anneal to common defined sequence 630, common defined sequence 650, and common defined sequence 660, thereby producing a plurality of associated sequences. In some embodiments, the plurality of amplicons, for example, representative amplicons 664 and 666, are sequenced. As shown in FIG. 9, in one embodiment, sequencing reads 670 are primed from common defined sequence 660, whereas sequencing reads 672 are primed from either common defined sequence 630 or common defined sequence 650. Sequencing reads 672 comprise a sequence tag that corresponds to the end portions 606, 608 of a cloned target fragment of interest. Sequencing reads 670 comprise sequence internal to the target fragment of interest.

In one embodiment, the method comprises sequencing the plurality of amplicons described above to produce at least two associated sequences from at least one amplicon, wherein the associated sequences comprise a first sequence comprising sequence complementary to an end portion of the sequence of interest and a second sequence comprising sequence complementary to an internal portion of the sequence of interest, thereby producing a plurality of associated sequences complementary to an end portion and an internal portion of the sequence of interest. As used in this aspect of the invention, the term "associated" refers to two or more sequences comprising sequence from the same sequence of interest, such that one sequence comprises the fragmentation breakpoint, or sequence proximal to the fragmentation breakpoint, and the second sequence comprises sequence from a first end portion or second end portion of the cloned sequence of interest.

In the method, the plurality of associated sequences are assembled to produce one or more longer sequences, also called subassemblies, as described above. The sequences are assembled into a subassembly if one sequence corresponds to the same end portion sequence. In the representative embodiment illustrated in FIG. 9, clusters of associated sequences 674, 676 are located at each end of the sequence of interest. Cluster 674 comprises sequence from a first end portion 606 of a sequence of interest 604, whereas cluster 676 comprises sequence from a second end portion 608 of a sequence of interest 604. In one embodiment, the method comprises assembling the plurality of associated sequences to generate one or more longer subassemblies comprising sequence complementary to the sequence of interest, wherein sequences that are complementary to an internal portion of the sequence of interest are assembled if they are associated with the same sequence complementary to an end portion of the sequence of interest.

Figure 10:
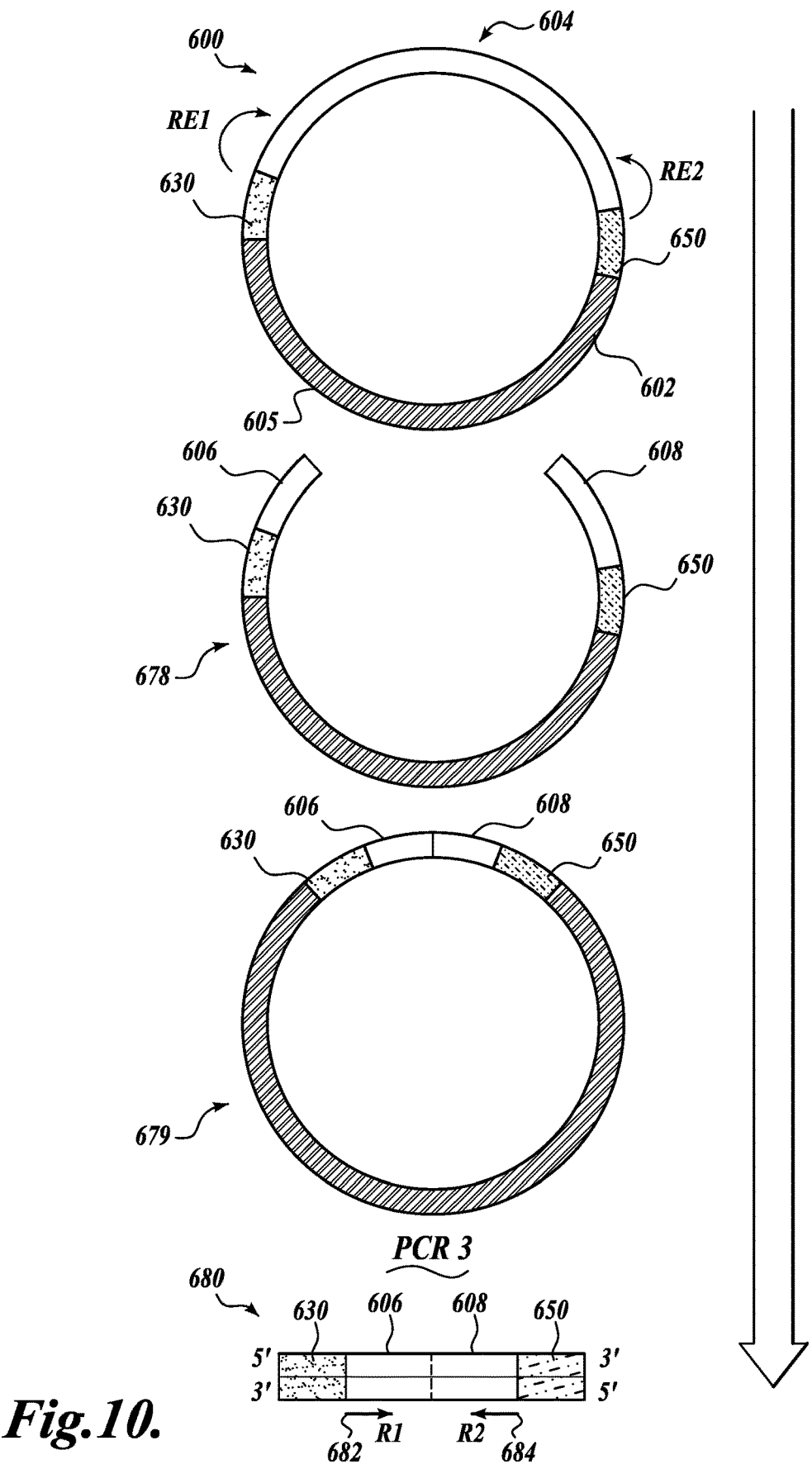
FIG. 10 schematically illustrates another embodiment of the method shown in FIG. 9, wherein the circular molecule comprising a target sequence of interest is digested with restriction enzymes that remove the internal portion of the sequence of interest, thereby allowing the joining and amplification of both ends of the sequence of interest.

In the method described in this aspect of the invention, the tag sequences used to associate and assemble sequences correspond to each end of the cloned sequence of interest, rather than to the same non-degenerate sequence tag. Therefore, the method further comprises additional steps necessary to join together subassemblies derived from each end of a sequence of interest. In one embodiment, a portion of the population of circular double-stranded DNA molecules described above is digested with restriction enzymes that recognize the restriction enzyme binding sites present in common defined sequences P1 and P2. Referring now to FIG. 10, in one representative embodiment a circular DNA molecule 600 is digested with RE1 and RE2, resulting in a linear molecule 678 having end portions 606 and 608. In one embodiment, the restriction enzymes are type IIs restriction enzymes. Examples of exemplary type IIs restriction enzymes include BsgI and BtgZ1. In one embodiment, RE1 and RE2 are the same or different. In some embodiments, the linear molecule is recircularized, for example, by self-ligation or using any other suitable method known in the art, to produce a recircularized molecule 679. While only one circular DNA molecule 600 is illustrated, it will be appreciated that in some embodiments the method comprises digesting a plurality of circular DNA molecules with restriction enzymes RE1 and/or RE2, wherein the plurality of circular DNA molecules comprise inserts having different sequences of interest. In one embodiment, the method further comprises digesting a portion of the population of circular double-stranded DNA molecules with at least one restriction enzyme, and recircularizing at least one of the digested double-stranded DNA molecules.

In another embodiment, a portion of the population of circular double-stranded DNA is mechanically sheared and at least one of the sheared molecules is recircularized. Mechanical shearing can be accomplished by various methods known in the art, including nebulization or sonication.

In some embodiments, the recircularized DNA molecules 679 are sequenced without further amplification, wherein at least one sequence comprises sequence that is complementary to one or both end portions of a sequence of interest. In one embodiment, the sequencing reactions are primed using primers that anneal to common defined sequence 630. In another embodiment, the sequencing reactions are primed using primers that anneal to common defined sequence 650. In some embodiments, the sequencing reactions are primed using one or more primers that anneal to the vector sequence 602.

Referring again to FIG. 10, in one embodiment the recircularized molecule 679 is amplified, for example, by PCR, using primers that anneal to common defined sequences 630 and 650. While only one amplicon 680 is illustrated, in some embodiments a plurality of recircularized molecules is amplified, using common primers, thereby producing a plurality of amplicons. In one embodiment, the plurality of amplicons comprise sequence from both ends of the cloned sequence of interest 604. The representative amplicon 680, referred to herein as PCR 3, is sequenced using primers that anneal to common defined sequence 630 and/or common defined sequence 650, thereby producing sequencing reads 682, referred to herein as R1, and/or 684, referred to herein as R2. In one embodiment, the sequencing reads R1 and R2 comprise sequence that is complementary to one or both vector-adjacent end portions 606, 608 of the sequence of interest. In another embodiment, a plurality of amplicons are sequenced, thereby producing a plurality of sequences, wherein at least one sequence comprises sequence that is complementary to one or both ends of a sequence of interest. In some embodiments, the method further comprises sequencing the plurality of amplicons to produce at least two associated sequences, thereby producing a plurality of associated sequences, wherein the at least two associated sequences comprise a first sequence comprising sequence that is complementary to a first end portion of a sequence of interest, and a second sequence comprising sequence that is complementary to a second end portion of the sequence of interest. A representative embodiment of this aspect of the invention is described in Example 2.

The invention further provides methods for associating the sequences that correspond to one or both end portions of a sequence of interest with the one or more longer contiguous sequences (subassemblies) generated by assembling sequences associated with a first end portion and a second end portion of the sequence of interest, thereby associating or mate-pairing the subassemblies from each end portion of a sequence of interest with each other. In one embodiment, the method comprises associating the sequences comprising sequence that is complementary to both ends of a sequence of interest with the one or more longer subassemblies described above, thereby associating the longer subassemblies from a first end and a second end of a sequence of interest with each other. In another embodiment, the method comprises assembling a first sequence that is complementary to a first end of a sequence of interest with one or more subassemblies, thereby associating the first sequence with a subassembly comprising sequence complementary to a first end portion of the sequence of interest. In another embodiment, the method comprises assembling a second sequence that is complementary to a second end of the sequence of interest with one or more subassemblies, thereby associating the second sequence with a subassembly comprising sequence complementary to a second end portion of the sequence of interest.

In a fourth aspect, the invention provides methods for preparing a DNA sequencing library that does not rely on circularization of fragments or cloning of fragments into a vector. In one embodiment of this aspect of the method, termed "subassembly," paired-end reads are obtained from fragments of genomic or metagenomic DNA libraries where one of the reads serves as a DNA tag that identifies groups of short reads that are derived from the same DNA fragment. As used herein, the term metagenomic refers to genomic DNA isolated from an uncultured microbial population. In one embodiment, the DNA fragments are about 300 to 600 bp in length. Each group of short, locally derived reads is merged using bioinformatics tools into a single long, subassembled read. Bioinformatics tools include software programs or algorithms specifically programmed to be executable by a computer. Importantly, the library construction of this aspect of the invention is entirely in vitro, and thus avoids the biases associated with cloning into bacterial vectors.

In one embodiment, the method comprises the following steps:

(a) incorporating at least one first nucleic acid adaptor molecule into at least one member of a target library comprising a plurality of nucleic acid molecules, wherein at least a portion of the first adaptor molecule comprises a first defined sequence;

(b) amplifying the plurality of nucleic acid molecules to produce an input library comprising a first plurality of amplified DNA molecules, wherein the amplified molecules comprise sequence identical to or complementary to at least a portion of the first adaptor molecule and sequence identical to or complementary to at least a portion of at least one member of the target library;

(c) fragmenting the input library to produce a plurality of linear DNA fragments having a first end and a second end;

(d) attaching at least one second nucleic acid adaptor molecule to one or both ends of at least one of the plurality of linear DNA fragments, wherein at least a portion of the second adaptor molecule comprises a second defined sequence;

(e) amplifying the plurality of linear DNA fragments to produce a sequencing library comprising a second plurality of amplified DNA molecules, wherein at least one of the plurality of amplified DNA molecules comprises sequence identical to or complementary to at least a portion of the first adaptor molecule, sequence identical to or complementary to at least a portion of the second adaptor molecule, and sequence identical to or complementary to at least a portion of a member of the target library.

As used herein, the term "target library" refers to a plurality of nucleic acid molecules whose sequence is desired to be known. In some embodiments, the target library comprises linear genomic or metagenomic DNA sequences. However, the target library may comprise or correspond to a plurality of any nucleic acid sequences, including sequence of single and double-stranded nucleic acid molecules, linear or circular nucleic acid molecules, RNA, and cDNA molecules. As used herein, the term "input library" refers to a plurality of DNA molecules that comprise an incorporated adaptor molecule. In some embodiments, the input library comprises a target library wherein a plurality of linear target library molecules has an adaptor molecule attached to or incorporated at one or both ends. In one embodiment, the adaptor molecule incorporated at one end of a target library molecule is different than the adaptor molecule incorporated at the other end. In one embodiment, the target library comprising an incorporated adaptor molecule is amplified to produce the input library.

The term "incorporated" refers to any method of adding an adaptor molecule to a target library molecule, including ligation, amplification, etc. In one embodiment, the adaptor molecules are covalently attached to the target library molecules. In some embodiments, the adaptor molecule is a single or double-stranded nucleic acid sequence. In one embodiment, the adaptor molecule is a double-stranded DNA molecule. In some embodiments, the adaptor molecule comprises a defined or known sequence and an unknown sequence. In one embodiment, the unknown sequence is a degenerate sequence.

In this aspect of the method, the input library is fragmented to produce a plurality of linear DNA fragments having a first end and a second end. The first end and second end of the fragments are also referred to as fragmentation breakpoints. In some embodiments, the input library comprises a plurality of concatemerized molecules, wherein the concatemers comprise a plurality of target library molecules having adaptor molecules attached to or incorporated therein. In this embodiment, the concatemers are fragmented to produce a plurality of linear concatemer fragments having a first end and a second end.

In another embodiment, the method comprises attaching at least one second nucleic acid adaptor molecule to one or both ends of at least one of the plurality of linear DNA fragments. In one embodiment, at least a portion of the second adaptor molecule comprises a second defined sequence.

In another embodiment of this aspect of the method, the plurality of linear DNA fragments comprising one or more first adaptor sequences and one or more second adaptor sequences is amplified to produce a sequencing library. As used herein, the term sequencing library refers to a library of nucleic acid molecules that are ready for sequence analysis. In some embodiments, the sequencing library comprises a second plurality of amplified DNA molecules, wherein at least one of the plurality of amplified DNA molecules comprises sequence identical to or complementary to at least a portion of the first adaptor molecule, sequence identical to or complementary to at least a portion of the second adaptor molecule, and sequence identical to or complementary to at least a portion of a member of the target library (for example, sequence corresponding to an original target library molecule). In some embodiments, the amplification step is carried out using PCR, wherein one PCR primer comprises sequence complementary to the first adaptor sequence and the second PCR primer comprises sequence complementary to the second adaptor sequence. In one embodiment, the PCR primer pairs further comprise sequence useful for second-generation sequencing platforms, as described below.

In some embodiments, the method further comprises sequencing the second plurality of amplified DNA molecules to produce a plurality of associated sequences. In one embodiment, the associated sequences comprise a first sequence adjacent to the first defined sequence of the first adaptor and a second sequence adjacent to the second defined sequence of the second adaptor. In one embodiment, at least one of the first sequences uniquely defines a single member of the target library (i.e., an original target library molecule whose sequence is desired to be known), and the second sequence comprises sequence adjacent to a fragmentation breakpoint from the fragmented input library. As used herein, the term "adjacent to" refers to nucleic acid sequences that are located immediately 5' or 3' of another sequence, such as an adaptor sequence or a fragmentation breakpoint sequence.

In another embodiment, the plurality of associated sequences are assembled to generate one or more longer subassembled sequences, wherein each subassembled sequence comprises sequence from a target library molecule, as described below.

It will be understood that the methods described above (in the first, second and third aspects of the invention) for preparing DNA sequencing libraries may be employed in the methods of this aspect of the invention. For example, one method for carrying out step (a) of the above method would be to circularize the target library with a plurality of adaptor molecules to produce a plurality of circularized DNA molecules. Thus, in some embodiments, the first step of the method further comprises circularizing the target library with a plurality of first adaptor molecules, wherein the plurality of first adaptor molecules comprises a first defined sequence P1, a degenerate sequence tag, and a second defined sequence P2, wherein at least one circularized nucleic acid molecule comprises the first adaptor molecule sequence having a non-degenerate sequence tag and sequence from a member of the target library.

In other embodiments, the first step of this aspect of the method further comprises circularizing a target library with a plurality of adaptor molecules to produce a population of circularized double-stranded DNA molecules, wherein the plurality of adaptor molecules comprises a first defined sequence P1 comprising a first restriction enzyme recognition site R1, a degenerate sequence tag, and a second defined sequence P2 comprising a second restriction enzyme recognition site R2, such that at least one of the circularized double-stranded DNA molecule comprises a non-degenerate sequence tag and a member of the target library.

Further, in one embodiment of this aspect of the method, the input library comprises a population of circular double-stranded DNA molecules; wherein each circular double-stranded DNA molecule comprises a vector sequence and a sequence of interest (i.e., sequence from a target library molecule), the sequence of interest having a first end joined to a first end of the vector sequence, an internal portion, and a second end joined to a second end of the vector sequence.

Figure 11A:
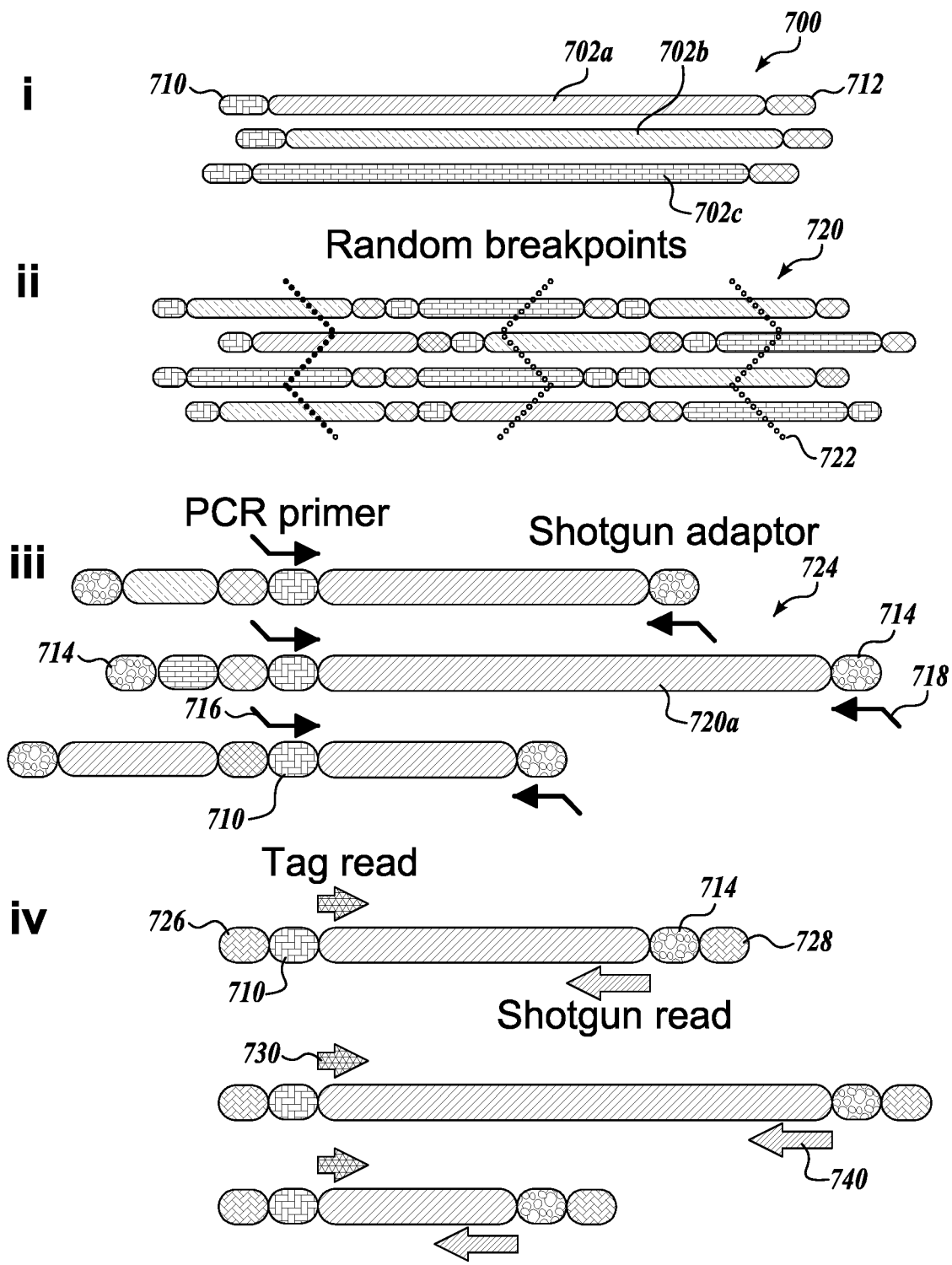
FIGS. 11A-11C schematically illustrate another aspect of the invention, wherein a target fragment library is constructed in vitro using a DNA tag to identify groups of shotgun sequence reads derived from the same genomic fragment, wherein the groups of shotgun sequences are subassembled into longer sequences.

FIG. 11 illustrates one representative embodiment of this aspect of the methods. Referring to FIG. 11A(i), genomic or metagenomic DNA is randomly fragmented to produce a first set of linear double-stranded DNA fragments 700, wherein the DNA fragments are size selected to produce a plurality of relatively long fragments 700. This first set of DNA fragments 700 is also known as a target library. In one embodiment, the DNA fragments are selected to be about 400 to 600 bp in length. The fragments 700 are ligated to tag adaptors 710, 712 to produce a plurality of adaptor-ligated DNA fragments 702a, 702b, 702c having the adaptor sequence incorporated at one or both ends of the linear DNA fragments. In one embodiment of the method, the tag adaptors 710, 712 comprise different sequences. The plurality of adaptor-ligated fragments 702a, 702b, 702c are diluted, amplified by PCR using primers that correspond to the adaptor sequences 710, 712, and randomly ligated together to generate high-molecular weight concatemers 720 (FIG. 11A(ii)). The dilution step prior to PCR effectively imposes a complexity bottleneck, such that a limited number of shotgun library fragments are amplified to high-copy number. The high-molecular weight concatemers 720 are randomly sheared or fragmented, as represented by the dotted lines 722, to produce a second set of linear DNA molecules having random breakpoints at each end.

Referring now to FIG. 11A(iii), a shotgun adaptor 714 is ligated to the ends of the concatemers fragments. The ligation reaction will add the shotgun adaptor 714 to one or both ends of each concatemer fragment 720a, producing a plurality of concatemer fragments 724 having the shotgun adaptor 714 at one or both ends. In one embodiment, the plurality of shotgun adaptor-ligated concatemer fragments 724 is amplified by PCR using two sets of primer pairs in separate reactions. For simplicity, only one set of primer pairs is illustrated. The first set of primer pairs comprises a first PCR primer 716 that corresponds to tag adaptor sequence 710 and a second PCR primer 718 that corresponds to the shotgun adaptor sequence 714. The second set of primer pairs comprises a first PCR primer that corresponds to tag adaptor sequence 712 (not shown) and the same second PCR primer 718 that corresponds to the shotgun adaptor sequence 714. In one embodiment, the PCR primers include sequences compatible with Illumina® flowcell sequencing technology. In one embodiment, the first PCR primer 716 includes the flowcell compatibility component of the standard Illumina® paired-end forward adaptor sequence at the 5' end, and the primer 718 includes the flowcell compatibility component of the standard Illumina® paired-end reverse adaptor sequence at the 5' end. In some embodiments, the amplified PCR products are size-selected to a range of about 300 to 600 bp.

Referring now to FIG. 11A(iv), the second set of PCR reactions produces a plurality of amplicons, wherein each amplicon has an Illumina® adaptor sequence 726, 728 at each end, wherein the Illumina® adaptor sequences flank the tag adaptor 710 and the shotgun adaptor 714, respectively. It will be understood that the Illumina® adaptor sequences 726, 728 are also added to fragments amplified with the second set of PCR primer pairs that corresponds to tag adaptor 712 and shotgun adaptor 714 (not shown). The second set of PCR reactions generates a population of nested sub-libraries derived from the original long fragment library. The population of PCR products is end-sequenced using the Illumina® sequencing platform. The sequence read 730 adjacent to the tag adaptor 710 (called the "tag read") corresponds to one end of the original genomic or metagenomic fragment 700. The tag read 730 is useful for identifying the original long DNA fragment from which a given amplicon was derived. The sequence read 740 adjacent to the shotgun adaptor 714 ("shotgun read") corresponds to sequence adjacent to a random break-point in the original long DNA fragment. In one embodiment, the tag read 730 is about 20 bp, whereas the shotgun read 740 is about 76 bp (illustrated by the unequal sizes of the arrows 730 and 740). It will be understood that a second set of tag reads and shotgun reads are obtained from the PCR products amplified using the second set of primer pairs described above that correspond to tag adaptor 712 and shotgun adaptor 714 (not shown).

Figure 11B:
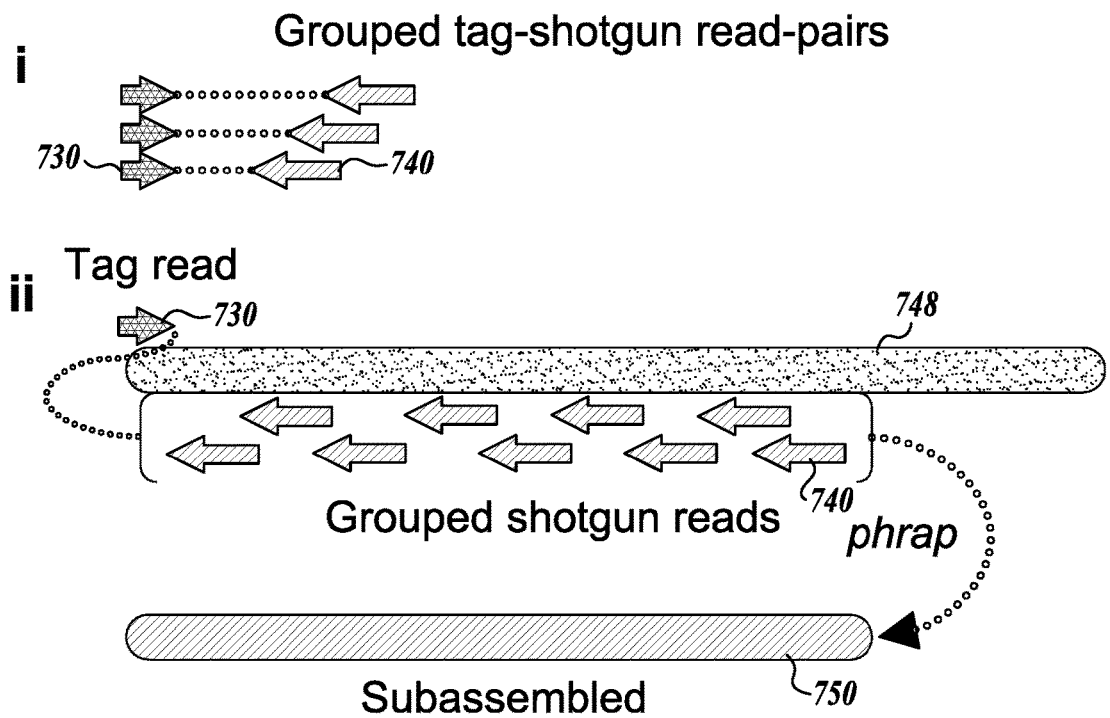

Referring now to FIG. 11B, a further embodiment of the method will be described. A plurality of paired-end sequences comprising a plurality of tag reads 730 and a plurality of shotgun reads 740 are obtained as described above (FIG. 11B(i)). The shotgun reads 740 are grouped in silico using a computer programmed with executable instructions to run a grouping algorithm based on the sequence of the corresponding tag read 730 (FIG. 11B(ii)). The group of shotgun reads 740 defined by a shared tag read are randomly distributed across an original genomic or metagenomic fragment 748 of unknown sequence. The group of shotgun reads 740 is subjected to phrap assembly to generate one or more subassembled reads 750 that correspond in sequence to the original genomic fragment (for example, fragment 702a of FIG. 11A). It will be further understood that a second set of shotgun reads are grouped based on the sequence of the corresponding tag read adjacent to adaptor 712; however, for the sake of clarity, this set of reads is not shown in FIG. 11.

Figure 11C:
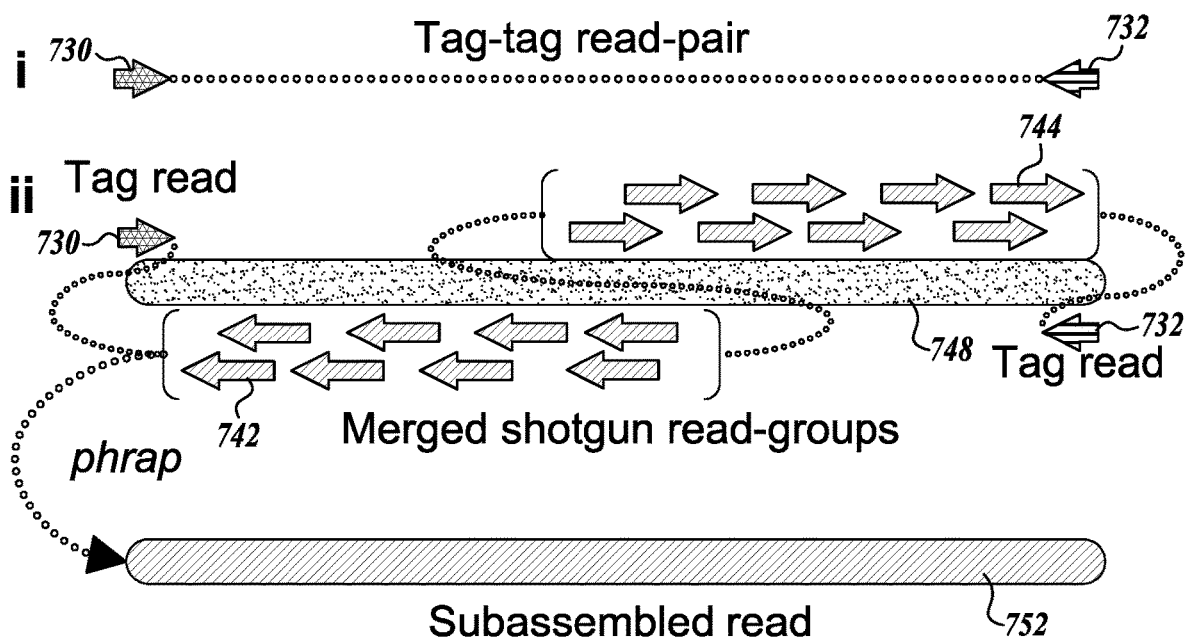

Referring now to FIG. 11C, a related embodiment of the method will be described. In this embodiment, the original genomic or metagenomic fragments 700, having been ligated to adaptors 710, 712, are amplified with a first PCR primer that corresponds to tag adaptor 710 and a second PCR primer that corresponds to tag adaptor 712 to produce amplicons 748 that are competent for Illumina® paired-end sequencing. The first PCR primer includes the flowcell compatibility component of the standard Illumina® paired-end forward adaptor sequence at the 5' end, and the second primer includes the flowcell compatibility component of the standard Illumina® paired-end reverse adaptor sequence at the 5' end. Illumina® paired-end sequencing is performed to identify pairs of tag reads 730, 732 that are derived from opposite ends of the same original fragment 748. Two groups of shotgun reads 742 and 744, obtained as described above (FIG. 11B(i)), which are defined by distinct tag reads 730 and 732, respectively, are merged based on tag-pairing information and together subjected to phrap assembly to generate on or more subassembled reads 752. A representative embodiment of this aspect of the invention is described in Examples 3 and 4.

In another aspect, the invention provides kits for preparing a DNA sequencing library. In one embodiment, the kit comprises a mixture of double-stranded, partially degenerate adaptor molecules, wherein each adaptor molecule comprises a first defined sequence P1, a sequence tag that is fully or partially degenerate within the mixture of adaptor molecules, and a second defined sequence P2. In one embodiment of the kit, the degenerate sequence tag in the adaptor molecule comprises from 5 to 50 randomly selected nucleotides.

In one embodiment, the adaptor molecule provided by the kit comprises a P1 sequence that contains a restriction enzyme recognition site RE1, and a P2 sequence that contains a restriction enzyme recognition site RE2. In another embodiment, the adaptor molecule provided by the kit further comprises a deoxythymidine base at the 3' end.

In some embodiments, the kit also comprises at least one of (a) reagents sufficient for the end-repair and A-tailing of double-stranded DNA molecules, including a thermostable DNA polymerase, an appropriate buffer, and dATP; (b) reagents sufficient to perform isothermal rolling circle amplification and/or multiple displacement amplification, including a strand displacing polymerase, an appropriate buffer; deoxynucleotides, primers complementary to 1 and P2, and random hexamers; (c) reagents sufficient to fragment circular double-stranded DNA molecules, or a nebulizer; (d) a double-stranded adaptor oligonucleotide P3; (e) reagents sufficient to perform PCR amplification of double-stranded DNA, including a thermostable DNA polymerase, an appropriate buffer, deoxynucleotides, and primers complementary to P1, P2 and P3; and (g) instructions for using the kit.

In one embodiment of the kit, a strand displacing enzyme is phi29 DNA polymerase.

In another embodiment, the kit contains a first bridging oligonucleotide BR1 that comprises sequences complementary to RE1 digested P1 sequence and sequence complementary to at least a portion of P3. In one embodiment, the kit contains a second bridging oligonucleotide BR2 that comprises sequences complementary to RE2 digested P2 sequence and sequence complementary to at least a portion of P3.

In one embodiment, the kit provides primers that are complementary to the sense and antisense strands of P1, P2, and P3.

In one embodiment, the kit also provides an adaptor P3 molecule tailed with a deoxythymidine at the 3' ends.

In one embodiment, the kit provides a double-stranded oligonucleotide comprising a defined sequence P4, and primers complementary thereto.

In another embodiment, the invention provides a kit for preparing a DNA sequencing library, the kit comprising a cloning vector comprising restriction enzyme recognition sites that flank the insert cloning site, wherein the restriction enzymes recognition sites are oriented such that the cognate restriction enzymes digest the insert DNA, thereby leaving an end portion of the insert sequence attached to the vector sequence after digestion. In one embodiment, the vector comprises Type IIs restriction enzyme recognition sites.

In another embodiment, the invention provides a kit for preparing a DNA sequencing library, the kit comprising at least one of a plurality of first adaptor molecules, wherein the adaptor molecules may have the same or different sequences. In one embodiment, the first adaptor molecule is a tag adaptor molecule comprising a nucleic acid sequence. In some embodiments, the kit further comprises at least one of a plurality of second adaptor molecules. In one embodiment, the second adaptor molecule is a shotgun adaptor molecule comprising a nucleic acid sequence, wherein the shotgun adaptor sequence is different from the tag adaptor sequence. In one embodiment, the kit further comprises oligonucleotides that include sequence complementary to the first or second adaptor molecules and sequence compatible with Illumina® flowcell sequencing technology.

Examples are provided below to further illustrate different features and advantages of the present invention. The examples also illustrate useful methodology for practicing the invention. These examples should not be construed to limit the claimed invention.

Example 1

This example shows that 46 bp short reads can be correctly subassembled into contiguous sequences greater than 1,000 bp in length using the methods of the invention.

Human genomic DNA (approximately 900 bp fragments) were circularized to a partially degenerate, approximately 100 bp adaptor (P1-20N-P2), and sequencing libraries were generated as described above. P1/P3 and P2/P3 amplicons (each split to two size ranges by gel purification) were sequenced separately, with two reads generated per amplicon (a "read pair"). One sequence read is a 46 bp "shotgun" short read, and the other sequence read is a 20 bp tag sequence. A total of ~5.6 million read pairs were generated for P1/P3 amplicons and ~10.0 million read pairs for P2/P3 amplicons. For each set of amplicons, shotgun short reads were grouped into clusters based on having an identical or nearly identical (i.e. allowing for sequencing errors) tag sequence.

A total of 4,542 clusters representing a total of 1,001,462 shotgun reads (46 bp) were individually subjected to subassembly (average cluster size=220; range=64 to 1024). Short reads that were part of a cluster with less than 64 members (approximately 1.9 million reads) or more than 1,024 members (approximately 12.7 million reads) were excluded from further analysis. Shotgun 46 bp reads within each cluster were assembled using the phrap algorithm, as described in Ewing, B., and Green, P., "Base-Calling of Automated Sequencer Traces Using Phred. II. Error Probabilities," *Genome Res.* 8(3): 186-94, (1998), with parameters set to favor agglomeration despite relatively minimal overlap. For each cluster, phrap may yield multiple subassemblies if all reads cannot be agglomerated. A total of 11,716 subassemblies resulted, each of which was derived from 2 or more shotgun reads (i.e., a given cluster might yield more than one subassembly). The mean size of these 11,716 contigs was 175 bp (standard deviation=174 bp). Subsequent analysis was aimed at validating the accuracy of these subassemblies and focused on the longest subassembled sequence derived from each cluster of associated shotgun reads (this set of longest subassemblies from each cluster is hereafter referred to as the "contigs"). The mean size of these 4,542 contigs was 314 bp (standard deviation=208 bp).

To evaluate the quality of these subassembled contigs, individual contigs were mapped to the human genomic sequence in the NCBI GenBank database using the BLAST algorithm. Specifically, the alignments of 10 of the longest contigs were subjected to manual review. Excluding vector sequence (i.e., the approximately 100 bp P1-20N-P2 adaptor sequence), these subassemblies aligned to human genomic sequence over lengths ranging from 787 bp to 1041 bp. Eight of the 10 alignments demonstrated that "closure" had been achieved, meaning that the subassembled contig defined a full circular sequence that included both the full adaptor and the full approximately 900 bp human genomic DNA fragment. Eight of the 10 alignments were nearly identical to the human genomic sequence in the database (>99% identity). The overall nucleotide identity across these 8 alignments was 7,392 out of 7,411 (99.74%). The differences likely reflect a mixture of true polymorphisms and consensus sequence errors. This accuracy was significantly greater than the mean accuracy for the "raw" 46 bp sequence reads and reflects the consensus of overlapping reads in the subassembly. Two of the 10 sequences were more divergent from human genomic sequences in the database (96.1%; 98.2%) but still defined long subassembly read-lengths (787 bp and 905 bp). However, both of these contigs clearly represent alpha-satellite sequence and the increased divergence rate likely reflects true variation rather than an increased error rate.

Most importantly, for the set of 10 contigs that were analyzed in detail, there were no detected errors in terms of the correctness of the subassemblies across alignment lengths of 787 bp to 1041 bp. These results validate the methods of the present invention. The primary shortcoming of this aspect of the method relates to the overly wide distribution with which each kilobase-scale fragment is sampled with short reads. The overly wide distribution results from non-uniform amplification of the circularized fragment-adaptor pairings by the multiple displacement amplification reaction. Nevertheless, this example demonstrates that 46 bp reads can accurately be "subassembled" into contiguous sequences greater than 1,000 bp in length by applying the methods of the present invention.

Example 2

This example describes the association of sequences based on sequence tags derived from either end of a target DNA fragment. The strategy described in this embodiment is referred to as "keystone" generation and sequencing.

Methods:

Preparation of Genomic DNA Fragments.

Genomic DNA from the organism *Pseudomonas aeruginosa* was mechanically sheared by nebulization. Sheared genomic DNA was size-selected on a polyacrylamide gel to a specific size-range. Most of the size-selected genomic DNA falls in the 1,200-2,000 bp range, although a long-tail smear of additional material shorter than 1,200 bp was also visible when a lower concentration of sheared genomic DNA was loaded on the gel. Sheared, size-selected genomic DNA was end-repaired (Epicentre® End-It™ Repair Kit ERK-70823).

Preparation of a Modified Cloning Vector for the Keystone Strategy.

A modified version of the puc19 vector was generated that included, within the location of the multiple cloning site, an additional segment of DNA that consists of an EcoRV restriction enzyme recognition site flanked by type IIs restriction enzyme recognition sites for BsgI and BtgZ1, oriented towards the EcoRV site. The modified vector, referred to herein as a keystone vector, was cloned into *E. coli* and recovered via plasmid purification (Qiagen). The vector was linearized by digestion with EcoRV to yield blunt ends. The blunt ends were dephosphorylated with Alkaline Phosphatase (CIP).

Cloning of Genomic DNA Fragments into the Modified Vector.

The end-repaired genomic DNA fragments were blunt-end ligated into the linearized vector (NEB® Quick Ligation™ Kit). The ligation mixture was purified on silica spin columns (Qiagen) and transformed into ultracompetent cells (TOP10, Invitrogen) via electroporation. A complex culture with selective antibiotic was grown directly from the electroporation rescue culture, and the complexity of the culture was estimated to be approximately 4,000 unique transformants by plating a subset of the culture.

Preparation of a Recircularized Keystone Sequencing Library.

Plasmid DNA was isolated from the culture (Qiagen) and sequentially digested with the type IIs restriction enzymes BsgI and BtgZI (NEB). The resulting material was end-repaired (Epicentre® End It™-Repair Kit), recircularized (NEB® Quick Ligation™ Kit), and purified on silica spin columns (Qiagen). PCR was performed using primers directed at the keystone segment (i.e., the recircularization junction, which now includes genomic tags derived from BsgI and BtgZ1 digestion). Specific non-vector sequences were appended to the 5' ends of the PCR primers to add sequences required for compatibility with the Illumina® platform.

Results:

Sequencing and Analysis of the Recircularized Keystone Sequencing Library.

A single lane of sequencing of the resulting PCR products was performed with the Illumina® Genome Analyzer using a custom sequencing primer designed to hybridize adjacent to and oriented towards the recircularization junction (expected to be flanked by the BsgI and BtgZ1-derived genomic tags). Approximately 6.2 million single-tag sequencing reads were obtained, with the sequencing reads of sufficient length (28 bp) to cover the full length of both the BsgI and BtgZI derived tags (~11 bp each). Each of these pairs of 11 bp sequences constituted a "keystone tag-pair." To filter out noise (e.g., resulting from sequencing errors), further analysis was restricted to keystone tag-pairs that were observed at least 20 times within the full set of data.

To evaluate whether the keystone tag-pairs were derived from distances corresponding to the expected size distribution, the reads were mapped back to the *Pseudomonas aeruginosa* reference genome. Reads were mapped if there was an exact match for each 11 bp tag. The distance between the locations to which each pair of mapped tags was extracted. When individual tags matched to more than one location in the reference genome, all possible pairs of potential sites of origin were analyzed and the distance with the minimal distance separation was extracted.

Figure 12:
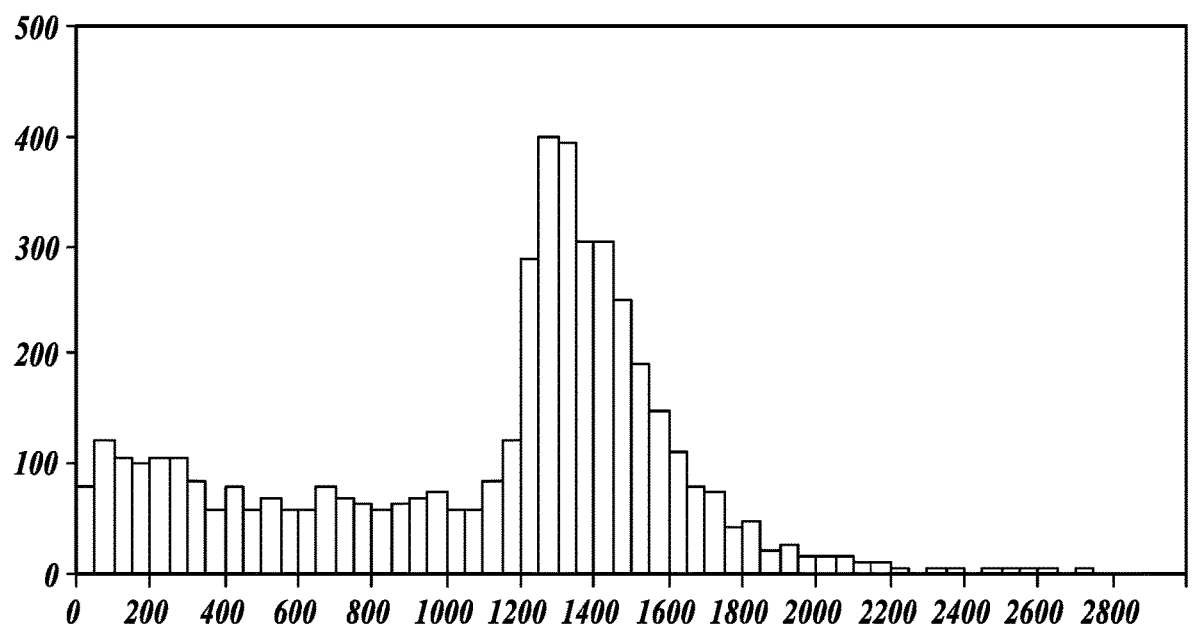
FIG. 12 shows a histogram of minimal distances between potential sites of origin for keystone sequence tags mapped to the *Pseudomonas aeruginosa* reference genome, where the X-axis represents distance between genomic locations of sequence tags in base-pairs and the Y-axis represents the number of sequence tag pairings, as described in Example 2.
Figure 13:
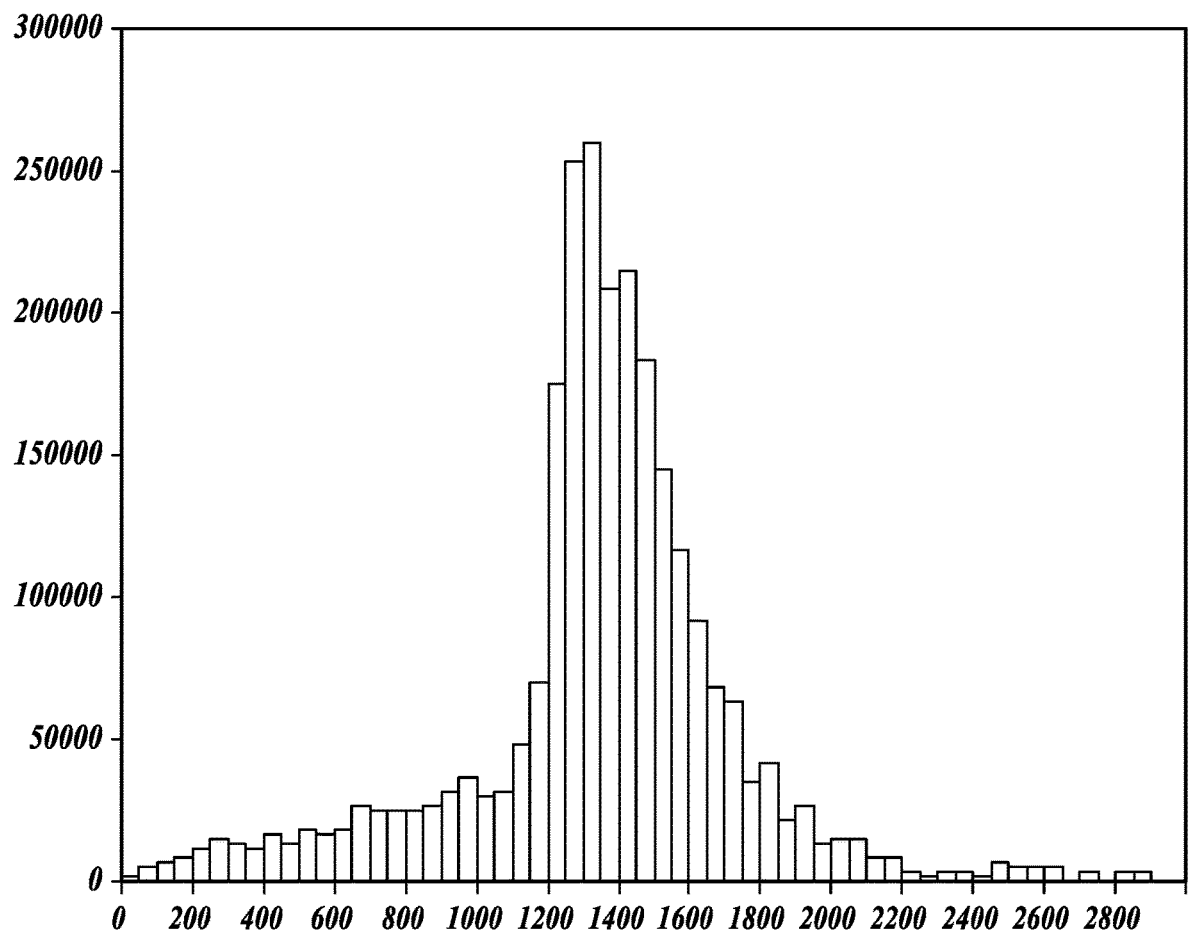
FIG. 13 shows a histogram of the expected mass distribution for *Pseudomonas aeruginosa* genomic fragments that served as starting material, where the histogram of FIG. 12 is adjusted for the mass of fragments within each size range, the X-axis represents distance between genomic locations of sequence tags in base-pairs, and the Y-axis represents mass equivalents in arbitrary units, as described in Example 2.

FIG. 12 shows a histogram of the observed distance distribution between BsgI and BtgZI derived tags. The data show that there is a tight correspondence between the expected distribution (based on the sizes of genomic fragments used as starting material) and the observed distribution of distances between BsgI and BtgZI derived tags (FIG. 12). As shown in FIG. 13, the correspondence between expectation and observation is even greater when the data is corrected for the mass of the fragments size-selected on the gel (as opposed to using the molarity of the observed fragments shown in FIG. 12). Further, the total number of observed keystone sequences (n=4,884) was close to the estimated complexity of the library based on plating of a subset of the transformation culture (n=4,000).

This example shows that the use of sequence tags derived from either end of genomic DNA fragments can be used to map the ends of isolated fragments back to the reference genome. The method described in this example has utility when used with other embodiments of the invention described herein to generate subassemblies of kilobase-scale sized DNA fragments using short read sequencing platforms.

EXAMPLE 3

This example shows that the methods of the invention are useful for generating long, accurate subassembled reads from short read sequencing platforms.

Methods:

Library production can be performed in as few as three days, provided that size-selections are performed without delay and that QIAquick® columns are used to purify DNA from the gel eluate (in place of ethanol precipitation, which is slower and achieves similar yields).

1. Isolation of Source DNA

Genomic DNA Was Obtained From *Pseudomonas aeruginosa* (PAO1).

Metagenomic source DNA was isolated from a microbial population obtained from sediment 63 meters below the surface of Lake Washington and subsequently enriched using Stable Isotope Probing for organisms that utilized methylamine as a food source.

2. Fragmentation of Source DNA

*Pseudomonas:* ~2 ug of genomic DNA was randomly fragmented using nebulization. High molecular weight DNA was diluted to 50 µL in TE Buffer, pH 7.5-8 before being added to the 40% glycerol nebulizing solution containing 325 ul EB and 375 µL 80% glycerol. The nebulizing mixture was pipetted to the bottom of the Invitrogen® Nebulizer (45-0072). The lid was tightly closed and wrapped with Parafilm® laboratory film to limit sample loss. Nebulizing was performed on ice for 15-90 seconds with 6 psi pressurized air. The sample mixture was spun down using a slow centrifuge and the sample was collected by pipette. Repetitive centrifugation/collection was necessary to ensure adequate recovery. DNA was purified using QIAquick® columns and eluted in 30 µL Buffer EB.

Metagenomic: ~2 ug of metagenomic source DNA was randomly fragmented using a Bioruptor® sonication system (Diagenode, New Jersey). High molecular weight DNA was placed in a 1.6 µL Eppendorf tube and diluted to 300 µL in TE. The sample was sheared in the Bioruptor® sonication system for 8×15 minute cycles, with 30-second sonication intervals at high power. DNA was purified using QIAquick® columns (Qiagen 28106) and eluted in 30 µL Buffer EB.

3. End Repair

Fragmented template was end-repaired with the End-It™ DNA End Repair Kit (ERK-70823, Epicentre Biosciences) following the manufacturer's directions. The end-repaired mixture was purified and eluted in 30 µL Buffer EB using a QIAquick® column (Qiagen).

4. Size Selection 500-600 bp fragments (*Pseudomonas*) and 400-500 bp fragments (Metagenomic) of sheared DNA were selected by 6% TBE gel electrophoresis and recovered by ethanol precipitation.

5. A-Tailing

Terminal 3' adenosines were added to size-selected DNA to allow ligation to the T-tailed adaptors. A-tailed DNA was purified by QIAquick® column and eluted in 50 uL of Buffer EB.

6. Ligation to Adaptor

Table 1 shows the type, name, sequence, and SEQ ID NO. of the oligonucleotides used in this embodiment of the methods. 50 uM of custom adaptors was prepared by mixing equal volumes of Ad1 (SEQ ID NO:1) with Ad1_rc (SEQ ID NO:2) and Ad2 (SEQ ID NO:3) with Ad2_rc (SEQ ID NO:4) (Table 1) (initially diluted to 100 uM), heating to 95° C., then turning off the thermal cycler block and cooling passively to room temperature.

Genomic fragments were quantified using a Qubit™ fluorometer (Invitrogen, Q32857) and the Quant-IT™ dsDNA HS kit (Invitrogen, Q32854). Fragments were ligated to adaptors using the Quick Ligation™ Kit (NEB, M2200) at a molar ratio of 1:10 as follows:

|  | *Pseudomonas* | Metagenomic |
| --- | --- | --- |
| Genomic fragments | 13 uL (~1 ng/uL = 36 fm) | 13 uL (0.25 ng/uL + 9.1 fm) |
| Annealed adaptor | 1.44 uL (500 nM = 720 fm) | 1.8 uL (100 nM = 80 fm) |
| dH2O | 0.56 uL | 0.2 uL |
| Quick Ligation buffer (2x) | 15 uL | 15 uL |
| Quick Ligase | 1.5 uL | 1.5 uL |

All components were mixed by brief vortexing and centrifugation. The reaction was carried out at room temperature for 15 minutes and stored on ice.

7. Size Selection

To remove excess unligated adapter, 400-800 bp fragments of ligated DNA were selected by 6% TBE gel electrophoresis and recovered by ethanol precipitation.

8.a. PCR Amplification

To impose a complexity bottleneck and generate multiple copies of genomic fragments, quantitative real-time PCR amplification was performed using Phusion® Hot-Start polymerase (Finnzymes, F-540S) and SYBR® Green (Invitrogen, S-7563) in a MiniOpticon™ thermal cycler (Bio-Rad). Five-prime phosphorylated primers and the Pfu polymerase were used to facilitate concatemerization in the next step.

Complexity was limited by serially diluting the DNA recovered from size selection. For the *Pseudomonas* sample, undiluted, 10-fold, and 100-fold diluted samples were subjected to PCR. Amplification of the 100-fold dilution was split across ten reactions, each containing a 1,000-fold dilution, to improve yield. Because of the lower concentration of the Metagenomic sample during ligation, PCR was performed with both 1 uL (+9 uL H2O, "1×") and 10 uL ("10×") of the adaptor-ligated, size-selected fragments. A given dilution was chosen for further processing based on an assessment of the gel. In general, the least complex sample that did not demonstrate banding on the gel was chosen. Alternatively, a sequencing library can be produced as in 8.d. (below) and sequenced on one lane of a standard paired-end 36 bp to estimate complexity.

Care was taken to ensure that reactions were removed from the thermal cycler prior to the completion of log-phase amplification, since "over-amplification" results in aberrantly slow gel migration of small fragments that will contaminate downstream size-selections.

The components of the PCR reactions for each sample were as follows:

|  | *Pseudomonas* (uL) | Metagenomic (uL) |
| --- | --- | --- |
| Template | 1 | 10 |
| Phusion HF Buffer (5x) | 10 | 10 |
| dNTPs (25 mM) | 0.4 | 0.4 |
| SYBR Green I (1x) | 5 | 5 |
| Ad1_amp (SEQ ID NO: 5) (10 uM) | 2.5 | 2.5 |
| Ad2_amp (SEQ ID NO: 6) (10 uM) | 2.5 | 2.5 |
| dH2O | 28.1 | 19.1 |
| Phusion Hot-Start polymerase | 0.5 | 0.5 |

All components were mixed by brief vortexing and centrifugation. Thermal cycling in a MINIOPTICON™ thermal cycler (Bio-Rad) was performed as follows:
1. 98° C. for 30 sec
2. 98° C. for 10 sec
3. 60° C. for 30 sec
4. 72° C. for 50 sec
5. Plate Read
6. 72° C. for 10 sec
7. Go to 2, 24 times
8. 72° C. for 5 mins
9. Hold 16° C.

Reactions were removed from the cycler as soon as log phase amplification appeared to be ending. Reactions were stored at 4° C. PCR reactions were purified by QIAquick column and eluted in 30 uL of Buffer EB. For the 100-fold dilution sample, reactions were pooled prior to purification.

8.b. Size Selection of Metagenomic PCR Products

Because of length heterogeneity in the PCR products of the Metagenomic library and to maintain a long population of fragments, the purified PCR products were again size-selected from 400-600 bp as described above, then amplified as in step 8.a. (above).

To produce sufficient material to avoid a complexity bottleneck in subsequent steps, 1 uL (*Pseudomonas*) or 10 uL (Metagenomic) of the above PCR product (after step 8.b. for the Metagenomic sample) was split across 8 PCR reactions and amplified again as above, then pooled and purified as above.

8.c. PCR of Bottlenecked Fragment Library for Paired-End Sequencing

To enable pairing of TDRGs from opposite ends of the same original fragment, Metagenomic PCR products from step 8.b. were amplified with oligos that encoded compatibility with the Illumina® flowcell, using iProof™ HF Master Mix (Bio-Rad #172-5311) in a MINIOPTICON™ thermal cycler (Bio-Rad) as below:

|  | Metagenomic (uL) |
| --- | --- |
| Template | 1 |
| SYBR Green I (1x) | 5 |
| Illum_amp_f_Ad1 (SEQ ID NO: 7) (10 uM) | 2.5 |
| Illum_amp_r_Ad2 (SEQ ID NO: 8) (10 uM) | 2.5 |
| dH2O | 14 |
| iProof™ HF master mix (2x) | 25 |

All components were mixed by brief vortexing and centrifugation. Thermal cycling was performed as follows:
1. 98° C., 30 sec
2. 98° C., 10 sec
3. 58° C., 15 sec
4. 72° C., 15 sec
5. Plate Read
6. 72° C., 5 sec 7. Go to 2, 29 times
8. 72° C., 10 mins
9. Hold 16° C.

Sequencing of the TDRG merging library was performed on an Illumina® GA-II with 36 bp paired-end reads according to manufacturer's specifications, except that the following oligos were used: Ad1_seq (SEQ ID NO:9) for the first read and Ad2_seq (SEQ ID NO:10) for the second read.

9. Blunt Ligation of PCR Products

To generate high molecular weight concatemers of PCR products, blunt ligation was performed using the Quick Ligation Kit (NEB, M2200). Reaction components were mixed by brief vortexing and centrifugation, the reaction was carried out at room temperature for 15 minutes, and then stored at 4° C.

10. Fragmentation of High Molecular Weight Concatemers

PCR product ligations were randomly fragmented using the Bioruptor, as described above.

11. End Repair

Fragmented template was end-repaired with the Epicentre Biosciences End-It DNA End Repair Kit as described above. The end-repaired mixture was purified and eluted in 30 μL Buffer EB by QIAGEN® QIAquick® column.

12. A-Tailing

Terminal 3' adenosines were added to end repaired DNA as described above to allow ligation to the T-tailed adaptors. A-tailed DNA was purified by QIAquick® column and eluted in 50 uL of Buffer EB.

13. Ligation to Illumina® Adaptor 50 uM adaptors were prepared by mixing equal volumes of Illum_rev (SEQ ID NO:11) and Illum_rev_rc (SEQ ID NO:12) (initially diluted to 100 uM), heating to 95° C., then turning off the thermal cycler block and cooling passively to room temperature. Fragments were quantified using a Qubit fluorometer (Invitrogen, Q32857) and the Quant-IT dsDNA HS kit (Invitrogen, Q32854). Fragments derived from the *Pseudomonas* PCR were quantified at 20 femtomoles/microliter; A-tailed Metagenomic fragments were quantified at 9 femtomoles/microliter. Fragments were ligated to the Illumina® reverse adaptors (SEQ ID NOs:11, 12) using the Quick Ligation Kit (NEB, M2200) at a molar ratio of 1:20 as follows:

|  | *Pseudomonas* | Metagenomic |
| --- | --- | --- |
| Template | 10 uL | 11 uL |
| Adaptor | 1.14 uL (@ 5 uM) | 4 uL (@ 500 nM) |
| Quick Ligation Buffer (2x) | 15 uL | 15 uL |
| dH2O | 1.16 uL | 0 |
| Quick Ligase | 1.5 uL | 1.5 uL |

All components were mixed by brief vortexing and centrifugation. The reaction was carried out at room temperature for 15 minutes. The reaction was stored on ice. Ligated DNA was purified by QiaQuick® column and eluted in 30 uL of Buffer EB.

14. PCR Amplification

To prepare molecules for Illumina® paired-end sequencing, adaptor-ligated DNA was subjected to real-time quantitative PCR amplification using Phusion® Hot-Start polymerase (Finnzymes, F-540S) and SYBR Green (Invitrogen, S-7563) in a Bio-Rad® MiniOpticon™ thermal cycler. Each sample was amplified in two separate reactions using different pairs of primers to enable amplification of fragments containing sequence from each end of the original fragment. After amplification, size-selection and PCR was performed to enrich for fragments that contained a random break-point at least 150-300 bp distal to the tag read, as shorter fragments will outcompete for cluster formation on the flowcell and dominate sequencing. For this reason, real-time monitoring of amplification is essential to prevent overamplification, which results in aberrant migration of the PCR products on the gel and interferes with downstream size-selection. Care should be taken to ensure that PCR is stopped while the reaction is still in log phase.

The first primer in the mixture below was always Illum_amp_r (SEQ ID NO:13), while the second primer was Illum_amp_f Ad1 (SEQ ID NO:7) in one reaction and Illum_amp_f Ad2 (SEQ ID NO:14) in the other. Four reactions were performed for each primer combination, using in total 10 uL of the 30 uL eluate from the adaptor ligation.

|  | *Pseudomonas* (uL) | Metagenomic (uL) |
| --- | --- | --- |
| Template | 1.25 | 1.25 |
| Phusion HF Buffer (5x → 1x) | 10 | 10 |
| dNTPs (25 mM → 200 uM) | 0.4 | 0.4 |
| SYBR Green I | 5 (1X = 0.1X final) | 2.5 (10X = 0.5X final) |
| Illum_amp_r (SEQ ID NO: 13) (10 uM) | 2.5 | 2.5 |
| Illum_amp_f_Ad* (SEQ ID NO: 7 or 14)(10 uM) | 2.5 | 2.5 |
| dH2O | 27.85 | 30.35 |
| Phusion ® Hot-Start polymerase | 0.5 | 0.5 |

All components were mixed by brief vortexing and centrifugation. Thermal cycling was performed as follows:
1. 98° C., 30 sec
2. 98° C., 10 sec
3. 58° C., 15 sec
4. 72° C., 50 sec
5. Plate Read
6. 72° C., 15 sec
7. Go to 2, 39 times Reactions were removed from the cycler as soon as log phase amplification appeared to be proceeding robustly. Reactions were stored at 4° C. PCR reactions were purified by QIAquick® column and eluted in 30 uL of Buffer EB.

15. Size Selection

Figure 14:
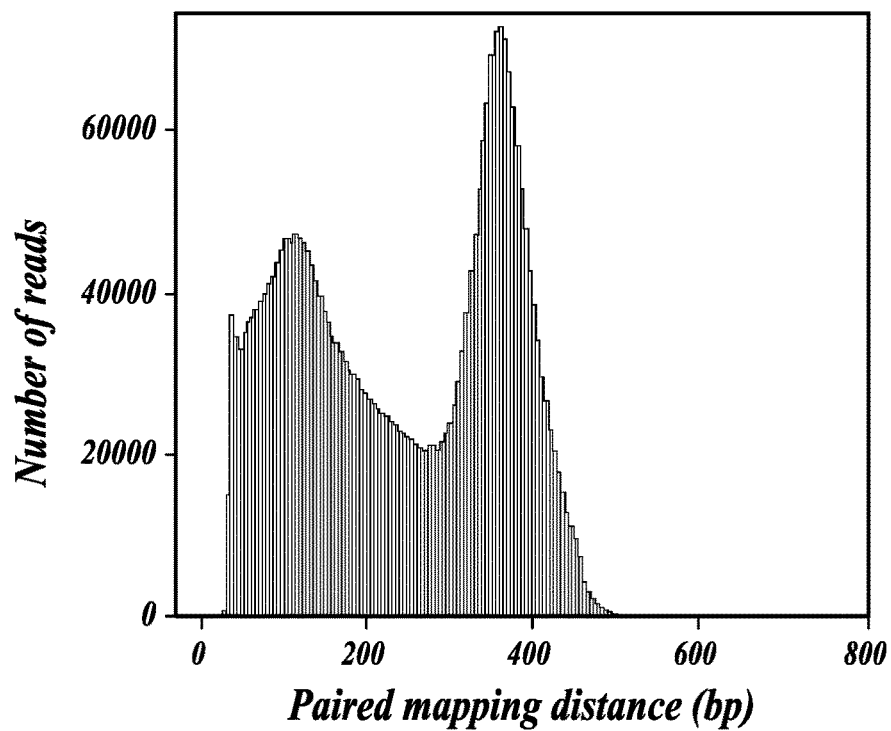
FIG. 14 shows a histogram of the length distribution of shotgun subassembly fragments obtained from a representative embodiment of the method applied to a subset of *Pseudomonas* genomic fragments, as described in Example 3.

Amplified template was size-selected to ranges of 450-600 bp (*Pseudomonas*) and 300-450 bp (Metagenomic) as described above. As shown in FIG. 14, removal of short fragments improves cluster formation uniformity on the flowcell and improves the distribution of reads across the original fragments.

Following size-selection, a final PCR was performed as below to obtain adequate material for Illumina® paired-end sequencing.

|  | *Pseudomonas* (uL) | Metagenomic (uL) |
| --- | --- | --- |
| Template | 5 | 10 |
| Phusion HF Buffer (5x → 1x) | 10 | 10 |
| dNTPs (25 mM → 200 uM) | 0.4 | 0.4 |
| SYBR Green I (10x → 0.5x) | 2.5 | 2.5 |
| Illum_amp_r (SEQ ID NO: 13) (10 uM) | 2.5 | 2.5 |
| Illum_amp_f_Ad* (SEQ ID NO: 7 or 14) (10 uM) | 2.5 | 2.5 |

-continued

|  | Pseudomonas (uL) | Metagenomic (uL) |
| --- | --- | --- |
| dH2O | 26.6 | 21.4 |
| Phusion Hot-Start polymerase | 0.5 | 0.5 |

Thermal Cycling and Purification of PCR Reactions Was Performed as Above.

16. Illumina® Sequencing

After PCR and QIAquick® cleanup, amplicons from the desired size range (450-600 bp for *Pseudomonas*, 300-450 bp for Metagenomic) were subjected to paired-end Illumina® sequencing according to manufacturer's specifications for a 20 bp first read and a 76 bp second read using the following sequencing oligos: Ad1_seq (SEQ ID NO:9) and Ad2_seq (SEQ ID NO:10) on the first read and Illum_seq_r (SEQ ID NO:15) on the second read.

Computational Methods:

Organizing Shotgun Short Reads into Tag-Defined Read Groups (TDRGs):

For all experiments, shotgun reads paired with identical or nearly identical tag sequences were grouped into TDRGs. Since millions of tag reads were involved, an all-against-all comparison to cluster similar tags was not feasible. Instead, a two-step strategy was used to group tag sequences within each experiment. First, perfectly identical tags were collapsed using a simple hash to define a non-redundant set of clusters. From this set, clusters with 4 or more identical tags were identified as "core" clusters and, in descending order by size, were compared to all other tags. Tags matching a given core cluster with up to 1 mismatch were grouped with that core cluster (and removed from further consideration if they themselves defined a smaller core cluster). TDRGs with more than 1,000 members were excluded from downstream analysis to limit analysis of adaptors or other low-complexity sequence.

Subassembly of TDRGs:

Each TDRG was assembled separately using phrap with the following parameters:

-vector_bound 0 -forcelevel 1 -minscore 12 -minmatch 10 -indexwordsize 8

Pre-grouping reads into TDRGs allowed us to use less stringent parameters than the defaults used in traditional assemblies. Parameters were optimized to balance SA read length and accuracy (Table 2). A short read assembler, Velvet (D. Zerbino and E. Birney, *Genome Res.* 18:821-829, 2008), was also tested but did not produce significant gains in SA read length relative to phrap (data not shown).

Filtering and Adaptor-Trimming of SA READs:

SA reads were processed to remove adaptor sequence using the cross_match program provided as part of the phrap suite, using the following parameters:

-minmatch 5 -minscore 14 -screen

The masked regions of the SA reads were then trimmed to retain the longest continuous stretch of unmasked sequence.

In all subsequent analyses, only SA reads that were at least 77 bp in length and were assembled from identically oriented short reads were considered. (NOTE: The read orientation filter is only applicable to SA reads from individual, un-merged TDRGs.) In addition, for length and quality analyses, only the longest SA read from each TDRG was analyzed.

Quality Assessment:

Adaptor-trimmed SA reads were aligned to the *P. aeruginosa* PAO1 reference genome using BLAST with the following parameters:

-p blastn -e 0.001 -m 8 -F F

To analyze error rate as a function of base quality, a method was developed to estimate SA read base call quality. Although phrap does incorporate quality scores from the Illumina® basecaller and produces quality scores for the resulting consensus assembled bases, the base-call quality method makes use of tools designed specifically for short, error-laden reads. A representative subset of ~100,000 TDRGs was chosen from the *Pseudomonas* dataset. For each TDRG, the short read alignment tool maq was used to align short reads to the longest SA read in the TDRG (provided that the longest SA read was longer than 76 bp and was assembled with identically oriented reads). A consensus sequence including quality values was generated by maq (if the consensus base call differed from the base call made by phrap, a quality of 0 was assigned), and SA read bases were then compared to the reference genome to determine the relationship between base quality and error rate. BLAST coordinates of the SA read were used to define the corresponding sequence in the reference genome to which each SA read should be compared and only the component of the SA read that aligned to the reference by BLAST was compared. 35,581 SA reads from the 100,000 TDRGs that were at least 77 bp in length were assembled from identically oriented reads. After maq mapping, 10,853,823 bp of consensus sequence was obtained. Removing bases that were not aligned to the reference by BLAST and ignoring SA reads that were predicted to contain indels reduced the total number of bases by 1.8%, to 10,657,113 bp. Finally, the first and last 5 bp of the BLASTing portion of each SA read was ignored because those bases were essentially constrained by BLAST to be correct and would artificially decrease the observed error rate.

To analyze quality as a function of raw read base quality, maq was used to align reads to the reference, Illumina® base calls were compared to the reference and, for a randomly chosen subset of 1 million bases, the error rate as a function of Illumina® base call quality was determined.

To analyze quality as a function of SA read position, the same representative subset of SA reads from ~100,000 TDRGs was aligned to the reference using BLAST as above and the base calls at each position of the SA read were compared to the reference. Once again, analysis was restricted to SA reads that were at least 77 bp in length, assembled from identically oriented reads, aligned to the reference genome, and were not predicted to contain indels. As above, the first and last 5 bp of sequence was trimmed to prevent artificial suppression of error rates. Only those positions containing at least 1,000 members were plotted. Finally, positions were binned into groups of three for display purposes.

To analyze quality as a function of raw read position, a representative lane of reads used for the subassembly process was aligned to the reference genome using maq and the error rate at each position was determined by comparing read base calls to reference bases for each read.

TDRG Merging Algorithm:

Paired 36 bp reads were obtained from a sequencing library prepared from bottlenecked, adaptor-ligated metagenomic fragments as described in the Supplementary Experimental Methods, then trimmed computationally to 20 bp to correspond to the length of the tag reads that were obtained during sequencing of the subassembly libraries.

To prevent sequencing errors at the ends of the reads from creating spurious tags and tag-pairs, the reads were trimmed further to the first 15 bp. TDRG pairs were defined in descending order of tag-pair abundance, and tags previously assigned to TDRG pairs were removed.

Velvet Assembly of Shotgun Metagenomic Library:

Paired 36 bp reads were first subjected to Velvet assembly using the following parameters:

-exp_cov 20 -cov_cutoff 2 -ins_length 250

Resulting scaffolds were then split into contigs that did not contain N's, because it was reasoned that the performance of important efforts like gene discovery and phylogenetic classification would depend solely on the length of contiguous regions of defined bases.

To optimize the length of contigs produced by Velvet, a histogram of coverage was generated and Velvet was run again with the same input data and using the following parameters:

-exp_cov 28 -cov_cutoff 20 -ins_length 250

Imposing a higher minimum coverage cutoff reduces the noise of the assembly process, allowing the assembler to extend paths more confidently and produce longer contigs. However, it is possible that this higher cutoff may discard reads from more rare sequences in the sample, thereby artificially collapsing sample diversity.

To allow a more direct comparison to a phrap assembly of SA reads, all contigs produced by Velvet with the more inclusive parameter set (-cov_cutoff 2) were subjected to phrap assembly with the following parameters:

-vector_bound 0 -default_qual 30

Phrap Assembly of Metagenomic SA Reads:

All SA reads from the metagenomic sample, including SA reads from both unmerged and merged TDRGs that were longer than 76 bp and assembled from properly oriented reads (unmerged only), were pooled and subjected to an additional round of phrap with the following parameters:

-vector_bound 0 -default_qual 30

Comparison to Sanger Data with Blast and Maq:

Contigs produced from SA reads via phrap and contigs produced from shotgun short reads via phrap and Velvet were aligned to one another and to the recently collected Sanger data from the same sample (JGI IMG/M Taxon Object ID 2006207002, NCBI accession number ABSR01000000) using BLAST with the following parameters:

-p blastn -e 1e-6 -m 8 -F F

Two bases were considered to be a shared position between two datasets if they were contained in a BLAST alignment at least 100 bp long and with at least 98% identity, and only if the two bases were in the BLAST alignment with the highest bitscore of all the BLAST alignments between the two datasets involving either base.

To define the potential coverage present in the sequencing library, 76 bp reads collected for subassembly (the second read in the tag-shotgun read-pair) and paired-end 36 bp reads collected for Velvet assembly were aligned to the Sanger data using the short-read alignment tool maq with default parameters and the pileup function was used to determine coverage.

TABLE 1

Sequences of Oligonucleotides Used in a Representative Embodiment of the Methods.*

| Type | Name | Sequence | SEQ ID NO: |
|---|---|---|---|
| Bottleneck adaptor oligos | Ad1 | TCGCAATACAGAGTTTACCGCATT | 1 |
| | Ad1 rc | /5Phos/ATGCGGTAAACTCTGTATTGCGA | 2 |
| | Ad2 | CTCTTCCGCATCTCACAACCTACT | 3 |
| | Ad2 rc | /5Phos/GTAGGTTGTGAGATGCGGAAGAG | 4 |
| Bottleneck PCR primers | Ad1_amp | /5phos/TCGCAATACAGAGTTTACCGCATT | 5 |
| | Ad2_amp | /5phos/CTCTTCCGCATCTCACAACCTACT | 6 |
| Sequencing PCR primers | Illum_amp f Ad1 | AATGATACGGCGACCACCGAGATCTACACCAATGGAGCTCGCAATACAGAGTTTACCGCATT | 7 |
| | Illum_amp _f_Ad2 | AATGATACGGCGACCACCGAGATCTACACATCGAGAGCCTCTTCCGCATCTCACAACCTACT | 14 |
| | Illum_amp _r | CAAGCAGAAGACGGCATACGAGATCGGTCTCGGCATTCCTGCTGAACCGCTCTTCCGATCT | 13 |
| TDRG merging PCR primer | Illum_amp r Ad2 | CAAGCAGAAGACGGCATACGAGATATCGAGAGCCTCTTCCGCATCTCACAACCTACT | 8 |
| Sequencing oligos | Ad1 seq | CAATGGAGCTCGCAATACAGAGTTTACCGCATT | 9 |
| | Ad2_seq | ATCGAGAGCCTCTTCCGCATCTCACAACCTACT | 10 |
| | Illum_seq_r | CGGTCTCGGCATTCCTGCTGAACCGCTCTTCCGATCT | 15 |

TABLE 1-continued

Sequences of Oligonucleotides Used in a
Representative Embodiment of the Methods.*

| Type | Name | Sequence | SEQ ID NO: |
|---|---|---|---|
| Illumina® adaptor oligos | Illum_rev | CTCGGCATTCCTGCTGAACCGCTCTT CCGATC*T | 11 |
| | Illum_rev_rc | /5Phos/GATCGGAAGAGCGGTTCAGCA GGAATGCCGAG | 12 |

*Oligos were obtained from Integrated DNA Technologies. An asterisk indicates a phosphorothioate bond. /5Phos/ indicates a five-prime phosphate modification.

Results:

*P. aeruginosa* (PAO1) genomic DNA was randomly fragmented and size-selected to ~550 bp. The size selected genomic fragments were subjected to the methods described in FIGS. 11A and 11B. An Illumina® Genome Analyzer II was used to generate 56.8 million (M) read-pairs (20 tag read+76 shotgun read). As shown in Table 2, read pairs were grouped into Tag-Defined Read-Groups (TDRGs) by the 20 bp tag (allowing for 1 mismatch) and the 76 bp shotgun reads within each TDRG were separately subjected to local assembly with phrap, using parameters that favored agglomeration even with relatively minimal overlap.

TABLE 2

Phrap optimization of *Pseudomonas* TDRGs*

| Min match | Min score | Force level | Index word size | # of TDRGs | Mean longest SA read | Median longest SA read | Fraction of non- BLAS Ting SA's | Fraction of SA's BLASTing <90% of length | Fraction of mismatches among BLASTing bases |
|---|---|---|---|---|---|---|---|---|---|
| 12 | 12 | 1 | 10 | 2619 | 361.6 | 403 | 0.004964 | 0.02993 | 0.001513 |
| 10 | 12 | 1 | 10 | 2619 | 364.4 | 406 | 0.004964 | 0.0284 | 0.001543 |
| 10 | 12 | 1 | 8 | 2619 | 364.4 | 406 | 0.004964 | 0.0284 | 0.001543 |
| 10 | 10 | 1 | 8 | 2619 | 369.5 | 409 | 0.004964 | 0.04106 | 0.001551 |
| 8 | 10 | 1 | 8 | 2619 | 371.9 | 411 | 0.004964 | 0.04643 | 0.001579 |

*A representative subset of 10,000 *Pseudomonas* TDRGs was randomly selected and subjected to phrap assembly using different parameters and the resulting lengths and qualities of the longest subassemblies from each TDRG were assessed. The parameters of minmatch 10, minscore 12, force level 1, and index word size 8 achieved the optimal balance between assembly accuracy, measured as the fraction of subassembled reads BLASTing across at least 90% of their length in a single BLAST hit (and the fraction removed because of oppositely oriented reads, not shown here), and subassembled read length.

Subsequent analyses retained only the longest subassembled read ("SA read") from TDRGs with at least 10 members. Subassembled reads were expected to be derived from identically oriented shotgun reads, and those that were not (1.7%) were discarded. Furthermore, TDRGs that failed subassembly entirely (an additional 0.35%) were also discarded.

Figure 15:
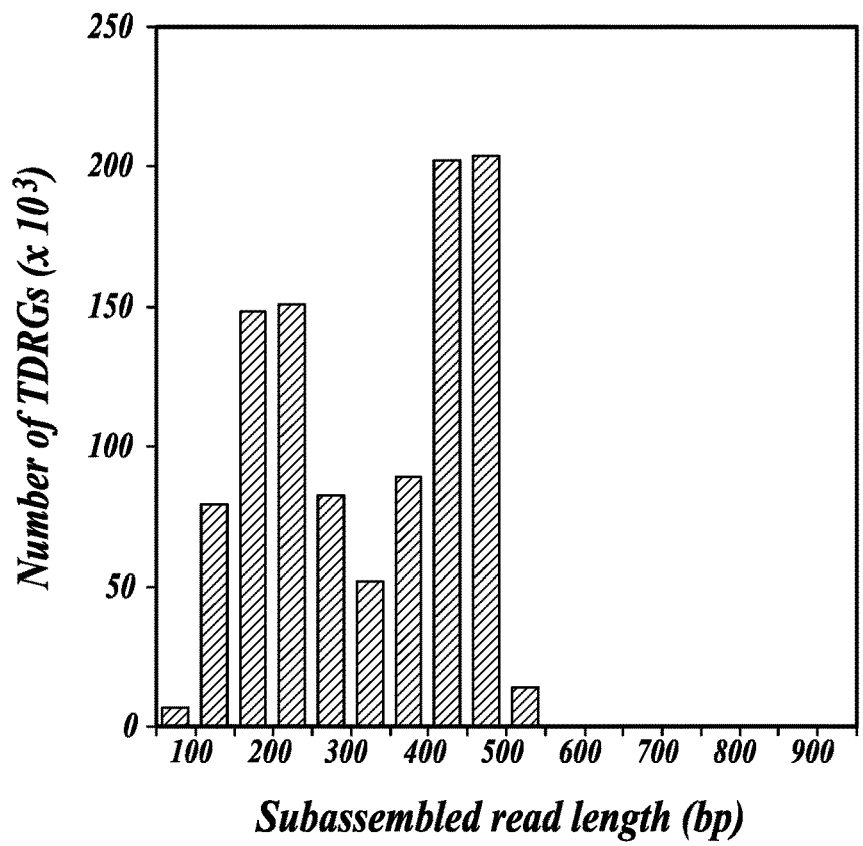
FIG. 15 shows a histogram of the distribution of subassembled read length for the *P. aeruginosa* genomic sample; as described in Example 3.

As shown in FIG. 15 and Table 3, the above analysis resulted in 1.03 M SA reads, with a median length of 346 bp and an N50 of 418 bp.

TABLE 3

Summary Statistics for Subassembled Reads.*

| Sample | Original fragment size (bp) | # of read-pairs | # of filtered TDRGs | Median length (bp) | N50 (bp) | Longest SA read (bp) |
|---|---|---|---|---|---|---|
| *P. aeruginosa* | ~550 | 56.8M | 1,029,313 | 346 | 418 | 916 |
| Metagenomic | ~450 | 21.8M | 263,040 | 259 | 280 | 649 |
| Metagenomic (merged) | ~450 | 21.8M + 1.8M | 139,636 (69,818 pairs) | 413 | 432 | 742 |

*For the two samples used and the two analyses performed of the methylamine-enriched metagenomic sample, Table 3 shows the original genomic or metagenomic fragment size in bp, the number of Illumina® read-pairs that were used to generate subassembled (SA) reads (merged analysis also shows the number of reads used to pair tags), the number of TDRGs after filtering for successful assembly and properly oriented contributing reads, the median length of the longest SA read from each filtered TDRG, the N50 or length of the longest SA read from each filtered TDRG such that 50% of the base pairs contained in all of the longest SA reads are in SA reads at least as long as the N50, and the longest SA read overall.

Figure 16:
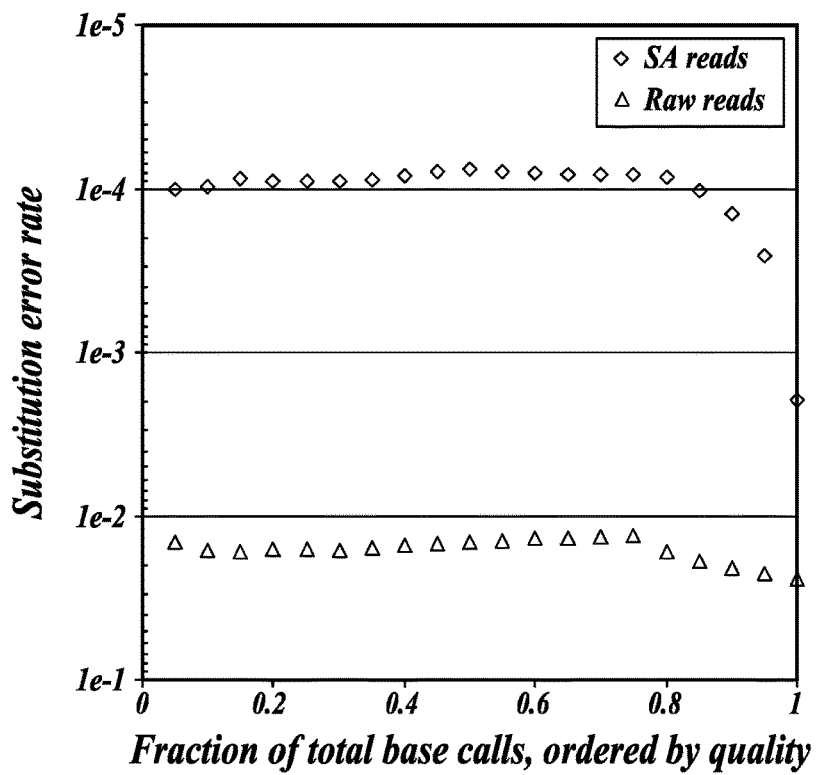
FIG. 16 shows a graph of the cumulative per-base substitution error rate of base calls binned as a fraction of descending base quality in raw (triangles) and subassembled (diamonds) reads, as described in Example 3.
Figure 17:
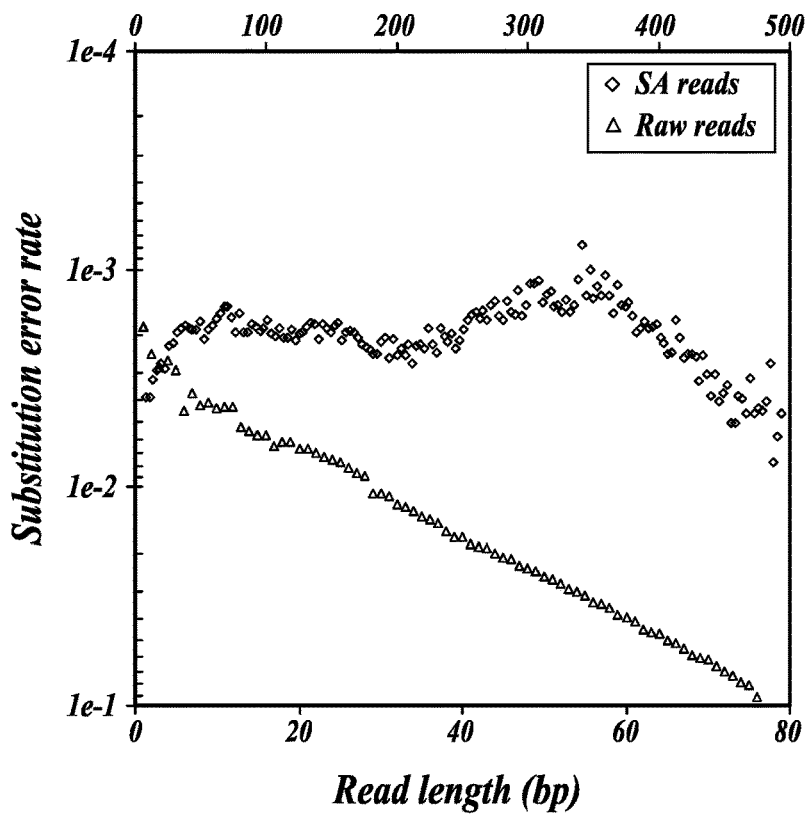
FIG. 17 shows a graph of the substitution error rate of base calls as a function of base position in raw (triangles; lower X-axis) and subassembled (diamonds, upper axis (bp)) reads, as described in Example 3.

As shown in FIG. 14, a bimodal distribution of SA read length was observed, which is likely due to uneven coverage of the original fragment by the nested library, especially in TDRGs with fewer read-pairs. The longest SA read was 916 bp, likely an outlier from the gel-based size-selection but nonetheless an indicator of method potential. To assess quality, the SA reads were mapped to the PAO1 reference (C. K. Stover, X. Q. Pham, A. Erwin et al., Nature 406(6799): 959 (2000)). This analysis showed that 99.84% had significant alignments with BLAST (S. F. Altschul, T. L. Madden, A. A. Schaffer et al., Nucleic Acids Res. 25(17):3389 (1997)). Notably, the substitution error rate within alignments was 0.197% (Phred Q27), while the raw Illumina® shotgun reads had an error rate of 2.4% (Phred Q16). To further characterize the distribution of base qualities, quality scores for individual bases within SA reads were calculated using the quality scores of the contributing shotgun reads (H. Li, J. Ruan, and R. Durbin, Genome Res. (2008)). As shown in FIG. 16, the 80% of bases in SA reads with the highest estimated quality scores were 99.99% accurate (Phred Q40) with respect to substitution errors when compared to the PAO1 reference. Finally, the substitution error rate as a function of position along the SA read was calculated. Importantly, as shown in FIG. 17, the low overall error rate of 1 per 500 bp was maintained for hundreds of bases in the SA reads, but quickly decayed within the much shorter shotgun reads.

Example 4

This example demonstrates that the subassembly method facilitates significant improvements in assembly of short read sequencing data from metagenomic libraries to useful lengths.

Figure 18:
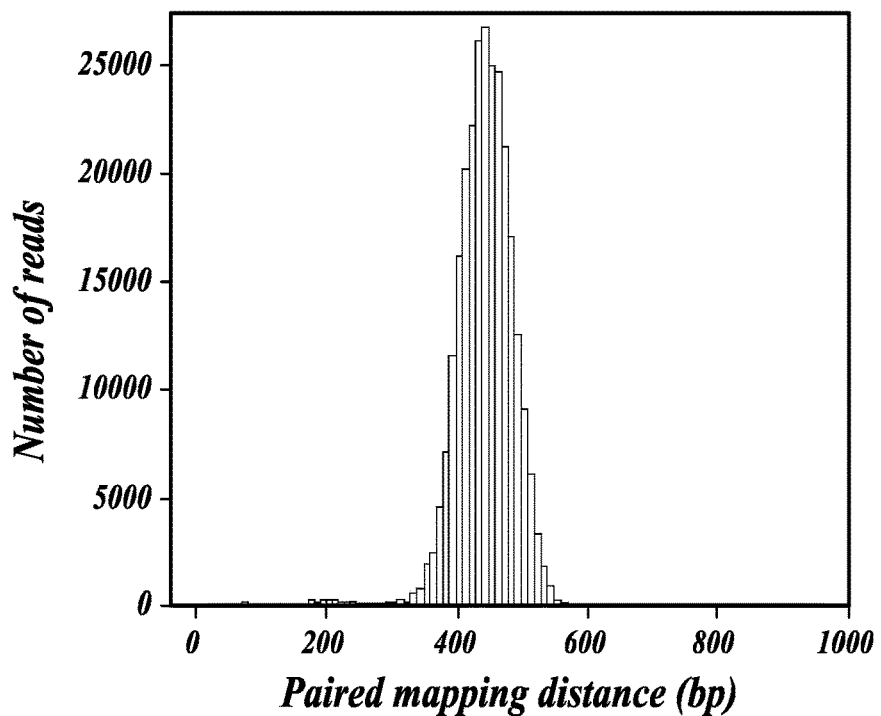
FIG. 18 shows a histogram of the length distribution of metagenomic fragments, as described in Example 4.
Figure 19:
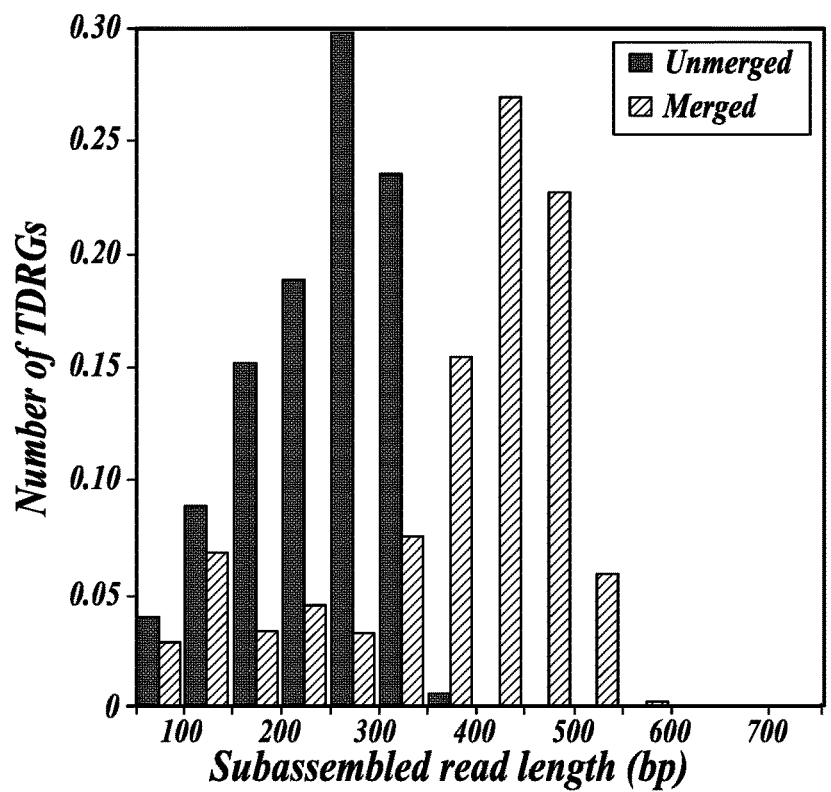
FIG. 19 shows a bar graph of the distribution of subassembled read length for the metagenomic sample comparing unmerged (filled bars) and merged (hatched bars) Tag-Defined Read Groups, as described in Example 4.

The subassembly method was applied to a complex metagenomic sample comprising total DNA isolated from a microbial community first obtained from sediment 63 meters deep in Lake Washington (Seattle, Wash.) and subsequently enriched for methylamine-fixing microbes (M. G. Kalyuzhnaya, A. Lapidus, N. Ivanova et al., Nat. Biotechnol. 26(9):1029 (2008)). As shown in FIG. 18, the length distribution of the metagenomic library was about 450 bp. The same method described above in Example 3 for *Pseudomonas* was applied to the metagenomic library sample having a more stringent complexity bottleneck. As shown in FIG. 19 and Table 3, a total of 21.8 M read-pairs (20 bp tag read+76 bp shotgun read) was obtained resulting in 263,024 SA reads where the median length was 259 bp, the N50 was 280 bp, and the longest SA read was 649 bp.

As shown in FIG. 11C, in addition to the nested shotgun reads that were used to produce SA reads, 1.8 M paired-end reads from the original long-fragment library (2×20 bp) were obtained, which allowed TDRGs whose tags were observed as a read-pair to be merged. Approximately 52% of the metagenomic TDRGs were merged in this fashion and shotgun reads from both TDRGs were together subjected to assembly. As shown in FIG. 19 and Table 3, SA reads from merged pairs of TDRGs (taking only the longest contiguous read) had a median length of 413 bp and an N50 of 432 bp, and the longest SA read was 742 bp.

Tag-directed, local assembly of short reads may circumvent many challenges associated with de novo assembly of short reads, especially in the context of metagenomics, where the relative representation of organisms is highly non-uniform. Therefore, a standard Illumina® shotgun paired-end library from the same metagenomic DNA sample was generated. Because phrap cannot be used to directly assemble millions of short reads, the shotgun reads (36 bp×2) were assembled using Velvet, a popular short-read assembler (D. R. Zerbino and E. Birney, Genome Res. 18(5):821 (2008)) (Table 4). To perform the most direct comparison possible, a total of 2.2 Gb of shotgun sequence data was used, which was equal in total bases to the full amount of data collected and used with the subassembly approach. To optimize contig length, the Velvet assembler was run using parameters that are likely to favor assembly of highly represented sequences at the expense of more rare sequences. Indeed, longer contigs were produced at the expense of total non-redundant sequence. As shown in Table 4, when contigs produced by Velvet were also subjected to the more inclusive parameters to additional assembly using phrap, only minimal additional assembly was produced. This result suggests that any observed differences in assembly were not the result of using different assemblers.

Figure 20:
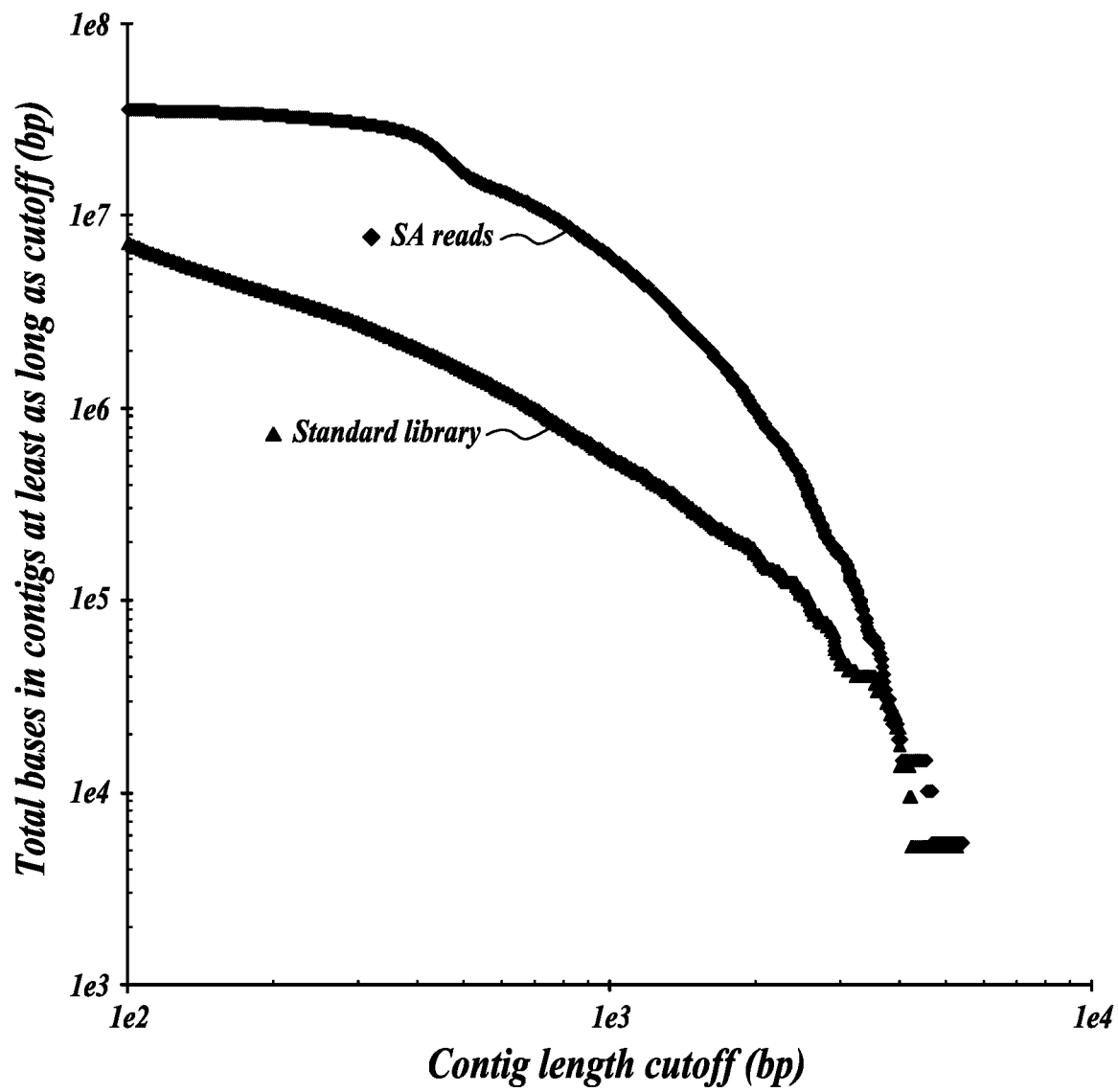
FIG. 20 shows a graph comparing the assembly of metagenomic subassembled reads (diamonds) to an assembly of a standard shotgun library (triangles), as described in Example 4.

Direct assembly of shotgun short reads with Velvet and phrap generated 7.2 Mb of sequence (min. 100 bp) with an N50 of 221 bp. By comparison, phrap assembly of all SA reads that met length and orientation filters generated considerably more total sequence data in longer contigs, producing 35.7 Mb of sequence with N50 of 482 bp (Table 4). As shown in FIG. 20, when compared to assembly of shotgun reads by Velvet and phrap, assembly of SA reads generated 10.7 times as many total base-pairs of sequence in contigs at least 500 bp long and 11.1 times as many total base-pairs of sequence in contigs at least 1 kb long.

TABLE 4

Summary Statistics From Assembly of Metagenomic SA Reads Versus Assembly of a Standard Shotgun Library.*

| Input | Assembly strategy | # of contigs | N50 | Longest contig | Total bases |
|---|---|---|---|---|---|
| Standard shotgun library | Velvet (low min. cov.) | 35,554 | 219 bp | 5,249 bp | 7.3 Mb |
|  | Velvet (low min. cov.) + phrap | 35,016 | 221 bp | 5,249 bp | 7.2 Mb |
|  | Velvet (high min. cov.) | 14,373 | 388 bp | 16,698 bp | 4.3 Mb |
| Subassembled reads | phrap | 82,457 | 482 bp | 5,400 bp | 35.7 Mb |

*Comparison of various strategies to assemble short reads from a standard Illumina ® shotgun library prepared from the metagenomic sample to phrap assembly of the full complement of SA reads from the same sample. Listed is the assembly input, the assembly strategy used (low coverage = 2x minimum, high coverage = 20x minimum), the number of contigs produced (at least 100 bp in length), the N50, the length of the longest contig produced, and the total bases of sequence produced. A high coverage cutoff during Velvet assembly improved contig length at the expense of total sequence produced, and also likely at the expense of sequences from less highly represented organisms.

Figure 21:
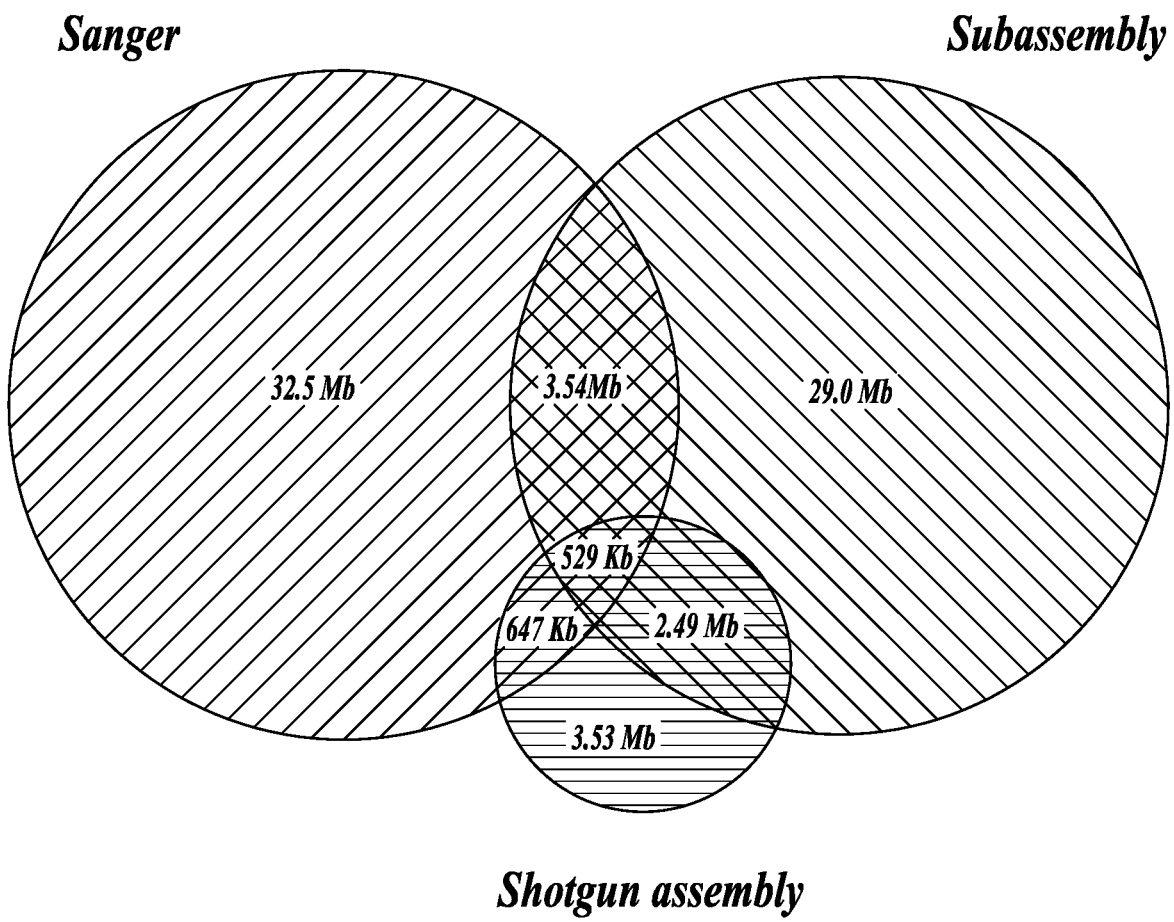
FIG. 21 shows a venn diagram illustrating reciprocal coverage across data sets, as described in Example 4.

To further evaluate the performance of the present methods against standard short-read sequencing in the context of a metagenomic sample, assembled contigs generated from paired-end short reads and by the subassembly methods described herein were compared to the 37.2 Mb of Sanger sequence recently reported from the same sample (M. G. Kalyuzhnaya, A. Lapidus, N. Ivanova et al., Nat. Biotechnol. 26(9):1029 (2008)). The presence of a complex population of related and unrelated organisms in the sample precluded a direct evaluation of assembly quality as compared to the Sanger data. Therefore, BLAST was used to align contigs against the assembled Sanger sequence using stringent parameters in order to conservatively estimate the effective coverage achieved by each method. As shown in FIG. 21, contigs produced from short reads and the Sanger "reference" contained 1.18 Mb of sequence in common, contigs produced from SA reads shared 4.19 Mb of sequence with the Sanger data, and contigs from short reads and from SA reads contained 3.14 Mb in common. The alignment tool maq was used to assess coverage by both sets of raw Illumina® reads. The assembly of short reads using Velvet followed by phrap collapsed coverage by nearly a factor of 15, while subassembly followed by phrap assembly of SA reads collapsed coverage by less than a factor of 3.

While the complexity of this metagenomic population likely remains under-sampled, the methods described herein covered more than three times as much of the Sanger data and better maintained the complexity of the raw data when compared to assembly of a standard short-read library. In addition, the present method was able to generate a comparable amount of total sequence compared to state-of-the-art capillary electrophoresis methods, albeit in somewhat shorter contigs (N50 of 482 bp vs 877 bp), with considerably less effort (three Illumina® sequencing lanes versus hundreds of Sanger sequencing runs).

This example demonstrates that subassembly facilitates significant improvements in assembly of short read sequencing data from metagenomic libraries to useful lengths, which should aid in length-dependent sequence analyses such as accurate phylogenetic classification (Arthur Brady and Steven L. Salzberg, *Nat. Meth.* (advance online publication) (2009)), and gene discovery (A. L. Delcher, D. Harmon, S. Kasif et al., *Nucleic Acids Res.* 27(23):4636 (1999)).

The present methods provide a straightforward, in vitro protocol that significantly extends the capability of cost-effective second-generation sequencing platforms to yield highly accurate, long sequencing reads. This approach may be most useful for metagenomics, although there are many other applications where long reads have continued to be critical, e.g., in assessing VDJ diversity (J. A. Weinstein, N. Jiang, R. A. White, 3rd et al., *Science* 324(5928):807 (2009)). While initial experiments were focused on long DNA fragment libraries in the 400-600 bp range, SA reads of nearly 1 kilobase were also observed. In concert with the tag-pairing approach (FIG. 11C), this could potentially extend the length of SA reads to as long as 2 kilobases, i.e., nearly twice as long as even the longest Sanger sequencing reads. This method may significantly extend the utility of the most cost-effective second-generation sequencing platforms to environmental metagenomics and may prove useful in other contexts as well.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for detecting an error occurring in the preparation and/or sequencing of a target nucleic acid molecule, the method comprising:
   (a) incorporating a first nucleic acid adaptor molecule comprising a first tag sequence into a target nucleic acid molecule to produce a first tagged nucleic acid molecule;
   (b) amplifying the first tagged nucleic acid molecule to provide an input library comprising a first plurality of amplified DNA molecules, wherein the amplified DNA molecules comprise a sequence corresponding to at least a portion of the first tag sequence and a sequence corresponding to at least a portion of the target nucleic acid molecule;
   (c) sequencing at least a portion of the first plurality of amplified DNA molecules to produce a plurality of sequencing reads corresponding to the target nucleic acid molecule and comprising a sequence corresponding to the first tag sequence;
   (d) grouping the plurality of sequencing reads that correspond to the target nucleic acid molecule and comprise the sequence corresponding to the first tag sequence to produce a plurality of grouped sequencing reads; and
   (e) detecting whether an error exists at a nucleotide position, wherein an error exists when variation of nucleotide identity exists among the grouped sequencing reads at a position corresponding to a nucleotide in the target nucleic acid molecule.

2. The method of claim 1, wherein the method further comprises determining the correct identity of a nucleotide at the position where the variation of nucleotide identity is detected, wherein the correct identity is determined based on a consensus of individual base calls in the plurality of grouped sequencing reads.

3. The method of claim 2, wherein the consensus of individual base calls is the most common base call at the nucleotide position in the plurality of grouped sequencing reads.

4. The method of claim 1, wherein the method further comprises eliminating from further analysis the identity of the nucleotide at the position in a sequencing read where an error is detected.

5. The method of claim 1, wherein the method further comprises eliminating from further analysis a sequencing read determined to comprise a sequencing error.

6. The method of claim 5, wherein the sequencing read is determined to comprise a sequencing error when it comprises a nucleotide base call that differs from the consensus nucleotide base call provided by the plurality of grouped sequencing reads.

7. The method of claim 1, wherein the first tag sequence is a random sequence.

8. The method of claim 1, wherein the target nucleic acid molecule is a member of a target library comprising a plurality of nucleic acid molecules and step (b) comprises amplifying the plurality of nucleic acid molecules to provide the input library.

9. The method of claim 8, wherein the first tag sequence comprises a unique nucleotide sequence that distinguishes the at least one member of the target library from other members of the target library.

10. The method of claim 1, further comprising fragmenting at least a portion of the first plurality of amplified DNA molecules in the input library from step (b) to produce a plurality of linear DNA fragments having a first end and a second end.

11. The method of claim 10, further comprising attaching at least one second nucleic acid adaptor molecule to one or both ends of at least one of the plurality of linear DNA fragments, wherein the second adaptor molecule comprises a defined-sequence.

12. The method of claim 11, further comprising amplifying the plurality of linear DNA fragments to produce a second plurality of amplified DNA molecules, wherein at least one of the second plurality of amplified DNA molecules comprises a sequence corresponding to the first tag sequence, a sequence corresponding to at least a portion of the second adaptor molecule, and a sequence corresponding to at least a portion of the target nucleic acid molecule.

13. The method of claim 12, wherein at least a portion of the second plurality of amplified DNA molecules is sequenced in step (c) of the method to produce a plurality of associated sequence read pairs for each sequenced DNA molecule corresponding to the target nucleic acid molecule.

14. The method of claim 13, wherein the associated sequence read pairs comprise a first sequence read and a second sequence read, wherein the first sequence read comprises the first tag sequence of the first adaptor that uniquely identifies the target nucleic acid molecule, and wherein the second sequence read comprises a sequence adjacent to the defined sequence of the second adaptor and represents the sequence adjacent to a fragment breakpoint in the amplified DNA molecule.

15. The method of claim 14, wherein a plurality of second sequence reads that are each associated with a first sequence read are grouped in step (d) of the method, wherein the first sequence read contains the first tag sequence identifying the target nucleic acid molecule.

16. The method of claim 1, wherein the grouping step (d) comprises generating an alignment of the plurality of sequencing reads.

17. The method of claim 1, wherein the grouping step (d) comprises comparing the sequencing reads to a reference sequence.

18. The method of claim 1, wherein the incorporating the first nucleic acid adaptor molecule into the target nucleic acid molecule in step (a) results in at least one circular nucleic acid molecule comprising the first nucleic acid adaptor and the target nucleic acid molecule.

19. The method of claim 1, wherein the target nucleic acid molecule is a genomic DNA fragment or copy thereof.

20. The method of claim 1, wherein the target nucleic acid molecule is a cDNA molecule.

* * * * *